US010832364B2

(12) United States Patent
Tayal et al.

(10) Patent No.: US 10,832,364 B2
(45) Date of Patent: Nov. 10, 2020

(54) INFORMATION SYSTEM FOR PHYSICIANS

(71) Applicant: DRFIRST.COM, INC., Rockville, MD (US)

(72) Inventors: Kamal Tayal, Moga Punjab (IN); Andrew Mutch Curtis, Germantown, MD (US); Yixin Hou, Rockville, MD (US); Christopher John Cresswell, Potomac, MD (US); Dennis DiVenuta, Far Hills, NJ (US); Yu-Fui Hung, Bethesda, MD (US)

(73) Assignee: DrFirst.com, Inc., Rockville, MD (US)

( * ) Notice: Subject to any disclaimer, the term of this patent is extended or adjusted under 35 U.S.C. 154(b) by 0 days.

(21) Appl. No.: 16/430,217

(22) Filed: Jun. 3, 2019

(65) Prior Publication Data
US 2019/0385259 A1 Dec. 19, 2019

Related U.S. Application Data

(63) Continuation of application No. 13/565,164, filed on Aug. 2, 2012, now Pat. No. 10,346,938, which is a
(Continued)

(51) Int. Cl.
*G06Q 50/22* (2018.01)
*G06Q 30/02* (2012.01)

(52) U.S. Cl.
CPC ............. *G06Q 50/22* (2013.01); *G06Q 30/02* (2013.01)

(58) Field of Classification Search
CPC .... G06Q 50/22; G06Q 50/24; G06F 19/3456; G06F 19/326; G06F 19/36; G16H 10/20;
(Continued)

(56) References Cited

U.S. PATENT DOCUMENTS

| 5,391,139 A | 2/1995 | Edmundson |
| 5,845,255 A | 12/1998 | Mayaud |

(Continued)

FOREIGN PATENT DOCUMENTS

| JP | 2001357131 A | 12/2001 |
| JP | 3974800 B2 | 9/2007 |
| WO | 2004053620 A2 | 6/2004 |

OTHER PUBLICATIONS

"Rules—2010", http://www.deadiverision.usdoj.gov/fed_regs/rules/2010/fr0331.htm, U.S. Department of Justice Office of Diversion Control, pp. 1-11.
(Continued)

*Primary Examiner* — Joseph D Burgess
(74) *Attorney, Agent, or Firm* — Brake Hughes Bellermann LLP

(57) ABSTRACT

A computer system identifies the permutation of supplemental materials most effective at increasing adherence for each of a plurality of different medication diagnostic codes and provides the materials at an optimal point in time. An example system includes a supplemental program (SP) module implemented on a computing device that receives a plurality of supplemental programs associated with the one or more prescribed substances, identifies a plurality of permutations of the plurality of supplemental programs, constructs a plurality of cohorts, each of the cohorts corresponding to a prescribed substance and associated with a permutation, receives adherence data collected with respect to the plurality of permutations associated with the plurality of cohorts; and determines effectiveness of each of the plurality of permutations based on the adherence data.

19 Claims, 43 Drawing Sheets

Related U.S. Application Data continuation-in-part of application No. 13/544,531, filed on Jul. 9, 2012, now abandoned, which is a continuation-in-part of application No. 13/462,486, filed on May 2, 2012, now abandoned.

(60) Provisional application No. 61/635,613, filed on Apr. 19, 2012, provisional application No. 61/611,942, filed on Mar. 16, 2012.

(58) Field of Classification Search
CPC ........ G16H 50/20; G16H 50/30; G16H 10/60; G16H 15/00; G16H 20/10; G16H 70/40
See application file for complete search history.

(56) References Cited

U.S. PATENT DOCUMENTS

| | | |
|---|---|---|
| 5,950,630 A | 9/1999 | Portwood et al. |
| 5,954,641 A | 9/1999 | Kehr et al. |
| 5,966,702 A | 10/1999 | Fresko et al. |
| 6,039,688 A | 3/2000 | Douglas et al. |
| 6,112,182 A | 8/2000 | Akers et al. |
| 6,125,447 A | 9/2000 | Gong |
| 6,240,394 B1 | 5/2001 | Uecker et al. |
| 6,578,003 B1 | 6/2003 | Camarda et al. |
| 6,587,829 B1 | 7/2003 | Camarda et al. |
| 6,859,780 B1 | 2/2005 | Cunningham |
| 7,519,540 B2 | 4/2009 | Mayaud |
| 7,606,723 B2 | 10/2009 | Mayaud |
| 7,679,520 B2 | 3/2010 | Zerhusen et al. |
| 7,729,927 B2 | 6/2010 | Cunningham |
| 7,797,731 B2 | 9/2010 | Bhagavatula et al. |
| 7,925,531 B1 | 4/2011 | Cunningham et al. |
| 7,945,461 B2 | 5/2011 | Sekura |
| 7,996,260 B1 | 8/2011 | Cunningham et al. |
| 8,010,379 B2 | 8/2011 | Tamblyn et al. |
| 8,055,542 B1 | 11/2011 | Cunningham et al. |
| 8,108,226 B2 | 1/2012 | Barrett et al. |
| 8,121,868 B1 | 2/2012 | Grady et al. |
| 8,255,241 B2 | 8/2012 | Cafer |
| 8,301,466 B2 | 10/2012 | Lorsch |
| 8,639,523 B1 | 1/2014 | Pinsonneault |
| 2001/0027403 A1 | 10/2001 | Peterson et al. |
| 2001/0032124 A1 | 10/2001 | Savage et al. |
| 2001/0037216 A1 | 11/2001 | Oscar et al. |
| 2002/0032582 A1 | 3/2002 | Feeney, Jr. et al. |
| 2002/0042725 A1 | 4/2002 | Mayaud |
| 2002/0120471 A1 | 8/2002 | Drazen |
| 2002/0143580 A1 | 10/2002 | Bristol et al. |
| 2002/0147614 A1 | 10/2002 | Doerr et al. |
| 2003/0009367 A1 | 1/2003 | Morrison |
| 2003/0050799 A1 | 3/2003 | Jay et al. |
| 2003/0074234 A1 | 4/2003 | Stasny |
| 2003/0088771 A1 | 5/2003 | Merchen |
| 2003/0177033 A1 | 9/2003 | Park et al. |
| 2003/0212577 A1 | 11/2003 | Nichtberger |
| 2004/0133305 A1 | 7/2004 | Jean-Pierre |
| 2004/0181428 A1 | 9/2004 | Fotsch et al. |
| 2004/0236607 A1 | 11/2004 | Kost et al. |
| 2005/0125257 A1 | 6/2005 | Ziegele et al. |
| 2005/0159977 A1 | 7/2005 | Green et al. |
| 2005/0171817 A1 | 8/2005 | Sachdev et al. |
| 2006/0059017 A1 | 3/2006 | Louik et al. |
| 2006/0184493 A1 | 8/2006 | Shiffman et al. |
| 2006/0235726 A1 | 10/2006 | Paraison et al. |
| 2006/0247968 A1 | 11/2006 | Kadry |
| 2006/0277063 A1 | 12/2006 | Leonardi et al. |
| 2007/0067186 A1 | 3/2007 | Brenner et al. |
| 2007/0078680 A1 | 4/2007 | Wennberg |
| 2007/0168228 A1 | 7/2007 | Lawless |
| 2007/0172424 A1 | 7/2007 | Roser |
| 2007/0174092 A1 | 7/2007 | Lara et al. |
| 2007/0219827 A1 | 9/2007 | Green |
| 2007/0260491 A1 | 11/2007 | Palmer et al. |
| 2007/0288247 A1 | 12/2007 | Mackay |
| 2007/0294112 A1 | 12/2007 | Settimi |
| 2008/0000996 A1 | 1/2008 | Jung et al. |
| 2008/0059228 A1 | 3/2008 | Bossi et al. |
| 2008/0071579 A1 | 3/2008 | Willson et al. |
| 2008/0077430 A1 | 3/2008 | Singer et al. |
| 2008/0126276 A1 | 5/2008 | Williams et al. |
| 2008/0133273 A1 | 6/2008 | Marshall |
| 2008/0215361 A1 | 9/2008 | Nunnari et al. |
| 2008/0228525 A1 | 9/2008 | Weickert et al. |
| 2008/0244453 A1 | 10/2008 | Cafer |
| 2009/0043608 A1 | 2/2009 | Nadas et al. |
| 2009/0089392 A1 | 4/2009 | Fiedotin et al. |
| 2009/0119129 A1 | 5/2009 | Nadas et al. |
| 2009/0164376 A1 | 6/2009 | Guthrie |
| 2009/0222286 A1 | 9/2009 | Elsholz |
| 2009/0240513 A1 | 9/2009 | Angell et al. |
| 2009/0240523 A1 | 9/2009 | Friedlander et al. |
| 2009/0240702 A1 | 9/2009 | Bluth |
| 2009/0287502 A1 | 11/2009 | Roberts et al. |
| 2009/0319291 A1 | 12/2009 | Noordvyk et al. |
| 2009/0326977 A1 | 12/2009 | Cullen et al. |
| 2009/0327363 A1 | 12/2009 | Cullen et al. |
| 2010/0042440 A1 | 2/2010 | Joao |
| 2010/0081118 A1 | 4/2010 | Dixit |
| 2010/0082369 A1 | 4/2010 | Prenelus et al. |
| 2010/0095235 A1 | 4/2010 | Bennett et al. |
| 2010/0100391 A1 | 4/2010 | Daya et al. |
| 2010/0114602 A1 | 5/2010 | Joao et al. |
| 2010/0114605 A1 | 5/2010 | Aull et al. |
| 2010/0114607 A1 | 5/2010 | Kress et al. |
| 2010/0131502 A1 | 5/2010 | Fordham |
| 2010/0153174 A1 | 6/2010 | Angell et al. |
| 2010/0153389 A1 | 6/2010 | Angell et al. |
| 2010/0161353 A1 | 6/2010 | Mayaud |
| 2010/0198619 A1 | 8/2010 | Whelchel et al. |
| 2010/0211407 A1 | 8/2010 | Duke et al. |
| 2010/0228567 A1 | 9/2010 | Wulf |
| 2010/0241445 A1 | 9/2010 | Rago et al. |
| 2010/0274576 A1 | 10/2010 | Young |
| 2010/0285821 A1 | 11/2010 | Smeeding et al. |
| 2011/0015978 A1 | 1/2011 | Welch, Jr. |
| 2011/0093504 A1 | 4/2011 | Butler et al. |
| 2011/0104648 A1 | 5/2011 | Singer et al. |
| 2011/0106556 A1* | 5/2011 | Patel .................... G16H 50/20 705/2 |
| 2011/0119076 A1 | 5/2011 | Dhoble |
| 2011/0125521 A1 | 5/2011 | Dhoble |
| 2011/0131060 A1 | 6/2011 | Schuster et al. |
| 2011/0173047 A1 | 7/2011 | Kelley |
| 2011/0178813 A1 | 7/2011 | Moore |
| 2011/0184753 A1 | 7/2011 | Tripoli |
| 2011/0184755 A1 | 7/2011 | Yamaga et al. |
| 2011/0184756 A1 | 7/2011 | Yamaga et al. |
| 2011/0213622 A1 | 9/2011 | Berman |
| 2011/0238321 A1 | 9/2011 | Slotman |
| 2011/0238435 A1 | 9/2011 | Rapaport et al. |
| 2011/0244919 A1 | 10/2011 | Aller et al. |
| 2011/0245967 A1 | 10/2011 | Shah et al. |
| 2011/0313928 A1 | 12/2011 | Blonchek |
| 2012/0035957 A1 | 2/2012 | Hanz et al. |
| 2012/0109686 A1 | 5/2012 | Higbie et al. |
| 2012/0129139 A1 | 5/2012 | Partovi |
| 2013/0096953 A1 | 4/2013 | Beverly et al. |
| 2013/0166321 A1 | 6/2013 | Harrell |

OTHER PUBLICATIONS

Office Action dated Jan. 4, 2017, in U.S. Appl. No. 13/462,486, 24 pages.
International Preliminary Report on Patentability dated Jan. 26, 2016, in International Application PCT/US2014/048328, 8 pages.
International Preliminary Report on Patentability dated Jan. 26, 2016, in International Application PCT/US2014/048329, 8 pages.
International Preliminary Report on Patentability dated Jan. 26, 2016, in International Application PCT/US2014/048330, 9 pages.
Office Action dated Jan. 22, 2016, in U.S. Appl. No. 13/952,298, 11 pages.

(56) References Cited

OTHER PUBLICATIONS

Office Action dated Oct. 18, 2016, in U.S. Appl. No. 13/952,298, 12 pages.
Office Action dated Apr. 18, 2016, in U.S. Appl. No. 13/952,349, 25 pages.
Office Action dated Aug. 11, 2015, in U.S. Appl. No. 13/952,349, 18 pages.
Office Action dated Jun. 17, 2016, in U.S. Appl. No. 13/462,486, 21 pages.
Office Action dated Mar. 19, 2015, in U.S. Appl. No. 13/462,486, 19 pages.
Office Action dated Mar. 31, 2015, in U.S. Appl. No. 13/544,531, 17 pages.
U.S. Appl. No. 13/565,164, filed Aug. 2, 2012, Pending.
U.S. Appl. No. 13/544,531, filed Jul. 9, 2012, Abandoned.
U.S. Appl. No. 13/462,486, filed May 2, 2012, Abandoned.

* cited by examiner

901 →

Main Stroke Family Practice
Dr. John Smith
100 Main Street
Suite 105
Amytown USA 10001
(215) 111-1234

Patient
John Doe
Rx:
Date:
Super Pharmacy
102 Main Street
Anytown USA 1001
(215) 111-1235

Controlling Your Cholesterol

Cholesterol is a waxy substance, When you have high cholesterol, it builds up in the walls of the blood vessels. This makes the vessels narrower. Blood flow decreases. You are then at greater risk for having a heart attack or stroke.

Good and Bad Cholesterol

LDL is "bad cholesterol." Excess LDL cholesterol will build up in artery walls. This increases your risk for heart disease and stroke.
HDL is "good cholesterol." That's why high levels of HDL can decrease your risk of heart disease and stroke.

Controlling Cholesterol Levels

If your total cholesterol is high, follow the steps below to help lower your total cholesterol level.
- Eat less Unhealthy Fat
- Be Active
- Quit Smoking Remember to pick-up your LIPITOR® prescription at your pharmacy today!

*Taking your mediation is important for treating your health condition.*

902

Cholesterol builds up

Wall of blood vessel blood flow

Join the LIPITOR® FOR YOU Program!

903 →

@asdfdf
$4 CO-PAY CARD

Sign Up & Receive:

✍ LIPITOR $-4 Co-PayCard
✍ Delivery & Pharmacy Services
✍ Tips & Tools

To Register, visit our website at:

| Patient: | john doe [Prescribe] [Change Demographics] | DOB: | 01/01/1985 | Gender: Male | Height: | Weight: | BSA: |
| --- | --- | --- | --- | --- | --- | --- | --- |
| Phone: | (301) 231-4610 (home) | LOV: | No last office visit Visit Today! | | | | |
| Pharmacy: | EPCS Test Pharmacy (O) (E) (555 Fifth St. Rockville MD) (Mail) C. Mixed | | | | | | |
| Formulary: | UNITED HEALTHCARE | | | | | | |

Review Prescription

Please review your prescription for accuracy.

[OK] [Back] [Cancel] [Add to Favorites]

Pharmacy Selected: EPCS Test Pharmacy (555 Fifth St. Rockville MD)

☐ Stop medication on [Apr ▼] [6 ▼] [2012 ▼]

Dr. Runner
123 quincy street, ROCKVILLE, IN 20850
Tel: (301) 244-8399 Fax: (301) 244-8380
NPI: 0346672843 doe, john
Gender: M DOB: 01/01/1985 Tel: (301) 231-9510

Rockville, MD 20850

Rx

Exforge HCT (amlodipine-valsartan-hctz) 5-160-12.5 mg Tablet
Dispense "eight" (sxx) tablet
Sig: Take 2 (two) tablet by mouth every morning as needed
Duration: 30 days
Substitution permitted
Refills: None

FIGURE 14

| Program Cohort Group 1 ||||||
| Cohort Identifier | Provider NPI # | Target Drug | Program Permutation | Current/Max Counter | Cohort Rules |
| --- | --- | --- | --- | --- | --- |
| 1 | 12345 | Lipitor® | 2 | 102/500 | X, Y |
| 1 | 23456 | Lipitor® | 2 | 102/500 | X, Y |
| 1 | 34567 | Lipitor® | 2 | 102/500 | X, Y |
| 2 | 45678 | Lipitor® | 1 | 137/500 | X, Y |
| 2 | 56789 | Lipitor® | 1 | 137/500 | X, Y |
| 2 | 67891 | Lipitor® | 1 | 137/500 | X, Y |
| 3 | 78912 | Lipitor® | 3 | 125/500 | X, Y |
| 3 | 89123 | Lipitor® | 3 | 125/500 | X, Y |
| 3 | 91234 | Lipitor® | 3 | 125/500 | X, Y |
| 4 | 54321 | Lipitor® | 4 | 119/500 | X, Y |
| 4 | 65432 | Lipitor® | 4 | 119/500 | X, Y |
| 4 | 76543 | Lipitor® | 4 | 119/500 | X, Y |

FIGURE 34

INFORMATION SYSTEM FOR PHYSICIANS

CROSS-REFERENCE TO RELATED APPLICATIONS

The present application is a continuation of U.S. non-provisional patent application Ser. No. 13/565,164, filed Aug. 2, 2012, which is a continuation-in-part of U.S. non-provisional patent application Ser. No. 13/544,531, filed Jul. 9, 2012, which in turn is a continuation-in-part of U.S. Non-provisional patent application Ser. No. 13/462,486, filed May 2, 2012, which in turn claims the benefit of U.S. provisional patent application No. 61/635,613, filed Apr. 19, 2012, and U.S. provisional patent application No. 61/611,942, filed Mar. 16, 2012, the entireties of which are hereby incorporated by reference.

FIELD OF THE INVENTION

The present invention relates generally to systems and methods for supplementing patient and provider interactions, and specifically to systems and methods for electronically enhancing patient and provider interactions using supplemental programs in response to an electronic prescription request to increase patient adherence.

BACKGROUND OF THE INVENTION

Poor patient adherence is a major concern within the health care industry. After visiting their health care provider and receiving at least one prescription for substances, many patients fail to maintain a level of dedication and adherence to their prescribed substances. This results in increased costs to all parties involved in the health care industry, including, but not limited to the patient, the health care provider, the pharmacies, the pharmaceutical companies, and the health insurance companies. There are currently many methods used with the goal of increasing patient adherence, such as, the distribution of patient educational material, coupons, and patient reminder services. However, there still remains a need for a system that can better utilize these methods to increase patient adherence.

One important element to increasing patient adherence is good health care provider-patient interaction. Because this interaction takes place at the point-of-care while the patient is thinking about their current physical state, this interaction is crucial for facilitating patient health, awareness, and adherence. However, there is currently not a system that allows for a health care provider to be fully aware of whether their patients are adhering to their prescriptions, while the patients are at the point-of-care. Further, the current methods of increasing patient adherence through educational and financial incentives require the health care provider to not only know whether or not their patients are adhering to their prescribed substances, but also requires the health care provider to have the specific education material and coupons/discounts for each patient's specific diagnoses and prescribed substances at the point-of-care. This is overly burdensome and practically impossible for a health care provider who has patients with a wide variety of health care needs. Therefore, there is also a need for a system that can more easily and efficiently distribute patient educational materials, coupons, and other supplemental programs at the point-of-care.

Additionally, pharmaceutical companies are restricted in the number of coupons and other incentives they may distribute. Currently, the coupons and other incentives are distributed to patients without taking into consideration whether the patient receiving the coupon or other incentive needs or will be incentivized by them. Therefore, there also remains a need for a system that can aid pharmaceutical companies in distributing coupons and other incentives to their customers in a more efficient manner.

The systems and methods described herein help to fill the needs and solve the issues described above.

According to one embodiment, the present invention is directed to a method of provisioning a combined educational coupon, the method comprising: a) receiving, on a computer apparatus, electronic prescription data for a prescribed substance for a patient; b) the computer apparatus determining educational data relating to the prescribed substance and coupon data relating to the prescribed substance; and c) the computer apparatus generating a single data file comprising the educational data relating to the prescribed substance and the coupon data relating to the prescribed substance.

According to another embodiment, the present invention is directed to a non-transitory computer-readable storage medium encoded with instructions which, when executed on a processor, perform a method comprising: a) receiving data relating to an electronic prescription of a prescribed substance for a patient; b) searching one or more databases for educational data relating to the prescribed substance and coupon data relating to the prescribed substance; c) determining educational data relating to the prescribed substance and coupon data relating to the prescribed substance; d) retrieving from the one or more databases the educational data relating to the prescribed substance and the coupon data relating to the prescribed substance; and e) generating a single data file comprising the educational data relating to the prescribed substance and the coupon data relating to the prescribed substance.

According to yet another embodiment, the present invention is directed to a computer system for electronically generating educational coupons for a prescribed substance, the computer system comprising: a processor; a storage device; a network interface; and instructions residing on the storage unit, which when executed by the processor, causes the processor to: a) receive electronic prescription data for a prescribed substance for a patient: b) determine educational data relating to the prescribed substance and coupon data relating to the prescribed substance; and c) generate a single data file comprising the educational data relating to the prescribed substance and the coupon data relating to the prescribed substance.

According to another embodiment, the present invention is directed to a method of supplementing an electronic prescription issued by a health care provider, the method comprising: a) receiving, on a computer apparatus, electronic prescription data generated by a health care provider for a patient for a prescribed substance: b) the computer apparatus determining, from a plurality of available supplemental programs stored on one or more databases, supplemental programs for which the patient is eligible based on the electronic prescription data; c) presenting to the health care provider, in a display device, a list of the eligible supplemental programs, each of the eligible supplemental programs being selectable and de-selectable by the health care provider in the display device; and d) the computer apparatus activating each supplemental program from the plurality of available supplemental programs that have been selected and confirmed by the health care provider in the display device; and wherein one of the activated supplemental programs is a coupon service, and wherein step d) further comprises retrieving coupon data relating to the prescribed substance from the one or more databases, and provisioning a coupon based on the coupon data to the patient; and wherein one of the activated supplemental programs is a prescribed substance education service, and wherein step d) further comprises retrieving education content relating to the prescribed substance from the one or more databases, and transmitting said education content to the patient, said coupon data being integrated into the education content to create a combined educational coupon.

According to another embodiment, the present invention is directed to a method of providing educational materials to a patient, the method comprising: a) receiving, on a computer apparatus, electronic prescription data for a prescribed substance for a patient, said electronic prescription data including a diagnostic code; b) searching one or more databases, using the computer apparatus, to determine: (1) general educational data relating to the prescribed substance and independent of the diagnostic code; and (2) specific educational data relating to the prescribed substance and based on the diagnostic code; and c) presenting to a health care provider, in a display device, a list of the general educational data and the specific educational data determined in step b) for provisioning to the patient.

According to another embodiment, the present invention is directed to a non-transitory computer-readable storage medium encoded with instructions which, when executed on a processor, perform a method comprising: a) receiving electronic prescription data for a prescribed substance for a patient, said electronic prescription data including a diagnostic code; b) searching one or more databases to determine: (1) general educational data relating to the prescribed substance independent of the diagnostic code; and (2) specific educational data relating to the prescribed substance based on the diagnostic code; and c) presenting to a health care provider, in a display device, a list of the general educational data and the specific educational data determined in step b) for provisioning to the patient.

According to yet another embodiment, the present invention is directed to a computer system for electronically generating coupons for a prescribed substance, the computer system comprising: a processor; a storage device; a network interface; and instructions residing on the storage unit, which when executed by the processor, causes the processor to: a) receive electronic prescription data for a prescribed substance for a patient, said electronic prescription data including a diagnostic code; b) search one or more databases to determine: (1) general educational data relating to the prescribed substance independent of the diagnostic code; and (2) specific educational data relating to the prescribed substance based on the diagnostic code; and c) present to a health care provider, in a display device, a list of the general educational data and the specific educational data determined in step b) for provisioning to the patient.

BRIEF DESCRIPTION OF THE DRAWINGS

The present invention will become more fully understood from the detailed description and the accompanying drawings, wherein:

FIG. 9 is an illustration of a combined educational material and coupon document according to one embodiment of the present invention;

Figure 12:
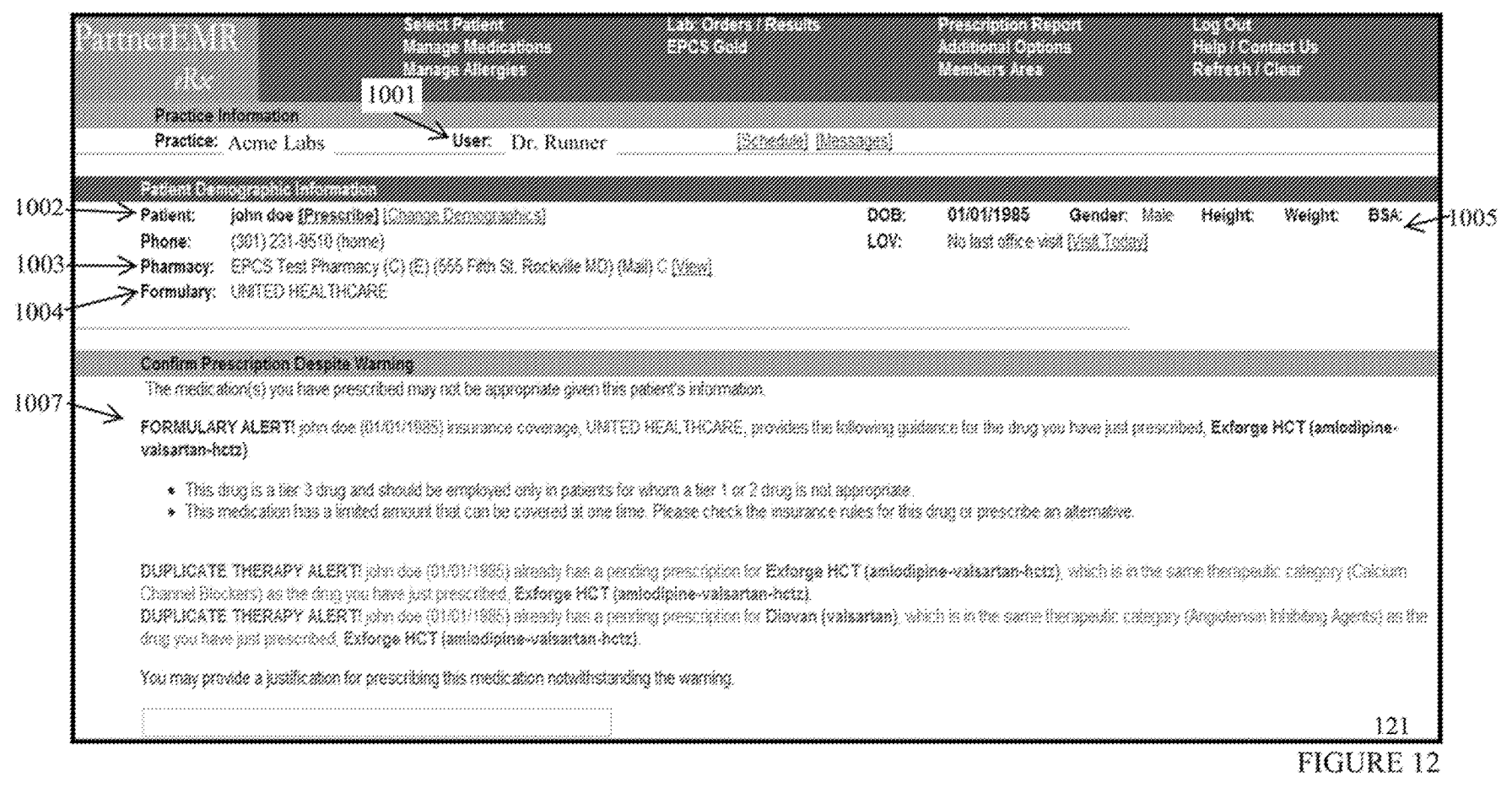
Figure 13:
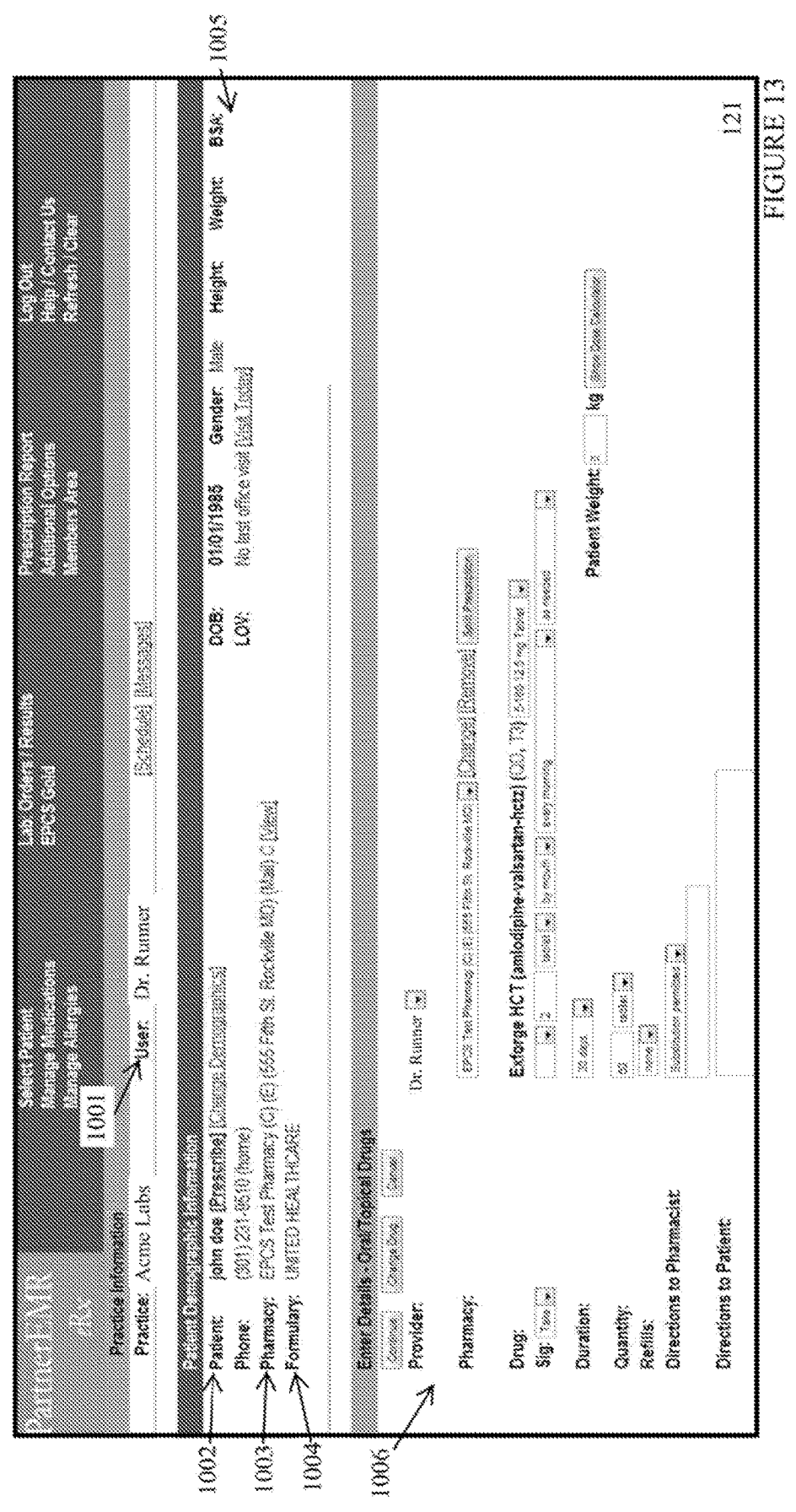

FIGS. 10-15 are screen shots of graphical user interfaces used for supplementing patient and provider interactions to increase patient adherence according to one embodiment of the present invention;

FIG. 34 is a schematic diagram of a cohort relation table according to one embodiment of the present invention;

DETAILED DESCRIPTION OF THE INVENTION

The following description of the preferred embodiment(s) is merely exemplary in nature and is in no way intended to limit the invention, its application, or uses.

System Overview

Figure 1:
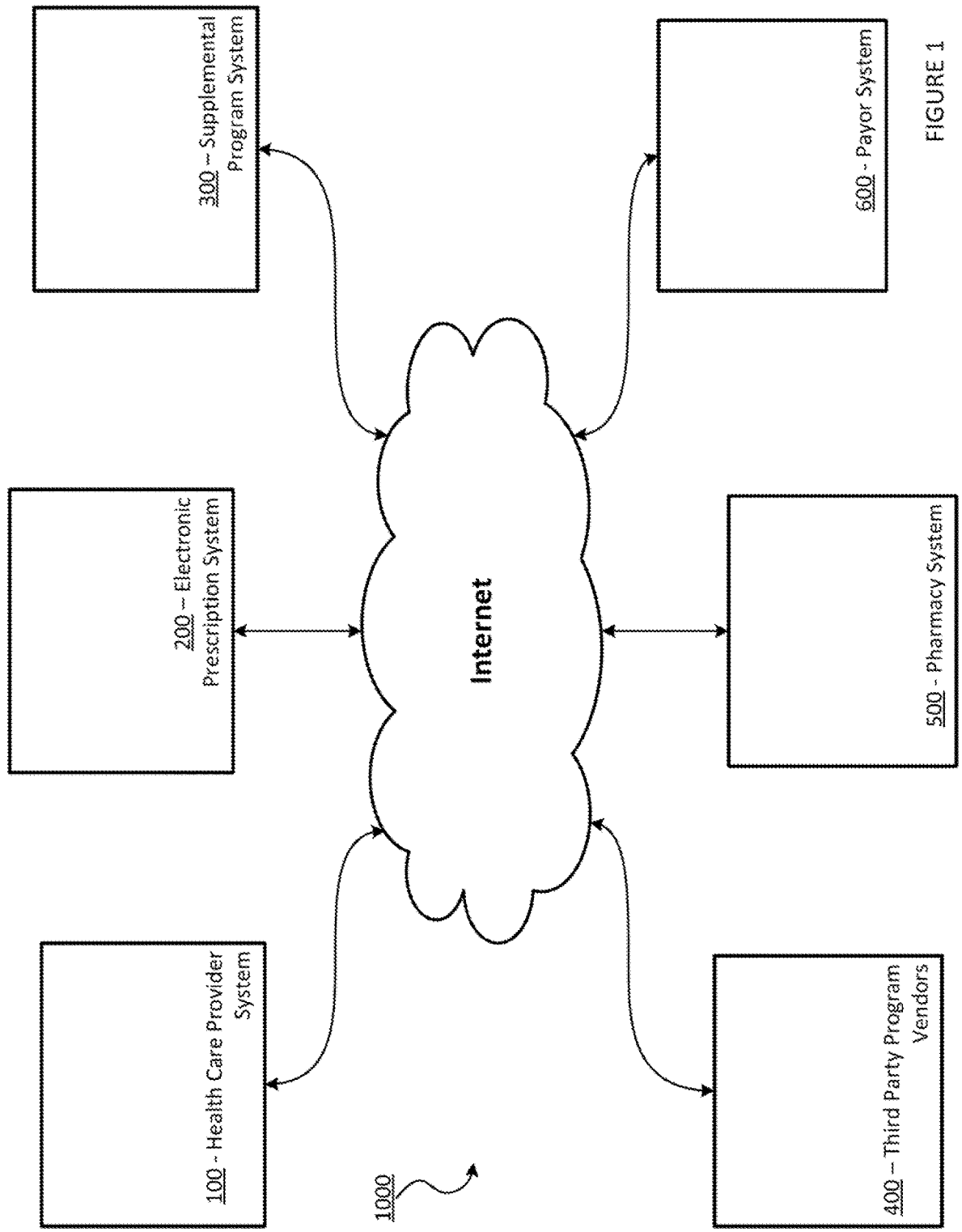
FIG. 1 is a schematic diagram of a system for supplementing patient and provider interactions to increase patient adherence according to one embodiment of the present invention.

Referring to FIG. 1, a schematic diagram of a system 1000 for supplementing patient and provider interactions to increase patient adherence according to one embodiment of the present invention is illustrated. Generally, the system 1000 comprises a health care provider (HCP) system 100, an electronic prescription (EP) system 200, a supplemental program (SP) system 300, at least one third party program vendor 400, a pharmacy system 500, and a payor system 600 all in operable communication with one another to form a wide area network (WAN).

As exemplified by FIG. 1, the components of the system 1000 are in operable communication via the internet. However, the invention is not so limited and other electronic communication means may be utilized, such as a satellite network, a cellular network, a common carrier network(s), Wi-Fi, WiMAX or any combination thereof. Further, it should be noted that operable communication includes any means of electronic communication, such as but not limited to wired and wireless electronic communication, in which data can be transmitted and received between the systems and modules of the system 1000. Moreover, it should also be noted that operable communication includes both direct and indirect communication, as well as bi-directional communication between the systems and modules of the system 1000.

As discussed in more detail below, the system 1000 of the present invention may be configured in other ways. Therefore, it should be noted that the invention is not limited only to those configuration explicitly described herein and, in alternate embodiments the system 1000 may take on other configurations and/or layouts. For instance, any of the systems and/or modules of the system 1000 may be connected via a local area network (LAN). For example, according to one embodiment of the present invention, the EP system 200 and the SP system 300 reside on the same LAN, and therefore, may communicate via Ethernet and/or Wi-Fi over a LAN.

Figure 2:
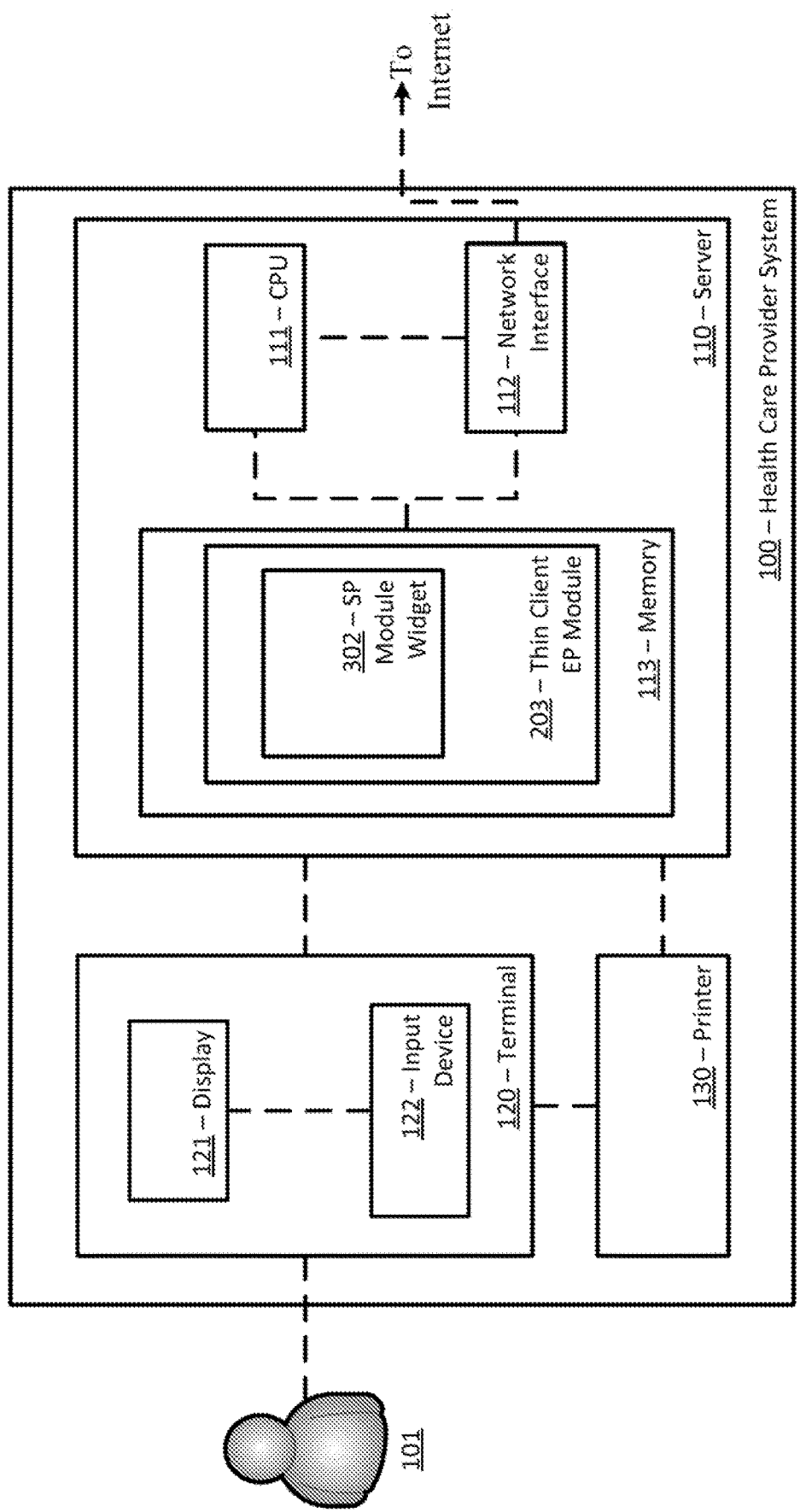
FIG. 2 is a schematic diagram of a health care provider system for supplementing patient and provider interactions to increase patient adherence according to one embodiment of the present invention.

Referring to FIG. 2, a schematic diagram of an HCP system 100 according to one embodiment of the present invention is illustrated. The HCP system 100 comprises a server 110, a terminal 120, and a printer 130 in operable communication. Further, as discussed in more detail below, the HCP system 100 may also be said to comprise at least one health care provider 101. Although exemplified as comprising the above components, the HCP system 200 may comprise any number, more or less, of the components listed above. For example, a particular HCP system 100 may comprises a plurality of providers 101, a plurality of servers 110, a plurality of terminals 120, and/or a plurality of printers 130.

Generally, the HCP system 100 is an institution or organization that provides general and/or specific health care for those in need. For example, an HCP system 100 may be an entire hospital or health care system, a specialized practice group within a larger hospital or health care system, a private general practice, or a private specialized practice. The health care provider 101 may be a medical doctor, a nurse practitioner, or a staff administrator who is authorized to issue prescriptions. As noted above, the HCP system 100 may comprise any number of providers 101, and a particular provider 101 may be associated with more than one HCP system 100 at any given time.

The server 110 of the HCP system 100 comprises a properly programmed processor (or central processing unit (CPU)) 111, a network interface 112, and a memory device 113 all in operable communication. It should be noted the processor 110 may be considered the processor of the HCP system 100. Further, although exemplified as a single server 110, the invention is not so limited and in alternate embodiments the HCP system 100 may comprise any number of servers 110. Additionally, although not exemplified, it should be understood that the processor 111 can have integrated memory. The network interface 112 connects the server 110 to the over systems and modules of the system 1000 via the internet. The properly programmed processor 111 of the HCP system 100 effectuates the performing of the processes and functions described below, including but not limited to, the storage of data to the memory 113 of the HCP system 100, the performance of the processes and functions of a thin-client portion of an electronic prescription (EP) module 203 and a supplemental program (SP) module widget 302, and the transfer (transmission and receipt) of data from HCP system 100 to the other systems and modules of the system 1000.

In the exemplified embodiment, the memory 113 comprises the thin-client portion of the EP module 203 and the SP module widget 302, both of which are described in more detail below. Although exemplified as a single memory unit, it should be noted that the memory 113 may comprise any number of databases used to store data, modules, or other information. For example, the memory may be used to store provider information, patient information, prescribed substance information, and appropriate software to allow the provider 101 to interact with the thin-client portion of the EP module 203 and the SP module widget 302.

Although exemplified as part of the memory 113, in other embodiments the thin-client portion of the EP module 203 may reside elsewhere on the HCP system 100 or on another system altogether. Further, in the exemplified embodiment the SP module widget 302 is integrated into the thin-client portion of the EP module 203. However, it should be noted that the invention is not so limited and in alternate embodiments, any portion of the SP module may be integrated into any portion of the EP module. Further, in one embodiment of the present invention, the SP module is not integrated with the EP module, but is rather a completely separate module altogether.

The terminal 120 of the HCP system 100 may be a personal computer (PC) or a mobile electronic unit. Each terminal 120 of the HCP system 100 comprises a properly programmed processor (not shown), a memory device (not shown), a power supply (not shown), a video card (not shown), a display device 121, firmware (not shown), software (not shown), a network interface (not shown) and a user input device 122 (e.g., a keyboard, mouse and/or touch screen). Although not exemplified, it should be understood that the processor of the terminal 120 can have integrated memory. The properly programmed processor of the terminal 120 is configured to effectuate the processes and functions described below, including, but not limited to the effectuation of the graphical user interfaces (GUI) for display on the display device 121 of the terminal 120 for the provider 101 and the transmission of user inputs from the provider 101 via the input device 122 to the other systems and modules of the system 1000.

As discussed in more detail below, after the provider 101 generates a prescription for a substance using the thin-client portion of the EP module 203, the electronic prescription is transmitted by the HCP system 100 to the pharmacy system 500 for processing. Further, as also discussed in more detail below, at any point during the prescription writing processes using the EP module 203, the SP module widget 302 may receive electronic prescription data relating to the electronic prescription and transmits the electronic prescription data to the to the SP system 300 for further processing.

Figure 3:
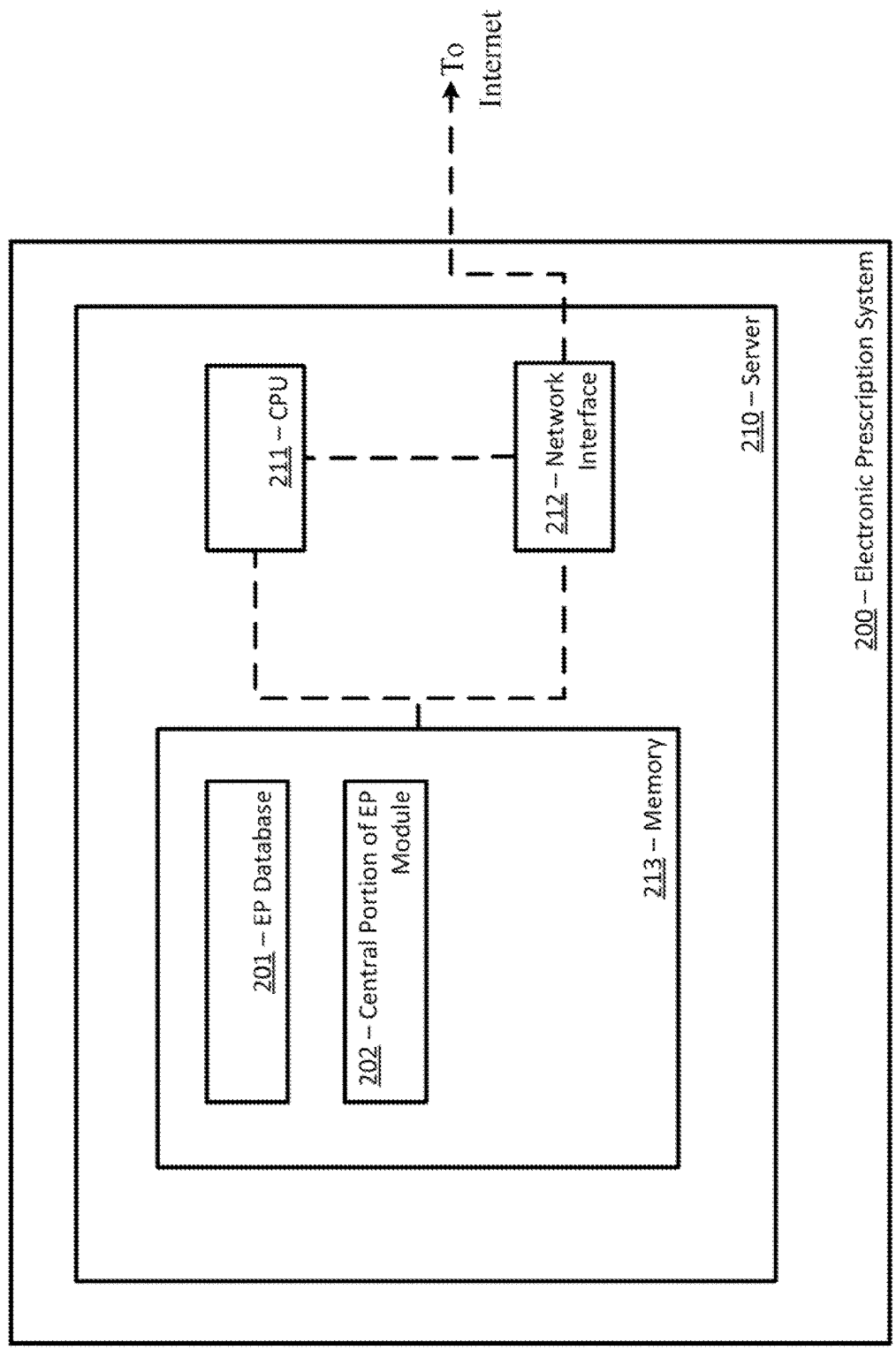
FIG. 3 is a schematic diagram of an electronic prescription system for supplementing patient and provider interactions to increase patient adherence according to one embodiment of the present invention.

Referring to FIG. 3, a schematic diagram of an EP system 200 according to one embodiment of the present invention is illustrated. Generally, the EP system 200 comprises a server 210 which comprises a properly programmed processor (CPU) 211, a network interface 212, and a memory unit 213 in operable communication. It should be noted that the processor 211 may be considered the processor of the EP system 200. Further, although exemplified as a single server 210, the invention is not so limited and in alternate embodiments the EP system 200 may comprise any number of servers 210. Additionally, although not exemplified, it should be understood that the processor 211 can have integrated memory. The network interface 212 connects the server 210 to the over systems and modules of the system 1000 via the internet.

As discussed in more detail below, the processor 211 of the EP system 200 effectuates the performance of the processes and functions described herein, including but not limited to the performance of the processes carried out by the central portion of the EP module 202, the storage of data to the EP database 201, and the transfer of data between the EP system 200 and the other systems and modules of the system 1000.

The memory 213 of the EP system 200 comprises an electronic prescription (EP) database 201 and a central portion of the electronic prescription (EP) module 202. The EP database 201 stores information relating to electronic prescriptions that are generated using and effectuated by the EP module, such as, but not limited to, provider data, patient data, prescribed substance data, payor data, and patient medication history data. Further, although exemplified as a single memory unit, it should be noted that the memory 213 may comprise any number of databases used to store data, modules, or other information.

Generally, the EP module is one or more computer programs configured to allow a provider 101 to generate and transmit electronic prescriptions to the pharmacy system 500. In embodiments where the EP module comprises a central portion 202 and a client portion 203, the central portion 202 is configured to do most of the heavy processing of the EP module. Further, in such embodiments, the client portion 203 is a thin-client portion that does light processing and generates/displays user interfaces for the provider 101 on the display device 121 of their terminal 120.

As used herein, the central portion 202 and the thin-client portion 203 of the EP module may be collectively defined as the "EP module." Although exemplified as comprising a thin-client portion 203 that resides within the memory 113 of the HCP system 100 and a central portion 202 that resides within the memory 213 of the EP system 200, the EP module is not so limited. In alternate embodiments, the central portion 202 of the EP module may reside elsewhere on the system 1000 or be combined with the thin-client portion 203 of the EP module and reside on any of the systems of the system 1000. In embodiments where the central portion 202 and the thin-client portion 203 are combined, the provider 101 may access the EP module via a web interface (portal) or an applicant user interface using their terminal 120. One non-limiting example of an EP module is Rcopia® by DrFirst®.

Figure 4:
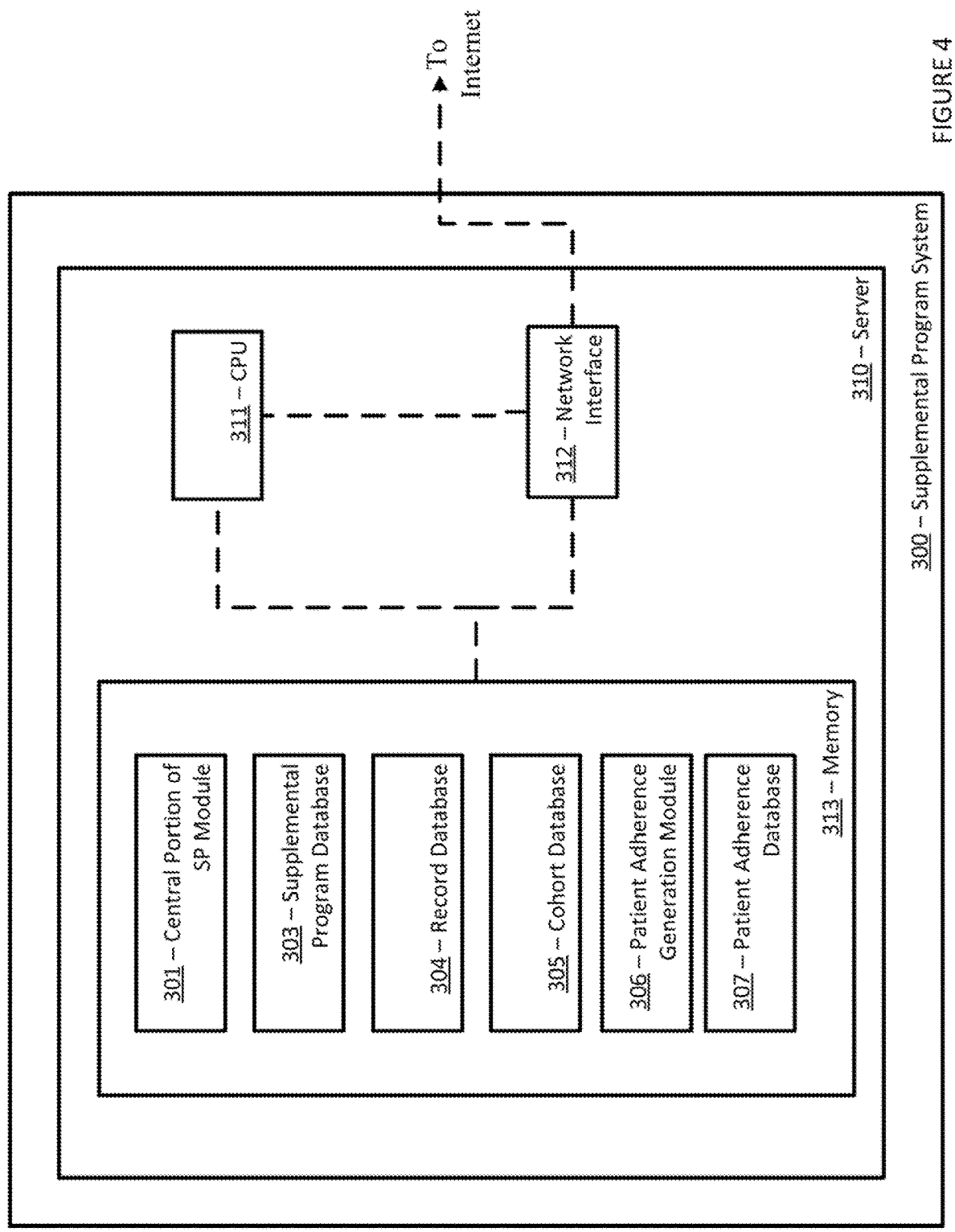
FIG. 4 is a schematic diagram of a supplemental program system for supplementing patient and provider interactions to increase patient adherence according to one embodiment of the present invention.

Referring to FIG. 4, a schematic diagram of a SP system 300 according to one embodiment of the present invention is illustrated. Generally, the SP system 300 comprises a server 310 which comprises a properly programmed processor (CPU) 311, a network interface 312, and a memory unit 313 in operable communication. It should be noted that the server 310 may be considered the supplemental program server and the processor 311 may be considered the processor of the SP system 300. Further, although exemplified as a single server 310, the invention is not so limited and alternate embodiments the SP system 300 may comprise any number of servers 310. Additionally, although not exemplified, it should be understood that the processor 311 can have integrated memory. The network interface 312 connects the server 310 to the over systems and modules of the system 1000 via the internet.

As discussed in more detail below, the processor 311 of the SP system 300 effectuates the performance of the processes and functions described herein, including but not limited to the performance of the processes carried out by the central portion 301 of a supplemental program (SP) module (e.g., the determination of eligibility performed by the SP module, the transfer of content to a patient or the HCP system 100, the enrollment of a patient into a service, etc.), the storage of data to a supplemental program database 303 and a record database 304, and the transfer of data between the SP system 300 and the other systems and modules of the system 1000.

The memory 313 of the SP system 300 comprises a central portion of the SP module 301, a supplemental program database 303, and a records database 304. Although exemplified as a single memory unit, it should be noted that the memory 113 may comprise any number of databases used to store data, modules, or other information. As used herein, the central portion 301 and the widget 302 of the SP module may be collectively defined as the "SP module."

Generally, the SP module is one or more computer programs configured to determine, from a plurality of available supplemental programs, specific supplemental programs for which a patient is eligible. Further, as also discussed in more detail below, the SP module is configured to, among other things: (1) receive electronic prescription data generated by a provider 101 for a patient for a prescribed substance from either the HCP system 100, the EP module, or the EP system 200; (2) retrieve patient data, prescribed substance data, provider data, and/or payor data from one or more databases of the system 1000; (3) determine, from a plurality of available supplemental programs, specific supplemental programs for which a patient is eligible; (4) determine delivery modes that are available for each supplemental program in which the patient is eligible; (5) generate graphical user interfaces (GUIs) that are displayed to the provider 101 on the display device 121 of the HCP system 100; (6) receive inputs from the provider 101 via the input device 122 of the HCP system 100; (7) generate an activation signal for each supplemental program that is selected by the provider 101; (8) receive the activation signal from the HCP system 100; (9) activate supplemental programs that are selected and confirmed by the provider 101; (10) tailor content associated with an activated supplemental program for a specific delivery mode; and (11) deliver the content associated with the activated supplemental program to the patient.

As also discussed in more detail below, the central portion 301 of the SP module determines eligible supplemental programs, out of a plurality of available supplemental programs, for a patient based on at least electronic prescription data and the rules of each available supplemental programs. Although not exemplified, the central portion 301 of the SP module comprises a rules engine that determines the eligibility of each of the available supplemental programs for a patient being prescribed a particular substance. Further, the central portion 301 of the SP module also comprises agents that reach out to the third party content providers 400 to retrieve content relating to the plurality of supplemental programs. However, the invention is not so limited and in one embodiment, the central portion 301 of the SP module does not comprise the rules engine, but rather just transmits at least the electronic prescription data to the third party content providers 400, which in turn determines the eligibility of each of the available supplemental programs.

In the exemplified embodiments, the central portion 301 does most of the heavy processing of the SP module, while the SP widget 302 routes data to the central portion 301 and provides an interface for the provider 101 to access the SP module. Although exemplified as comprising a SP module widget 302 that resides within the memory 113 of the HCP system 100 (and more specifically, a SP module widget 302 that is integrated into the EP module) and a central portion 301 that resides within the memory 313 of the SP system 300, the SP module is not so limited. In alternate embodiments of the present invention, the central portion 301 and/or the SP widget 302 may reside elsewhere on the system 1000, or the central portion 301 may be combined with the SP module widget 302 and the combined SP module may reside on any system or module of the system 1000. Further, as described herein, it should be understood that any of the processes or functions performed by either the central portion 301 or the SP widget 302 may be performed partially or wholly by the other portion of the SP module in an alternate embodiment of the present invention.

The supplemental program database 303 stores general supplemental program data, including, but not limited to the names of a plurality of available supplemental programs, general information relating to each of the plurality of available supplemental programs, and the rules of each of the available supplemental program. As discussed in more detail below, according to one embodiment of the present invention, a supplemental program is a document or service that is activated for a patient based on the defined rules of the supplemental program. Further, according to one embodiment of the present invention, each supplemental program is designed to increase the patient's adherence to a prescribed substance.

As also discussed in more detail below, the rules of each supplemental program dictate which patients are eligible for the supplemental program. Generally, each rule may be based on, among other things, a substance currently being prescribed to the patient, the patient's medical history, information relating to the provider, and/or information relating to the patient's payor or health insurance company. According to one embodiment of the present invention, the rules of the supplemental programs are defined by a combination of an administrator of the SP system 300 and one or more pharmaceutical companies. However, the invention is not so limited, and in alternate embodiments the rules may be defined by any combination of the administrator of the SP system 300, the pharmaceutical companies, and/or the third party program vendors 400.

It should be noted that although exemplified as residing entirely in the memory 313 of the SP system 300, in alternate embodiments, the supplemental program database 303 may reside entirely on another system of the system 1000 or be broken up and reside partially on two or more of the systems of the system 1000. Specifically, in one alternate embodiment the supplemental program database 303 resides entirely on the HCP system 100, while in another alternate embodiment the supplemental program database 303 resides entirely on the EP system 200.

Further, as also discussed in more detail below, in one embodiment of the present invention the supplemental program database 303 may comprise the underlying supplemental programs themselves. In such embodiments, the SP module does not have to reach out to the third party content providers 400 to retrieve content relating to a supplemental program or to enroll a patient in a supplemental program.

The record database 304 stores information relating to the parties and the processes involved in supplementing an electronic prescription, such as, but not limited to, patient data, prescribed substance data, provider data, payor data, and patient medication history data. Further, the record database 304 may further store provider preference data and patient preference data. It should be noted that although exemplified as residing entirely on the SP system 300, in alternate embodiments, the record database 304 may reside entirely on another system of the system 1000 or be broken up and reside partially on two or more of the systems of the system 1000. Specifically, in one alternate embodiment the record database 304 resides entirely on the HCP system 100, while in another alternate embodiment the record database 304 resides entirely on the EP system 200.

Finally, according to one embodiment of the present invention, the SP system 300 further comprises an administrator. The administrator is an individual (or group of individuals) who has access to the databases, modules, and engines of the SP system 300, and may configured to databases, modules, and engines as they see fit. For example, in some embodiments of the present invention, the administrator may configure the settings of the SP module (both central portion 301 and SP widget 302), may configure the data stored in the one or more databases of the SP system 300, may configure the rules of the available supplemental programs, and/or may configure the rules engine of the SP module. Therefore, the administrator of the SP system 300 has the ability to access and control the processes and functions of all of the components of the SP system 300.

Figure 5:
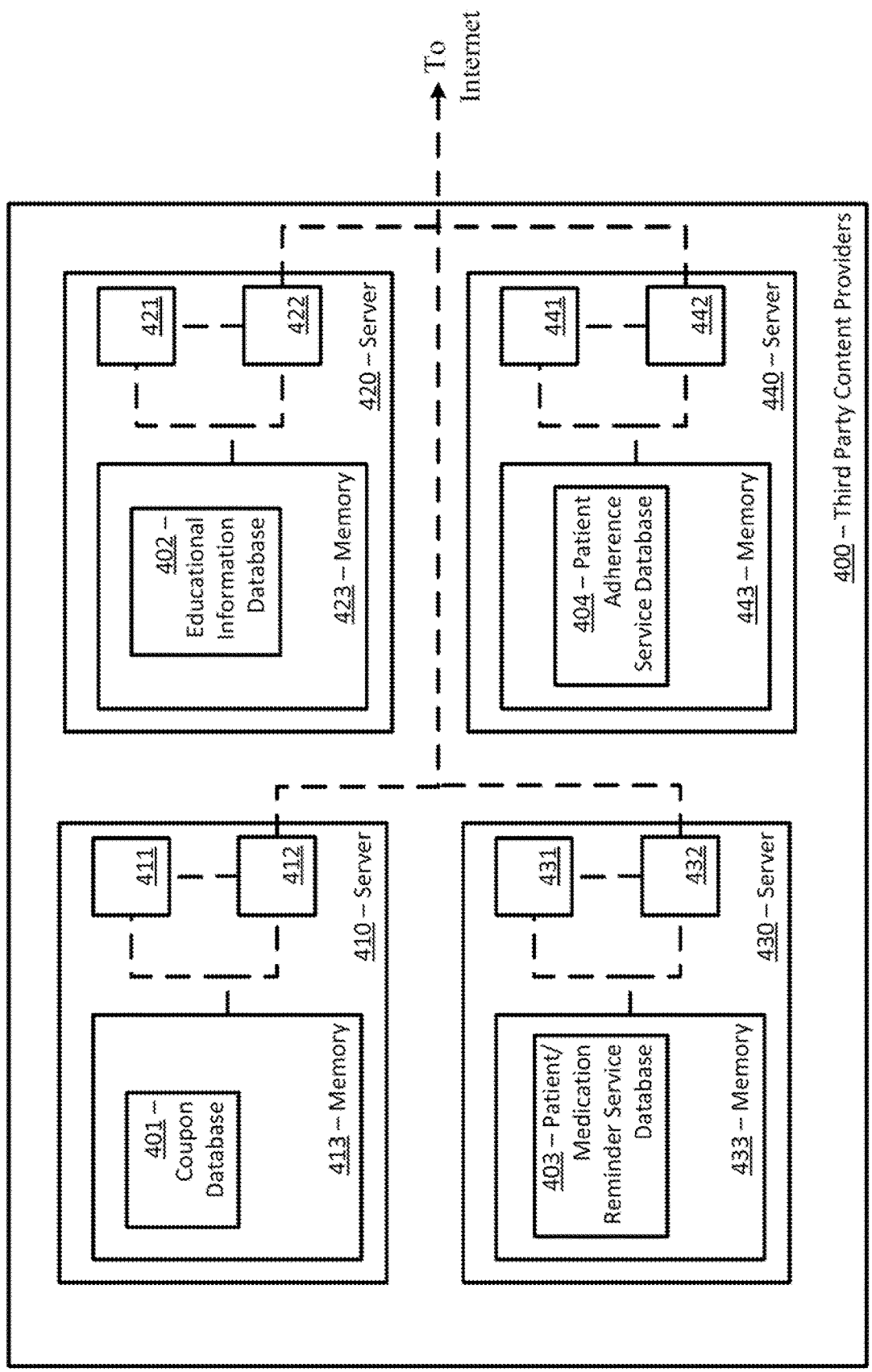
FIG. 5 is a schematic diagram of a plurality of third party program vendors for supplementing patient and provider interactions to increase patient adherence according to one embodiment of the present invention.

Referring to FIG. 5, a schematic diagram of a plurality of third party content providers 400 according to one embodiment of the present invention is illustrated. Generally, the present invention is not limited to any specific number of third party content providers 400. Therefore, although four third party content providers (410, 420, 430, 440) are illustrated in FIG. 5, the present invention may comprise more or less than four third party content providers 400. For example, in an alternate embodiment of the present invention, one or more of the third party content providers 400 may be combined.

Each third party content provider 400 comprises a server 410, 420, 430, 440 which comprises a properly programmed processor (CPU) 411, 421, 431, 441, a network interface 412, 422, 432, 442, and a memory unit 413, 423, 433, 443 in operable communication. Although each third party content provider 400 is exemplified as comprising a single server 410 (or 420, 430, 440), the invention is not so limited and in alternate embodiments any of the third party content provider 400 may comprise any number of servers. Additionally, although not exemplified, it should be understood that the processors 411, 421, 431, 441 can have integrated memory. Finally, the network interfaces 412, 422, 432, 442 connects their respective server 410, 420, 430, 440 to the over systems and modules of the system 1000 via the Internet.

As discussed in more detail below, the processors 411, 421, 431, 441 of each third party content providers 400 effectuates the performance of the processes and functions described herein, including but not limited to the storage of data to the databases 401, 402, 403, and 404, the transfer of content to a patient, the enrollment of a patient into a service, and the transfer of data between each third party content providers 400 and the other systems (specifically the SP system 300) of the system 1000.

The memory unit 413 comprises a coupon database 401, the memory unit 423 comprises an educational information database 402, the memory unit 433 comprises a patient/medication reminder service database 403, and the memory unit 443 comprises a patient adherence service database 404. Although exemplified as a single memory unit, it should be noted that any of the memory units 413, 423, 433, 443 may comprise any number of databases used to store data, modules, or other information.

The coupon database 401 stores supplemental program coupon data relating to a plurality of different coupon documents and coupon services for a plurality of substances that may be prescribed to a patient. The supplemental program coupon data may include the amount of a coupon, the rules relating to the eligibility of a coupon or a coupon service, the delivery modes of the coupon or coupon service, and other information relating to a particular coupon or coupon service. Further, it should be noted that a coupon may be, but is not limited to, a discount for prescribed substances, a rebate for prescribed substances, or a voucher for a free trial of prescribed substances.

The educational information database 402 stores supplemental program educational data relating to a plurality of different educational documents for a plurality of different substances and diseases states for which a patient may be prescribed or diagnosed. The supplemental program educational data may include general educational documents relating to a plurality of different substances or disease states, specific educational documents relating to a plurality of different substances or disease states, general educational services that relate to a plurality of different substances or disease states, specific educational services that relate to a plurality of different substances or disease states, and the rules relating to the eligibility of the documents and services listed above.

The patient/medication reminder service database 403 stores supplemental program reminder data relating to a plurality of different patient reminder services and substance (or medication) reminder services. The supplemental program reminder data may include information relating to appointment reminder services for a patient, prescription filling reminder services for a patient, refill reminder services for a patient, and the rides relating to the eligibility of the services listed above.

The patient adherence service database 404 stores supplemental program adherence data relating to a plurality of adherence services for patients. The supplemental program adherence data may include information relating to a variety of different adherence programs and services for patients, including the rules relating to the eligibility of the services.

Figure 6:
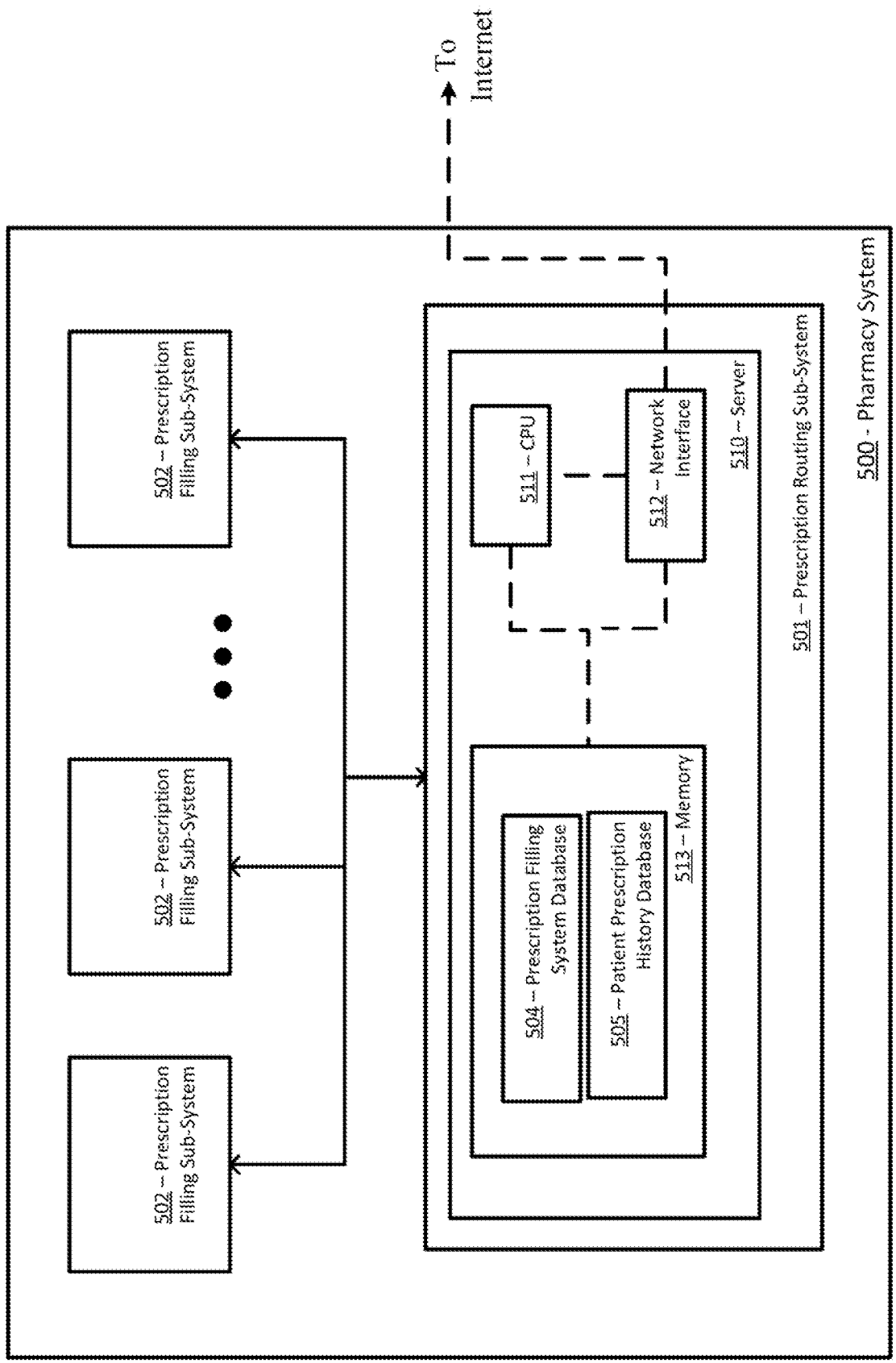
FIG. 6 is a schematic diagram of a pharmacy system for supplementing patient and provider interactions to increase patient adherence according to one embodiment of the present invention.

Referring to FIG. 6, a schematic diagram of a pharmacy system 500 according to one embodiment of the present invention is illustrated. In the exemplified embodiment, the pharmacy system 500 comprises a prescription routing sub-system 501 and at least one prescription filling sub-system 502, all in operable communication with one another. Generally, the prescription routing sub-system 501 is configured to electronically receive a prescription for a substance from the HCP system 100 or the EP system 200 and route the prescription to a prescription filling sub-system 502.

The prescription routing sub-system 501 comprises a server 510 that comprises a properly programmed processor 511, a network interface 512, and a memory device 513 in operable communication. Although not exemplified, each of the prescription filling sub-systems 502 comprises a properly programmed processor, a network interface, and a memory unit. Although exemplified as a single server 510, the invention is not so limited and in alternate embodiments the prescription routing sub-system 501 may comprise any number of servers 510. Additionally, although not exemplified, it should be understood that the processor 511 can have integrated memory. The network interface 512 connects the server 510 to the over systems and modules of the system 1000 via the internet. The processor 511 of the pharmacy system 500 effectuates the processes and functions described herein, including but not limited to, the reception of prescription data from the EP module, the transfer of prescription history information to the SP module, and the transfer of data between the pharmacy system 500 and the other systems and modules of the system 1000.

In the exemplified embodiment, the memory 513 of the prescription routing sub-system 501 comprises a prescription filling system database 504 and a patient prescription history database 505. The prescription filling system database 504 stores the names, addresses and other information relating to each of the prescription filling sub-system(s) 502. The patient prescription history database 505 stores information relating to previous prescriptions routed by the pharmacy system 500 for patients.

The prescription filling sub-system 502 is a system that fills the prescribed substance for an end user. For example, prescription filling sub-system 502 may be a local pharmacy used by a patient.

Figure 7:
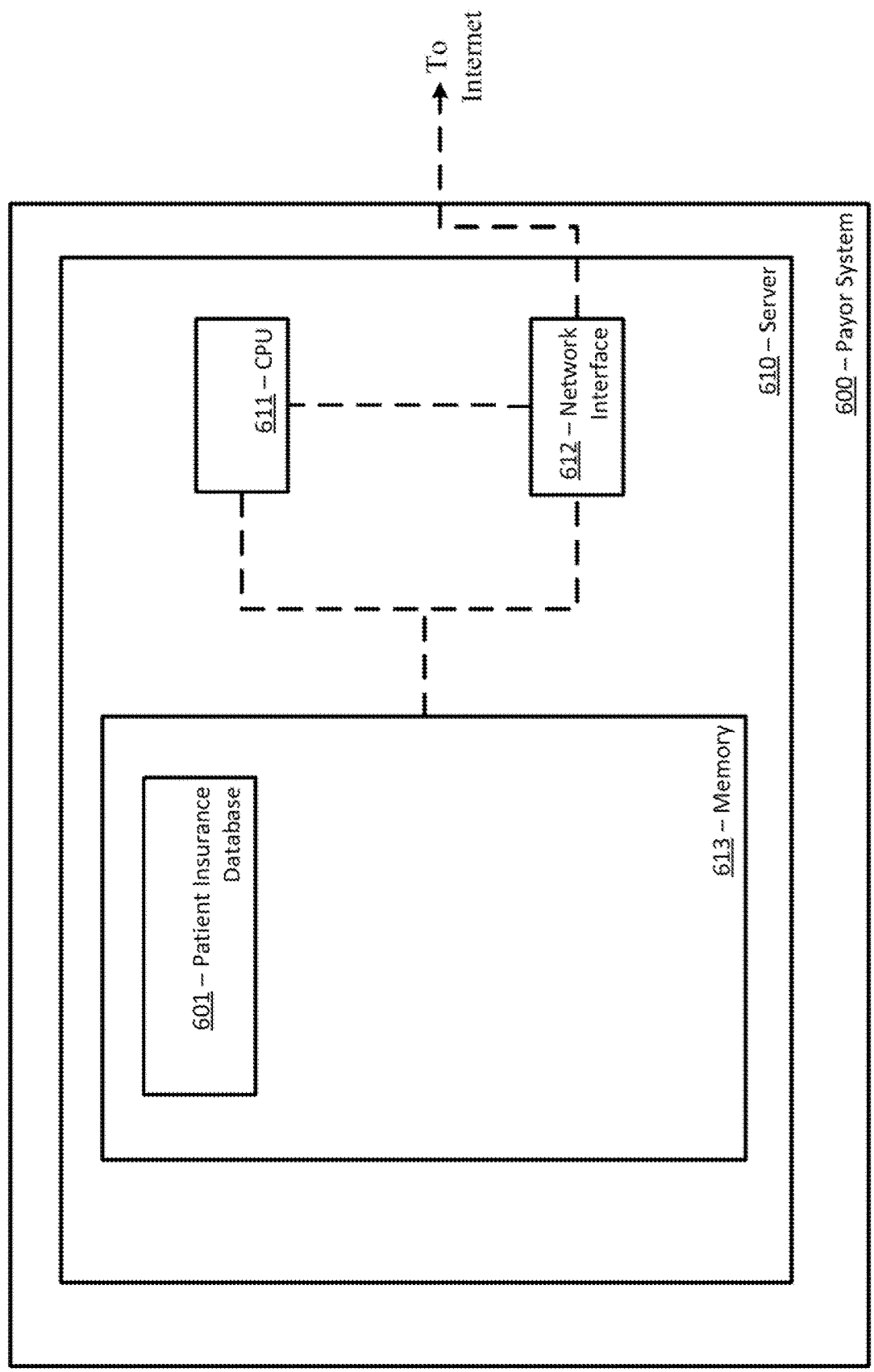
FIG. 7 is a schematic diagram of payor system for supplementing patient and provider interactions to increase patient adherence according to one embodiment of the present invention.

Referring to FIG. 7, a schematic diagram of a payor system 600 according to one embodiment of the present invention is illustrated. Generally, the payor system 600 comprises a server 610 which comprises a properly programmed processor (CPU) 611, a network interface 612, and a memory unit 613 in operable communication. It should be noted that the processor 611 may be considered the processor of the payor system 600. Further, although exemplified as a single server 610, the invention is not so limited and in alternate embodiments the payor system 600 may comprise any number of servers 610. Additionally, although not exemplified, it should be understood that the processor 611 can have integrated memory. The network interface 612 connects the server 610 to the over systems and modules of the system 1000 via the internet.

As discussed in more detail below, the processor 611 of the payor system 600 effectuates the performance of the processes and functions described herein, including but not limited to the storage of data to the database 601 of the memory 613 and the transfer of data (e.g., patient insurance information) between the payor system 600 and the other systems and modules of the system 1000.

The memory 613 of the payor system 600 comprises a patient insurance database 601. The patient insurance database 601 stores information relating to the payor of prescriptions for substances of patients, such as, but not limited to, the patient's insurance company, the patient's co-pay amount, and the patient's other deductibles. Further, although exemplified as a single memory unit, it should be noted that the memory 613 may comprise any number of databases used to store data, modules, or other information.

Therefore, it may be said that the system 1000 comprises a plurality of databases or one or more databases. Specifically, as noted above, the system 1000 comprises the EP database 201 on the EP system 200, the supplemental program database 303 and the records database 304 on the SP system 300, the coupon database 401, the educational information database 402, the patient medication/reminder service database 403, and the patient adherence service database 404 of the third party content providers 400, the prescription filling sub-system database 504 and the patient prescription history database 505 of the pharmacy system 500, and the patient insurance database 601 of the payor system 600.

Supplemental Programs

A supplemental program, as used herein, may be any document that is provided to a patient or any service in which a patient is enrolled that is designed for increasing patient adherence to a prescribed substance. Stated another way, a supplemental program may be a document or service designed to help patients understand their medication regimen and comply with it. For example, a supplemental program may be a coupon (or a coupon service) that is provided to a patient for a particular prescribed substance, educational material (either general or specific) that is provided to a patient for a particular prescribed substance or disease state, a combined coupon/educational document (referred to herein as an "EduSAVE™" document, one example of which is exemplified in FIG. 9), a loyalty card, a prescription reminder service, an appointment reminder service, a health care coaching service, or any other patient adherence service or document. In one embodiment, the available supplemental programs are all patient adherence programs. However, the invention is not so limited and in alternate embodiments, some or all of the available supplemental programs may not relate to patient adherence.

As discussed in more detail below, eligibility of a supplemental program is determined by comparing one or more of a plurality of different data elements (such as, but not limited to, a patient's general information, a patient's medical history, a brand name or formula of a substance prescribed to a patient, other information relating to a substance prescribed to a patient, a patient's payor's information (e.g., a patient's health insurance company and/or health insurance plan), a provider's general or specific information) with the rules of each of the available supplemental programs. If the data element(s) meets the rules for a specific supplemental program, then the patient is determined to be "eligible" for that program. For example, a specific program may only be eligible to patients who are being prescribed a particular substance, patients who reside within a particular geographic region, patients who have a specific history with a particular substance, patients who have at least specific co-pay for a particular substance, or patients whose providers meet certain qualifications.

As discussed in detail below, the determination of eligibility is determined by the SP module, and more specifically, by the rules engine of the SP module. Generally, the SP module receives and/or retrieves a plurality of data relating to the patient, the prescribed substance, the provider, and/or the payor, and applies that data to the rules of each of the available supplemental programs to determine supplemental programs in which the patient is eligible.

Method for Supplementing Patient and Provider Interactions

Generally and in accordance with one embodiment of the present invention, a method for supplementing patient and provider interactions to increase patient adherence generally comprises three steps: (1) determining, from a plurality of available supplemental programs, supplemental programs for which a particular patient receiving a prescription for a particular substance is eligible; (2) receiving confirmation/approval from the patient's health care provider that the eligible supplemental program should be activated; and (3) activating the eligible supplemental programs that the provider has confirmed/approved in order to increase patient adherence to the prescribed substance.

1. Determining Eligible Supplemental Programs for a Patient

Figure 8A:
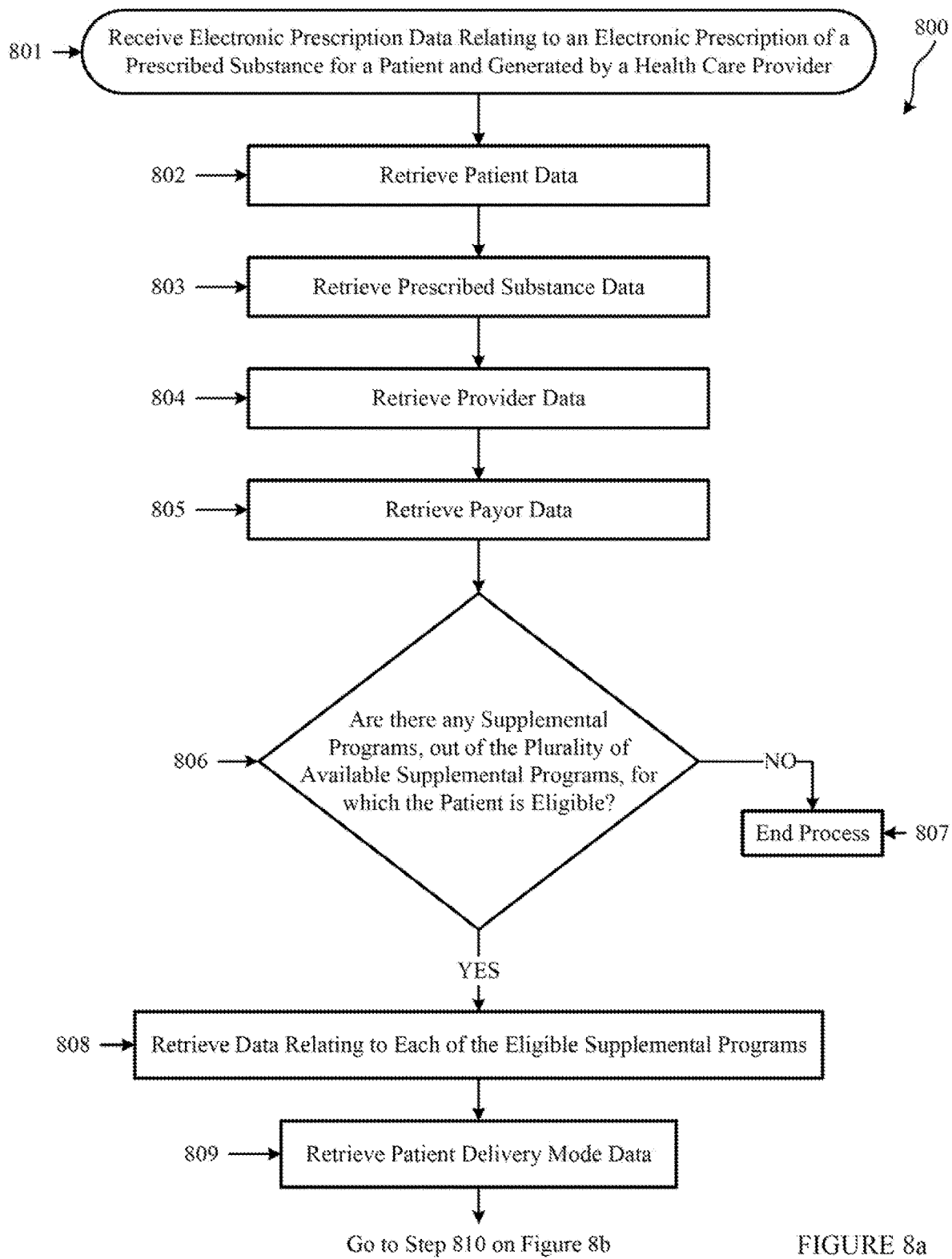
FIGS. 8a-8c is a flow chart of a system for supplementing patient and provider interactions to increase patient adherence according to one embodiment of the present invention.
Figure 8B:
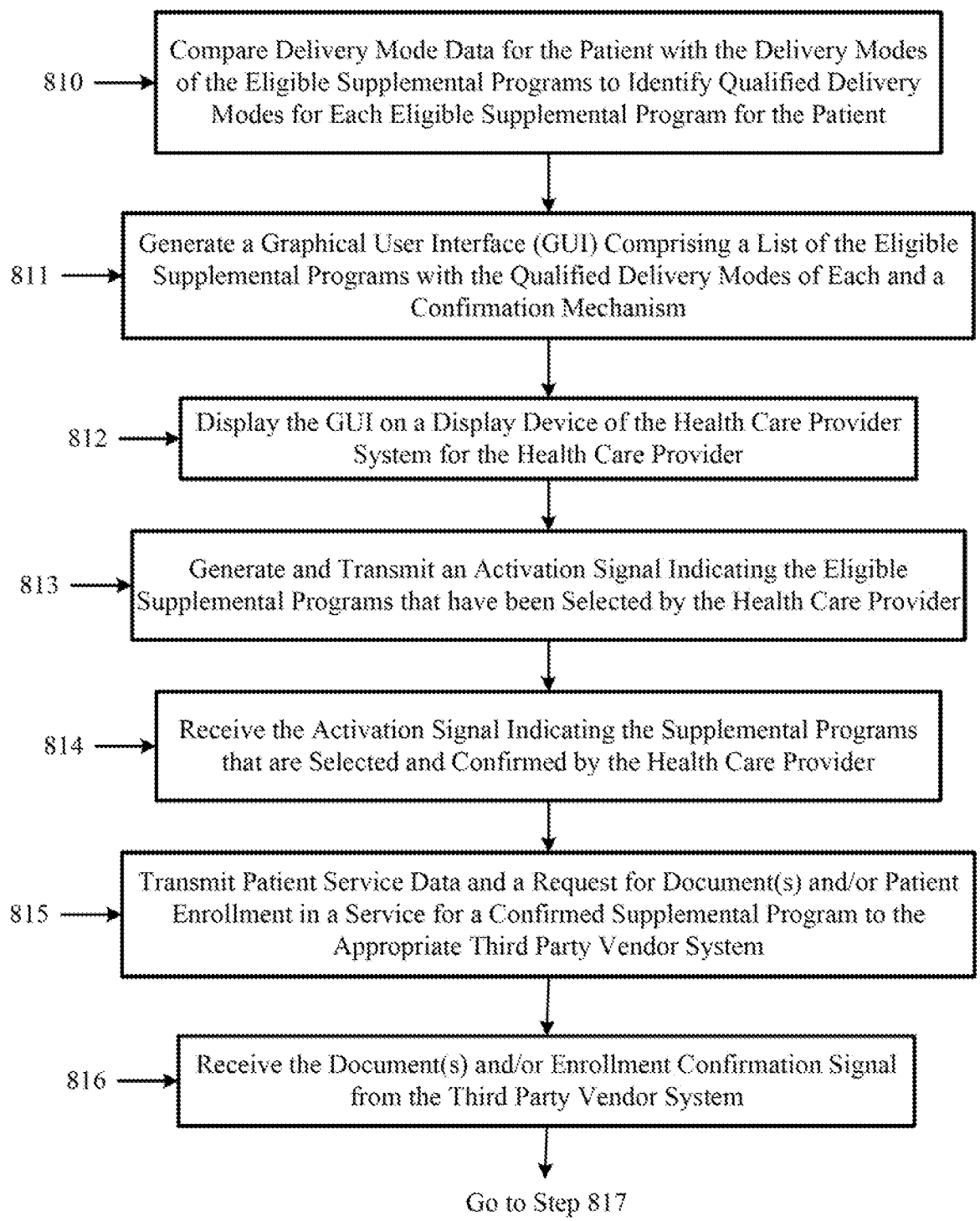
Figure 8C:
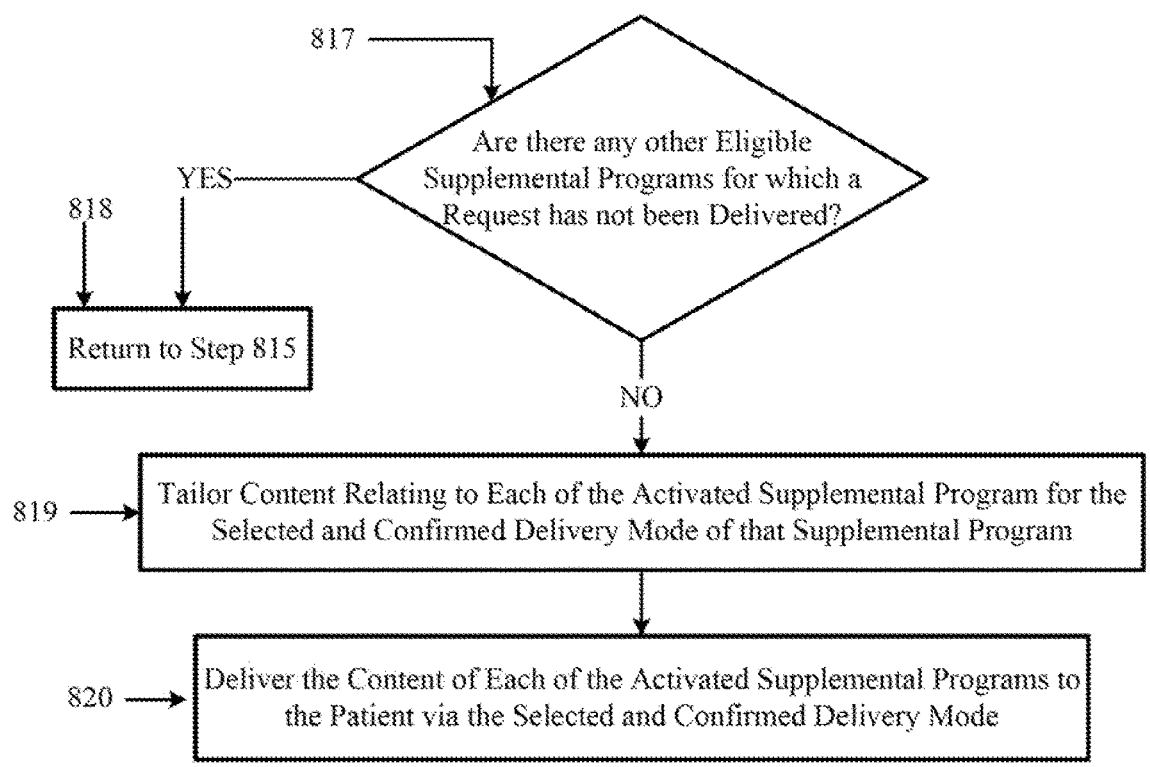

Referring to FIGS. 8a-8c, a flow chart of a system for supplementing patient and provider interactions to increase patient adherence according to one embodiment of the present invention is illustrated.

According to one embodiment of the present invention, the process begins when a patient visits their health care provider 101 seeking health care advice, and the provider 101, after diagnosing the patient, decides to write an electronic prescription for a particular substance for the patient. The electronic prescription is typically generated by the provider 201 using the EP module. Specifically, in one embodiment of the present invention, the provider 101 drafts an electronic prescription using the thin-client portion of the EP module 203, which resides on the HCP system 100.

Figure 10:
Figure 11:
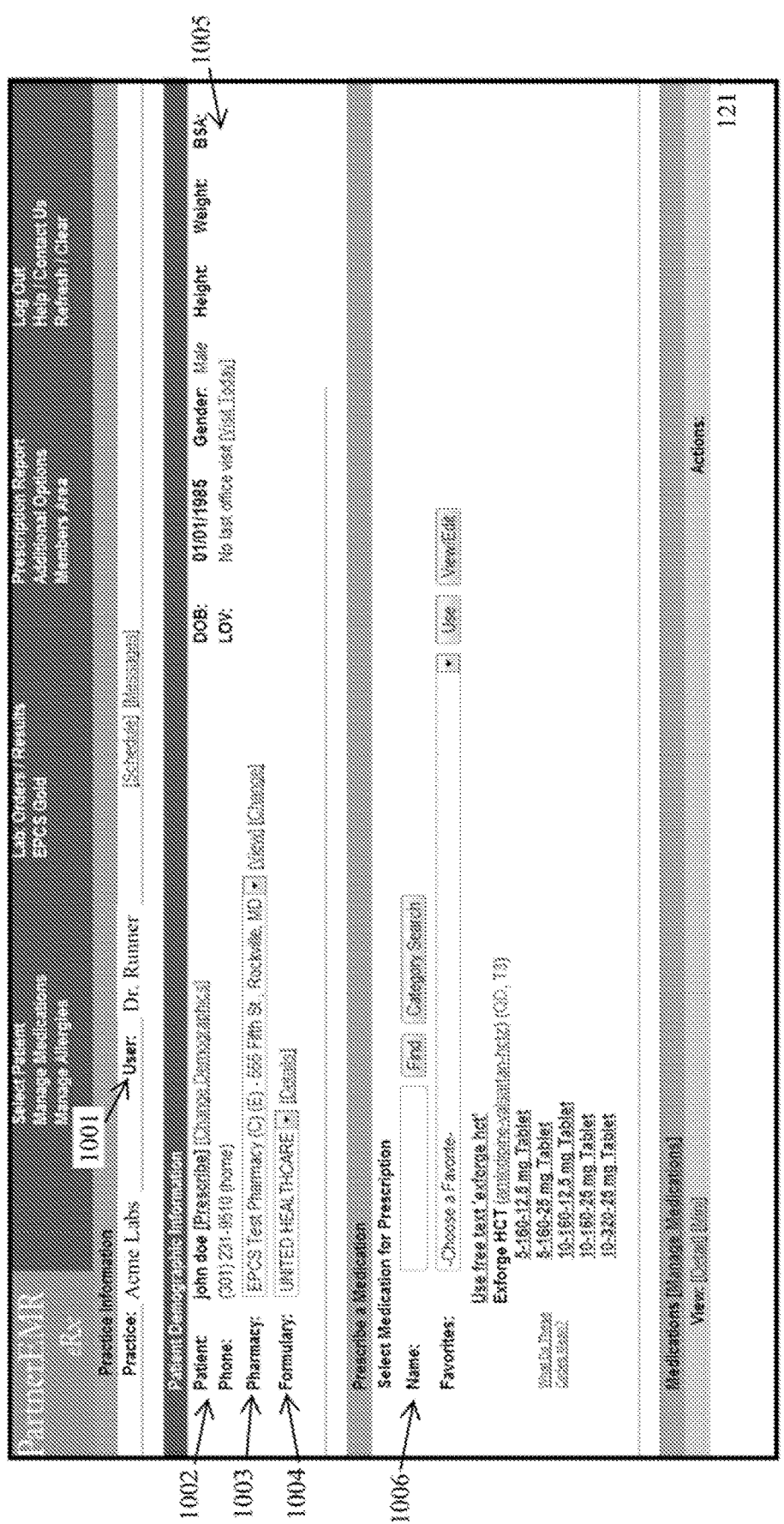

Referring to FIG. 10, a screen shot of a graphical user interface (GUI) generated by the EP module (and specifically the thin-client portion 203 of the EP module) to allow the provider 101 to generate an electronic prescription for a patient according to one embodiment of the present invention is illustrated. As shown in FIG. 10, the GUI comprises information relating to the provider (at least their name) 1001, information relating to the patient 1002, information relating to the pharmacy 1003 where the electronic prescription will be transmitted, information relating to the formulary of the patient 1004, information relating to the patient's medical history 1005, and information relating to a substance 1006 to be prescribed to the patient. Moreover, the GUI is not so limited and may further comprise information relating to the other medications previously prescribed to the patient, current allergies or adverse reactions of the patient, or other previously recorded problems of the patient.

Referring to FIGS. 11-14, multiple, sequential graphical user interfaces (GUIs) 1011, 1012, 1013, 1014 generated by the EP module to allow the provider 101 to generate an electronic prescription for a patient according to one embodiment of the present invention are illustrated. In the GUI 1011 exemplified in FIG. 11, the provider 101 may select a medication for prescription. As shown, the provider 101 may search for a new substance to prescribe by name or may choose a substance from a pre-established list of favorites. As shown in the GUI 1012 of FIG. 12, after a provider 101 chooses a substance to prescribe to the patient, the EP module generates and displays the GUI 1012, which comprises drug interaction warnings, formulary alerts based on the patient's formulary status, and other medication alerts and warnings.

After the provider 101 confirms the substance in the GUI 1012, the EP module generates and displays GUI 1013 (shown in FIG. 13), which allows the provider to enter the details of the substance to be prescribed 1006. For example, substance details such as the names, dosage, strength, form, duration, quantity, and refills are displayed for provider 101 input, along with directions to the patient and/or pharmacist and other details relating to the filling pharmacy and provider 101. After the provider 101, has entered all the required information using the input device 122 of their terminal 120 of the HCP system 100, the EP module generates a displays GUI 1014. As exemplified in FIG. 14, the GUI 1014 provides a summary of the electronic prescription for the substance for the provider's review. After the provider 101 reviews and confirms that the prescription is accurate, the electronic prescription for the substance is created.

Still also referring to FIGS. 8a-8c, in the exemplified embodiment, after an electronic prescription for the substance is created by the provider 101, the SP widget 302 retrieves data relating to the electronic prescription from the thin-client portion of the EP module 203. The SP widget 302 then transmits the electronic prescription data to the central portion 301 of the SP module residing on the SP system 300, such that the central portion 301 of the SP module receives the electronic prescription data, thereby completing step 801 in FIG. 8a. The electronic prescription data comprises first patient data that is specific to the patient, first prescribed substance data that is specific to the prescribed substance, first provider data that is specific to the provider 101, and first payor data that is specific to the payor.

The first patient data comprises the information that is part of the prescription and relates to the patient, such as but not limited to, the patient's name, gender, date of birth (DOB), contact information (telephone and address), and the patient's formulary status.

The first prescribed substance data comprises information that is part of the prescription and relates to the prescribed substance, such as but not limited to, the name of the prescribed substance, the dosage, strength, form, duration, and quantity of the prescribed substance, and the number of refills listed on the prescription.

The first provider data comprises information that is part of the prescription and relates to the provider 101, such as but not limited to, the provider's name, the address and phone number of the provider's practice, and national provider identifier (NPI) number.

The first payor data comprises information that is part of the prescription and relates to the payor of the patient, such as but not limited to, the payor's name and the formulary status (or health care plan) of the patient.

However, the invention is not so limited, and in an alternate embodiment of the present invention, the electronic prescription data may not relate to an electronic prescription currently being prescribed by the provider 101 for the patient, but rather relate to a refill, a renewal, or a previously prescribed substance. In such embodiments, the electronic prescription data may be received by the SP module from one of the other databases of the system 1000 (e.g., the EP database 201, the records database 304, the patient prescription history database 505, etc.).

Once the central portion 301 of the SP module receives the electronic prescription data, the central portion 301 of the SP module retrieves additional data prior to determining supplemental programs for which the patient is eligible. However, it should be noted that the invention is not so limited and in alternate embodiments, the central portion 301 of the SP module may only retrieve a portion of the data listed herein or may not retrieve any additional data prior to determining supplemental programs for which the patient is eligible.

In the exemplified embodiment, the central portion 301 of the SP module retrieves patient data that is specific to the patient from the record database 304, thereby completing step 802. The retrieved patient data may be referred to as "additional" or "second" patient data, or simply patient data. The patient data comprises one or more of the patient's current medication, the patient's recent drug fills, the patient's drug fill history, the patient's demographics, the patient's health care plan or payor information, the patient's adherence information, and the patient's clinical trial cohort (if the patient is part of a clinical trial cohort). The patient adherence information may relate to the patient's past adherence to prescriptions for the same prescribed substance, for prescriptions to prescribed substances for the same disease state, and/or the patient's general adherence to any combination of the substances they have previously been prescribed to the patient. It should be noted that this information is in addition to the first patient data that was retrieved by the centralized portion of the SP module 301 from the created electronic prescription.

Further, the central portion 301 of the SP module may also retrieve prescribed substance data relating to the substance prescribed by the electronic prescription from the record database 304, thereby completing step 803. The retrieved prescribed substance data may be referred to as "additional" or "second" prescribed substance data, or simply prescribed substance data. The prescribed substance data comprises one or more of the prescribed substance's drug properties, the prescribed substance's therapeutic class(es), a prescribed substance substitution code, the prescribed substance's formulary data, and a prescription indicator. It should be noted that this information is in addition to the first prescribed substance data that was retrieved by the central portion 301 of the SP module from the created electronic prescription.

The central portion 301 of the SP module may also retrieve provider data relating to the health care provider 101 from the record database 304, thereby completing step 804. The retrieved provider data may be referred to as "additional" or "second" provider data, or simply provider data. The provider data comprises one or more of the provider's geographic location, the provider's state of residency, and the specialty of the provider 101. It should be noted that this information is in addition to the first provider data that was retrieved by the central portion 301 of the SP module from the created electronic prescription.

The central portion 301 of the SP module may also retrieve payor data relating to the payor (e.g., a health care insurance company) of the patient from the record database 304, thereby completing step 805. The retrieved payor data may be referred to as "additional" or "second" payor data, or simply payor data. Further, according to one embodiment, if the record database 304 does not have any of the patient's payor information stored therein (or even if it does), then the central portion 301 of the SP module may transmit a request to the payor system 600 and receive back the patient's payor information from the patient insurance database 601. The payor data comprises one or more of the formulary status (or health care plan) of the patient, the co-pay of the patient, and any other information relating to the payor of the patient. It should be noted that this information is in addition to the first payor data that was retrieved by the central portion 301 of the SP module from the created electronic prescription.

According to one embodiment of the present invention, the central portion 301 of the SP module first attempts to retrieve the relevant data from the records database 304. Thereafter, if the records database 304 does not comprise the relevant data required by the central portion 301 to determine the eligible supplemental programs, then the central portion 301 reaches out to at least one other database on the system 1000, such as, but not limited to the EP database 201 and the patient insurance database 601. In one embodiment, upon retrieving the relevant data from one of the other databases of the system 1000, the central portion 301 stores the relevant data in the records database 304 for future processing.

After the central portion 301 of the SP module retrieves the additional data required, the central portion 301, using the rules engine, determines, from a plurality of available supplemental programs, supplemental programs for which the patient is eligible based on the electronic prescription for the substance. As discussed above, a plurality of available supplemental programs are stored within one or more databases, which includes but is not limited to the supplemental program database 303 and the databases 401, 402, 403, 404 of the third party content providers 400. As noted above, according to one embodiment of the present invention each available supplemental program is a document that is provided to a patient or a service in which a patient is enrolled. Moreover, according to one embodiment, each available supplemental program is designed to increase patient adherence to the prescribed substance.

As also noted above, each supplemental program out of the plurality of available supplemental programs comprises one or more rules. Generally, the rules of a supplemental program must be met in order for the patient to be "eligible" for the supplemental program. The rules may relate to information relating to the patient, the prescribed substance, the provider, and/or the payor of the patient. Therefore, the rules of each of the available supplemental programs may act as constraints and/or restrictions dictating the eligibility of a patient for a particular available supplemental program.

Examples of rules include, but are not limited to, restricting a supplemental program to a specific prescribed substance or disease state, restricting a supplemental program to a specific prescribed substance of a specific dosage strength, restricting a supplemental program to patients or providers of a specific geographic region, restricting a supplemental program to patients who have a certain adherence history (whether with the prescribed substance or in general), restricting a supplemental program to patients who have a specific persistency rate for the prescribed substance (e.g., a persistency rate under 60%, a persistency rate between 30%-60%, or a persistency rate between 10%-85%), restricting a supplemental program to patients of a certain age or age range, restricting a supplemental program to patients who have been prescribed the substance for at least a predetermined time period, restricting a supplemental program to patients who have a certain co-pay for a specific prescribed substance, restricting a supplemental program to patient's having a certain health insurance carrier, etc.

Therefore, for example, a specific supplemental program is only eligible to patients who meet the rules described above. Restricting the dissemination of supplemental programs on the basis of the rules listed above may be beneficial since supplemental programs will only go to those patients with which they will have the greatest effect. Therefore, for example, a pharmaceutical company is not blindly handing out coupons to patients whose habits may not be affected by the receipt of a coupon. Rather, the coupons are distributed on the basis of predetermined rules to increase the likelihood that the coupons will result in increased adherence by the patient, and in turn, sales of the prescribed substance and reduced costs to the other parties involved. Further, since the determination of eligibility is performed by the rules engine of the SP module, the health care provider 101, may, but is not required to calculate or analyze whether a patient would be incentivized by a supplemental program. This helps to alleviate some of the burden typically placed on health care providers 101 with regards to disseminating documentation to their patients.

Further, according to another embodiment of the present invention, rules may further include a patient's specific usage stage for a substance. Therefore, in one embodiment, a patient may only be eligible for supplemental program that provides a specific coupon if they are at a specific usage stage for a particular substance. For example, a patient may only be eligible for a coupon if they are after their second refill for a particular substance, or if they are between their third and fourth refill of a particular substance. In such embodiments, providing coupons to a patient based on their specific usage stage for a substance may encourage continued patient adherence for that substance.

The rules engine of the central portion 301 of the SP module determines the eligibility of each of the plurality of available supplemental programs for the patient by comparing the data received/retrieved by the SP module with the rules of each available supplemental program. As noted above, the data used in the comparison includes, but is not limited to, the first patient data received from the electronic prescription, the first prescribed substance data from the electronic prescription, the first provider data from the electronic prescription, the first payor data from the electronic prescription, the patient data retrieved by the central portion 301 of the SP module, the prescribed substance data retrieved by the central portion 301 of the SP module, the provider data retrieved by the central portion 301 of the SP module, and the payor data retrieved by the central portion 301 of the SP module. Therefore, the eligibility of each of the available supplemental programs is determined by the rules engine of the central portion 301 of the SP module using any combination of the data (or data elements) listed above.

Still referring to FIG. 8*a*, in decision step 806, the central portion 301 of the SP module, using the rules engine, determines the eligibility of the plurality of available supplemental programs by comparing the data received and retrieved (e.g., the patient data, the prescribed substance data, the provider data, and the payor data discussed above) with the rules of each of the available supplemental programs. If the received/retrieved data does not meet the rules of any of the plurality of available supplemental programs, then the process ends at step 807. However, if the received/retrieved data meets the rules of at least one available supplemental program, then the process continues to step 808. It should be noted that those supplemental programs whose rules are determined by the rules engine to meet the received and retrieved data are considered eligible supplemental programs.

Further, it should be noted that although exemplified as a single determination step, the invention is not so limited. In one embodiment of the present invention, the determination of eligible supplemental programs by the rules engine of the SP module is a multi-step comparison process. For example, in one embodiment of the present invention, during a first comparison step the central portion 301 of the SP module compares the prescribed substance data (including either the first prescribed substance data retrieved from the electronic prescription and/or the prescribed substance data retrieved from the record database 304) with the rules of each of the available supplemental programs. More specifically, the rules engine of the SP module may compare the brand name or formula of the prescribed substance with each of the plurality of available supplemental programs. If the brand name or formula of the prescribed substance matches the brand name or formula of a rule an available supplemental program, then that supplemental program passes the first comparison step of the rules engine.

If the prescribed substance data does meet the rules of at least one available supplemental program, then the central portion 301 of the SP module performs a second comparison step, whereby the SP module compares the patient data (including either the first patient data retrieved from the electronic prescription and/or the patient data retrieved from the record database 304) with the rules of each of the supplemental programs that passed the first comparison step. Thereafter, the SP module may perform subsequent comparison steps using the provider data and/or the payor data. In such embodiments, a patient is "eligible" for a supplemental program, if and only if, the supplemental program passes each step of the multi-step comparison process.

It should be noted that in such multi-step comparison embodiments, the invention is not limited to any specific number of comparison steps, the order of the comparison steps, or the types of comparison steps (e.g., steps using prescribed substance data, using patient data, using provider data, or using payor data).

Further, it should be noted that in an alternate embodiment of the present invention, the central portion 301 of the SP module transmits the data received and retrieved from the one or more databases (e.g., the patient, prescribed substance, provider, and payor data discussed above) to a third party system (e.g., one of the third party content providers 400). Thereafter, the third party system compares the data against the rules of each of the available supplemental programs to determine eligibility. After testing the data against the rules, the third party system transmits a signal back to the central portion 301 of the SP module indicating which of the available supplemental programs are eligible. Therefore, in such embodiments, the SP module determines the eligibility of the available supplemental programs by transmitting the appropriate data to a third party system and receiving back a signal indicating for which of the available supplemental programs the patient is eligible.

Although not exemplified, in one embodiment of the present invention, prior to performing step 806, the central portion 301 of the SP module retrieves provider preference data (and/or patient preference data) from the records database 304 and/or the supplemental program database 303. Provider preference data is information that relates to the preferences of the specific provider 101 who drafted the prescribed substance. Similarly, patient preference data is information that relates to the preferences of the patient which whom the substance is being prescribed. The preference data includes, but is not limited to, specific modes of delivery (e.g., print, email, SMS, etc.) and supplemental program types (e.g. educational material, coupons, reminder services, etc.) that the provider 101 and/or patient prefers.

If the SP module locates and retrieves preferences for the provider 101 and/or patient, then the following steps are limited to those supplemental programs and delivery modes that are preferred by the provider and/or patient. For example, if the provider 101 sets their preferences to select only a specific type of supplemental program (e.g., educational material), then the SP module will only determine eligible supplemental programs that are of that specific type of supplemental program. For purposes of this discussion, we will assume that the SP module does not retrieve any provider or patient preference data.

According to one embodiment of the present invention, the SP module receives provider 101 and/or patient preference data directly from the provider 101 via the input device 122 of the HCP system 100. However, it should be noted that in other embodiments of the present invention, the SP module may learn the preferences of a provider 101 and/or a patient based on one or more previous instances where the provider 101 and/or patient used the SP module. Upon receiving or learning provider 101 and/or patient preference data, the central portion 301 of the SP module stores the preference data in the record database 304.

After the SP module determines which of the available supplemental programs the patient is eligible, the central portion 301 of the SP module retrieves supplemental program data relating to each of the eligible supplemental programs from the supplemental program database 303, thereby completing step 808. It should be noted that, according to one embodiment of the present invention, the supplemental program data is not the actual supplemental program itself, but rather information relating to each of the supplemental programs.

In the exemplified embodiment, the supplemental program data comprises information about the eligible supplemental program, such as, but not limited to, the name of the eligible supplemental program, the specific type of document or service the eligible supplemental program comprises, and delivery mode data relating to the available delivery modes of each of the eligible supplemental programs. Further, it should be noted that if the received/retrieved data meets the rules of more than one available supplemental program, then the central portion 301 of the SP module retrieves supplemental program data relating to each of the plurality of eligible supplemental programs from the supplemental program database 303.

However, the invention is not so limited, and in another embodiment of the present invention, the central portion 301 of the SP module retrieves the supplemental program data from the one or more databases 401, 402, 403, 404 of the appropriate third party content provider 400. Further, in another alternate embodiment, the central portion 301 of the SP module may actual receive the supplemental programs itself at step 808.

After retrieving the supplemental program data in step 808, the central portion 310 of the SP module retrieves patient delivery mode data relating to the delivery modes that are available for the patient from the record database 304 of the SP system 300, thereby completing step 809. The patient delivery mode data comprises information relating to the patient, such as but not limited to, an email address of the patient, a phone number of the patient, and a mailing address of the patient. It should be noted that the central portion 301 of the SP module can retrieve information about the patient that is currently stored in the record database 304, along with patient data that is stored in the other, one or more databases of the system 1000.

After retrieving patient delivery mode data, the central portion 301 of the SP module compares the patient delivery mode data with the delivery mode data for each of the eligible supplemental programs, thereby completing step 810. As noted above, the delivery mode data for the eligible supplemental programs is retrieved by the central portion 301 in step 808. The comparison is done in order to determine qualified delivery modes for each of the eligible supplemental programs. A qualified delivery mode is a delivery mode that is available for a supplemental program and a delivery mode in which the patient delivery mode data (e.g., the patient's email address, phone number, etc.) relating to that delivery mode is stored in the SP system 300 and has been retrieved by the SP module.

As discussed in more detail below and according to one embodiment of the present invention, eligible supplemental programs that do have qualified delivery modes may be preselected by the SP module for those specific delivery modes. Further, in another embodiment of the present invention, eligible supplemental programs that do not have at least one qualified delivery modes associated therewith may be locked so as to be incapable of selection by the provider 101. In such embodiments, if the provider 101 may be required to enter patient delivery mode information into the GUI of FIG. 15 described below in order to unlock the selection mechanism for that particular supplemental program. Further, it should be noted that the invention is not so limited, and in other alternate embodiments the qualified delivery modes may just be preselected by the SP module, while the non-qualified delivery modes are grayed-out or only selectable upon the provider 101 entering the appropriate patient delivery mode information.

Further, in yet another embodiment of the present invention, the SP module does not retrieve patient delivery mode data and, therefore a comparison between patient delivery mode data and delivery mode data for each of the eligible supplemental programs is not performed by the SP module. In such instances, all of the available delivery modes for each of the eligible supplemental programs may be displayed in the GUI to the provider 101 using the display device 121.

2. Receiving Confirmation from the Health Care Provider to Activate the Supplemental Programs After the SP module has determined supplemental programs for which the patient is eligible, the SP module generates and displays a GUI to the provider 101 in order to receive confirmation from the provider 101 regarding which of the eligible supplemental programs should be activated.

Referring to FIG. 8b and after step 810, the SP module generates a GUI that comprises a list of the eligible supplemental programs for the provider's selection and confirmation by the health care provider 101, thereby completing step 811. In one embodiment of the present invention, the central portion 301 of the SP module generates the GUI that comprises the list of eligible supplemental programs for the patient, and then transmits the GUI to the SP widget 302 for display to the provider 101 in the display device 121. However, in alternate embodiments of the present invention, the GUI is generated and displayed by the SP widget 302.

Figure 15:
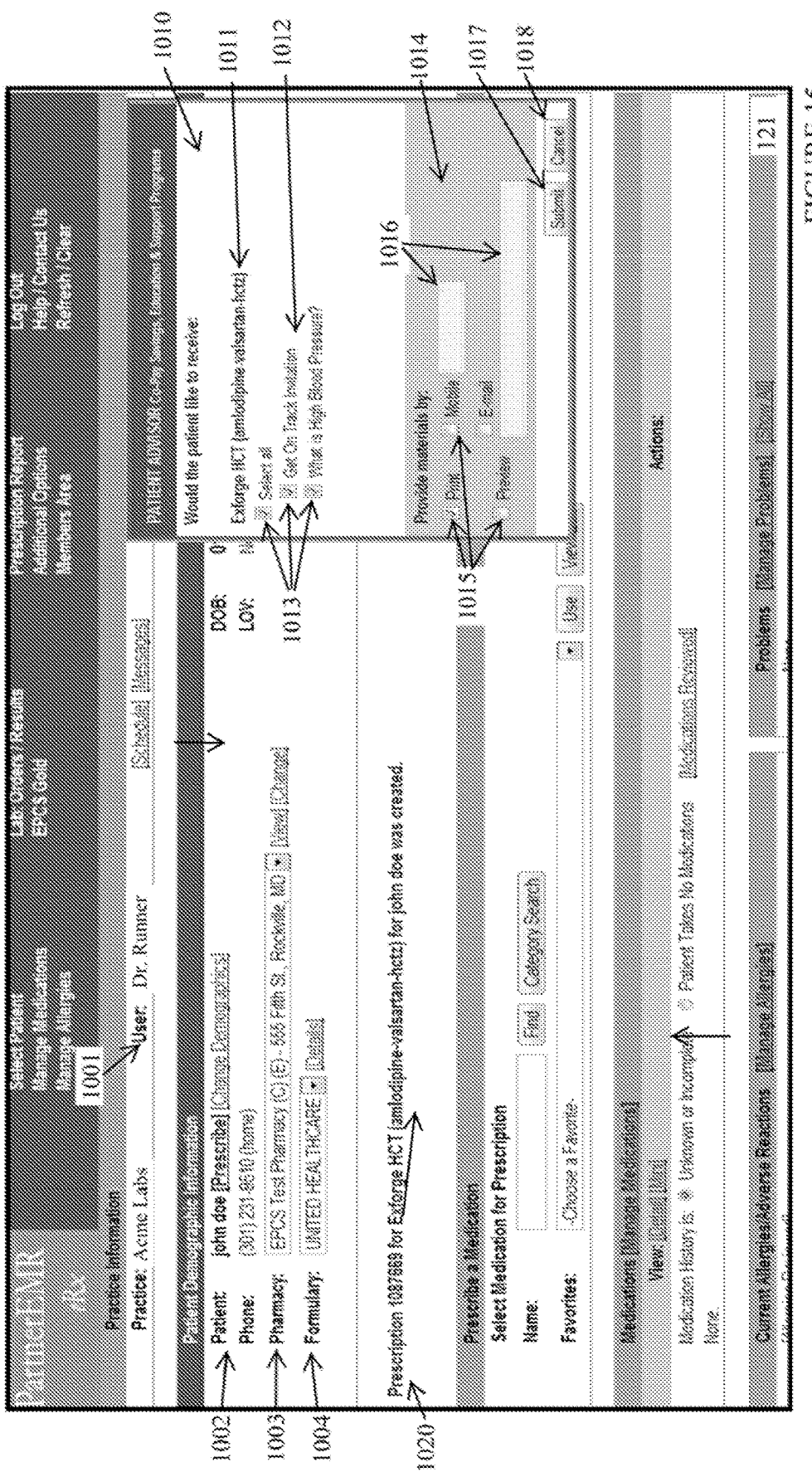

After the GUI is generated, the SP widget 302 displays the GUI in the display device 121 of the terminal 120 to the provider 101, thereby completing step 812. One example of a GUI is shown in FIG. 15. As exemplified by the GUI of FIG. 15, the GUI comprises a pop-up window 1010, which comprises information relating to the substance 1011 for which eligible supplemental programs are being presented, information relating to the eligible supplemental programs 1012, selection mechanisms 1013 for each of the eligible supplemental programs, information relating to delivery modes 1014 available for the eligible supplemental programs, delivery mode selection mechanisms 1015 for each of the delivery modes available for each of the eligible supplemental programs, delivery mode input fields 1016, a confirmation mechanism 1017, and a cancellation mechanism 1018.

Still referring to FIG. 15, although only one substance is listed in the window 1010, it should be noted that section 1011 may comprise information relating to a plurality of prescribed substances. For instance, if the provider 101 drafts more than one prescription relating to more than one substance for the patient and the SP module determines that there are eligible supplemental programs relating to more than one of the prescribed substances, then the window 1010 will comprises a list of each of the substances 1011 along with a list of each of their associated eligible supplemental programs 1012.

As further exemplified by the window 1010; section 1012 which comprises a list of the eligible supplemental programs for each of the prescribed substances, also comprises a selection mechanism 1013 to allow the provider 101 to determine which of the eligible supplemental programs they would like to activate for their patient. The selection mechanism 1013 allows each of the eligible supplemental programs to be selected and/or deselected by the provider 101 using the input means 122 of the HCP system 100. As discussed in more detail below, the eligible supplemental programs that are selected (e.g., via a check box) by the provider 101 using the selection mechanism 1013 when the confirmation mechanism 1017 is actuated by the provider 101 will be activated by the SP module for the patient upon the provider 101 actuating the confirmation mechanism 1017. Although exemplified as a check box, the invention is not so limited and in alternate embodiments the selection mechanism 1013 may be changed to include any selection mechanism known in the art.

Moreover, as discussed above, it should be noted that if the supplemental program database 303 and/or the records database 304 comprises provider preference data and/or patient preference data, then the SP module will upload that information and generate the window 1010 based on that information. For instance, if the preference data relates to specific types of supplemental programs or delivery modes preferred by the provider 101 or patient, then the selection mechanisms 1013, 1015 for those supplemental program and/or delivery modes will be pre-selected when the window 1010 is generated by the central portion 301 of the SP module and displayed by the SP widget 302 on the display device 121 for the provider 101.

Still referring to the window 1010 shown in FIG. 15, a list of available delivery modes 1014 for the eligible supplemental programs is also displayed for the provider 101. As shown, each delivery mode comprises a delivery mode selection mechanism 1015 that may be selected and/or deselected by the provider 101 using the input means 122. The delivery mode selection mechanisms 1015 allow the provider 101 to determine how the supplemental programs will be delivered to the patient. Further, it should be noted that more than one delivery mode may be selected by the provider 101. In such instances, the supplemental programs will be delivered to the patient via all of the selected delivery modes. Although the delivery modes are shown to comprise print, email, and text/SMS, the invention is not so limited and in alternate embodiments, the delivery modes may also include mailing to the patient's address, along with other methods of delivering documents to the patient.

Further, the window 1010 also comprises the delivery mode input fields 1016, which allow a provider 101 to manually enter in the patient's mobile phone number, email address, or other patient delivery mode information required for delivery of a supplemental program. If the provider 101 enters patient delivery mode information into a delivery mode input field 1016, then upon the provider 101 actuating the confirmation mechanism 1017, the SP module stores the patient's delivery mode information in one or more databases of the system 1000 (e.g., the records database 304) for future instances. Additionally, it should be noted that if the patient's delivery mode information (e.g., email, phone number, address, etc.) is previously stored in one or more of the databases of the system 1000 (e.g., the record database 304, the EP database 201, etc.), then the SP module will retrieve the patient's delivery mode information from the one or more databases and auto-populate the delivery mode input fields 1016 in window 1010.

Further, one of the delivery mode input Field 1016 shown in the window 1010 is a preview field. The preview field allows the provider 101 to preview the eligible supplemental program(s) before activating the program(s) for the patient. If the supplemental program is a coupon, education material, or other document, then another window displaying the document or information relating to the document will be generated and displayed by the SP module in the display device 121. According to one embodiment of the present invention, if the supplemental program is a service, then another window displaying general information relating to the service will be generated and displayed by the SP module in the display device 121.

As noted above, according to one embodiment of the present invention, prior to generating and displaying the window 1010, the SP module retrieves delivery mode data relating to the eligible supplemental program and the patient. In the list of delivery modes 1014 exemplified in FIG. 15, "print" is a qualified delivery mode and the delivery mode input field 1016 for print has been pre-selected by the SP widget 302. Since the other delivery modes, such as email and mobile, do not comprise patient delivery mode data, they are not qualified delivery modes and are not pre-selected by the SP module.

Referring to both FIG. 8*b* and FIG. 15, after the provider 101 has selected the eligible supplemental programs and the delivery mode(s) for the eligible supplemental programs that they would like to activate for the patient, the provider 101 actuates the confirmation mechanism 1017. Upon actuating the confirmation mechanism 1017, the SP widget 302 generates and transmits an activation signal for each of the supplemental programs that have been selected by the provider 101 to the central portion 301 of the SP module, thereby completing step 813. Each of the activation signals comprises information relating to the eligible supplemental program itself, along with the delivery mode selected by the provider 101. However, the invention is not so limited and in alternate embodiments, the SP widget 302 generates and transmits a single activation signal that comprises information relating to all of the eligible supplemental programs that were selected by the provider 101.

Although exemplified as an icon in the window 1010, the confirmation mechanism 1017 is not so limited. In alternate embodiments, the confirmation mechanism 1017 may be a button, switch, lever, etc. that can be actuated by the provider to confirm the selected eligible supplemental programs and delivery modes.

However, if the provider 101 decides that they do not want to have any of the eligible supplemental programs activated for the patient, then the provider 101 may actuate the cancellation mechanism 1018. Upon actuating the cancellation mechanism 1018, the SP widget 302 generates and transmits a cancellation signal to the central portion 301 of the SP module. In such instances, none of the eligible supplemental programs are activated for the patient.

As shown in FIG. 15, the window 1010 is displayed concurrently with the electronic prescription interface that was used to generate the electronic prescription data previously received by the SP module. More specifically, the window 1010 overlays the electronic prescription interface and is automatically generated and displayed by the SP module in the display device 121 during the electronic prescriptions session undertaken by the provider 101. By using such a system, the provider 101 does not have to leave their electronic prescription writing interface in order to be presented with eligible supplemental programs for their patients. Stated simply, the SP module, due in part to the SP widget 302 being integrated into the EP module, provides one continuous interface for the provider 101 during their prescription writing/supplemental program activating process.

This is beneficial because it allows the provider 101 to know what sorts of supplemental programs are available for their patient and, specifically for the substance the provider 101 is currently prescribing for their patient, without having to leave their electronic prescription writing interface. Such a system encourages providers 101 to disseminate documents and enroll their patients in services to increase their patient adherence in their prescribed substances.

Further, additional benefits arise from granting the provider 101 the ability not only to select what specific supplemental programs will be activated for each and every one of their patients, but also the ability to preview the supplemental programs before they are activated for the patient. Additionally, the provider 101 may select the specific delivery mode for each patient. Therefore, the provider 101 may tailor the supplemental programs depending on the particular preferences of the patient, as well as what the provider 101 believes will result in the most beneficial results. Finally, allowing the provider 101 to be the gatekeeper between the supplemental programs and the patient encourages communication between the provider 101 and patient, which ultimately results in better care for the patient.

Although exemplified as pop-up window 1010, it should be noted that the invention is not so limited. In alternate embodiments, the provider interface created by the SP module may be any interface designed to allow the provider 101 to select and confirm the specific supplemental programs they would like to be delivered to the patient. For example, the interface may be a screen that takes up the entirety of the display device 121 or a window that is separate from the EP module (as opposed to pop-up window 1010, which is displayed on top of the electronic prescription writing interface). Stated simply, the current invention is not limited to the type of interface generated and displayed to the provider 101.

3. Activating the Eligible Supplemental Programs that have been Confirmed by the Health Care Provider In general, activation of an eligible supplemental program begins when the provider 101 actuates the confirmation mechanism 1017 after selecting the programs they would like to be activated for their patient. In the embodiments discussed with reference to FIGS. 8a-8c, activation begins with step 813 and continues to step 818. However, it should be noted that in alternate embodiments of the present invention, activation further includes step 819 and sometimes even step 820. Moreover, in another embodiment of the present invention, activation only includes step 813, which comprises the SP widget 302 generating and transmitting an activation signal to the central portion of the SP module 301 upon the provider 101 actuating the confirmation mechanism 1017.

Referring to FIG. 8b, after the SP widget 302 generates and transmits the activation signal for each of the supplemental programs, the central portion 301 of the SP module receives the activation signals, thereby completing step 814. Using the received activation signals, the central portion 301 of the SP module determines which of the eligible supplemental programs the provider 101 has confirmed.

Thereafter, the central portion 301 of the SP module transmits the relevant data for one of the confirmed supplemental program to the appropriate third party content provider 400, thereby completing step 815. For instance, if the confirmed supplemental program is a document (e.g., a coupon, educational material, EduSAVE™, etc.), then the central portion 301 of the SP module transmits at least a request for the document(s) to the appropriate third party content provider 400. Similarly, if the supplemental program is a service (e.g., a prescription reminder service, a medication reminder service, an appointment reminder service, a patient adherence service, etc.), then the central portion 301 of the SP module transmits a request for patient enrollment in the service. Therefore, depending on the specific document or service requested, the central portion 301 of the SP module transmits the relevant request to the appropriate server 410, 420, 430, 440 of the third party content provider 400.

It should be noted that in some embodiments of the present invention, the central portion 301 of the SP module may also transmit patient delivery mode data to the third party content provider 400. This may be required if the third party content provider 400 is to deliver the content directly to the patient or enroll the patient directly into the service.

Upon receiving the request from the central portion 301 of the SP module, the appropriate third party content provider 400 determines whether the request is for a document or a service. If the request is for a document, then the third party content provider 400 generates the document and returns the document to the central portion 301 of the SP module. If the request is for a service, then the third party content provider 400 configures the service and transmits a configuration signal back to the central portion 301 of the SP module. Specifically, the corresponding document or service is retrieved from the appropriate one of the databases 401, 402, 403, 404.

Thereafter, the central portion 301 of the SP module receives the document(s) and/or enrollment confirmation signal from the third party content system 400, thereby completing step 816. Next, the central portion 301 of the SP module determines if there are any other eligible supplemental programs for which a request has yet to be delivered to the third party vendor system 400 at decision step 817. If there are additional confirmed supplemental programs for which relevant data has not yet been transmitted to the third party content system 400, then the process returns to step 815 and the central portion 301 of the SP module transmits the relevant data for another of the confirmed supplemental program to the appropriate third party content provider 400. However, if the relevant data has been transmitted to the third party content system 400 for each of the confirmed supplemental programs, then the process continues to step 819.

It should be noted that in one embodiment of the present invention, the central portion 301 of the SP module transmits the relevant data for all of the confirmed supplemental programs to the appropriate third party content provider 400 at step 815. In such instances, decision step 817 may be omitted.

Therefore, after a request has been delivered by the central portion 301 of the SP module to the appropriate third party content provide 400 for all of the eligible supplemental programs that were confirmed by the provider 101, the SP module has activated each of the supplemental programs. Generally, by activating a supplemental program the SP module either receives content, such as a document to the patient, that is to be delivered to the patient or enrolls the patient in one of the aforementioned services via the appropriate third party content provider 400.

A non-limiting list of examples whereby the SP module activates a supplemental program is discussed below. It should be noted that the invention is not limited to the explicit examples presented herein. In one embodiment, in which the supplemental program is a coupon service, the SP module activates the supplemental program by retrieving coupon data relating to the prescribed substance from the coupon database 401 of the appropriate third party content provider 400 and integrating the coupon data into the electronic prescription. The integration of the coupon data into the electronic prescription is done by the SP widget 302, which is integrated into the thin-client portion 320 of the EP module residing on the HCP system 100. Thereafter, the HCP system 100 may transmit the electronic prescription with integration coupon to the pharmacy system 500 for further processing.

In another embodiment, in which the supplemental program is a coupon service, the SP module activates the supplemental program by retrieving the coupon data and provisioning a coupon based on the coupon data. Further, in one embodiment, activation further includes the SP module delivering the coupon to the patient via the selected delivery mode. For instance, the coupon may be delivered to the HCP system 100 so the provider 101 may print the coupon out for the patient using the printer 130, or the coupon may be delivered directly to the patient via one of the delivery modes discussed above.

For further example, in one embodiment in which the supplemental program is a prescribed substance education service, the SP module activates the supplemental program by retrieving educational content relating to the prescribed substance from the educational information database 402 of the appropriate third party content provider 400. Thereafter, according to one embodiment, activation may further include the SP module delivering the education content to the patient via the selected delivery mode. Therefore, the education content may be delivered to the patient by transmitting the educational content to the HCP system 100 so the content may be printed by the provider 101 for the patient using the printer 130, or the educational content may be delivered directly to the patient via one of the delivery modes discussed above.

Additionally, in another embodiment in which the supplemental programs is a prescribed substance education service and/or a coupon service, the SP module activates the supplemental program by retrieving education content relating to the prescribed substance from the educational information database 402 of the appropriate third party content provider 400 and integrating the educational content into a coupon (such as the EduSAVE™ document shown in FIG. 9). Further, according to one embodiment of the present invention, activation may further include delivering the combined educational coupon to the patient via the selected delivery mode. Similarly, the combined educational coupon may be delivered to the patient by transmitting the educational content to the HCP system 100 so the educational coupon may be printed by the provider 101 for the patient using the printer 130, or the educational coupon may be delivered directly to the patient via one of the delivery modes discussed above.

In one embodiment, in which the supplemental program is a patient adherence service, the SP module activates the supplemental program by enrolling the patient in the patient adherence service. According to another embodiment of the present invention, in which the activated supplemental program is a prescription reminder service, the SP module activates the supplemental program by enrolling the patient in the prescription reminder service. In yet another embodiment of the present invention, in which the activated supplemental programs is an appointment reminder service, the SP module activates the supplemental program by enrolling the patient in the reminder service.

In the exemplified embodiments, the SP module enrolls the patient in the service by transmitting the relevant data to the appropriate third party content provider 400, and the appropriate third party content provider 400 signs the patient up for the service. For example, the relevant data may include data relating to the patient, data relating to the patient's past adherence, data relating to the electronic prescription, and data relating to the patient's appointment schedule. However, in alternate embodiments of the present invention the SP module may enroll the patient into the service without the use of the appropriate third party content provider 400. In such embodiments, the SP module may further comprise an enrollment engine in order to effectuate the enrollment of the patient in the appropriate service directly.

For example, in embodiments where the SP module further comprises an enrollment engine, the central portion 301 of the SP module would effectuate the enrollment of patients into the services that were activated for them, without the need of the SP module transmitting patient enrollment data to a third party content provider 400.

Referring back to FIG. 8c, after the SP module is done activating the eligible supplemental programs that have been confirmed by the health care provider 101, the SP module tailors the content relating to each of the activated supplemental programs for the specific delivery mode that was selected and confirmed by the provider 101, thereby completing step 819. Generally, the central portion 301 of the SP module alters the specific document depending on the specific delivery mode selected and confirmed by the provider 101. For instance, if the delivery mode is selected to be via email, then the content is configured to be most easily viewable by a web browser. If the delivery mode is selected to be via text/SMS to the patient's mobile phone, then the content is configured to be most easily viewable on the smaller screen of a mobile device. Further, if the delivery mode is selected so that the content is printed at the printer 130, then the content is configured to be most easily printed.

It should be noted that if the supplemental program is a service, the step of tailoring the content is typically not be performed. However, in some embodiments, the SP module may tailor a confirmation message of the patient's enrollment in the service for delivery to the patient via the specific delivery mode selected and confirmed above.

After the SP module tailors the content for the selected and confirmed delivery mode, the SP module delivers the content of each of the activated supplemental programs to the patient via the selected and confirmed delivery modes, thereby completing step 820. Generally, the central portion 301 of the SP module will delivery the content if the selected delivery mode is to the patient's mobile phone, email, or mailing address. However, if the selected delivery mode is for the content to be printed at the printer 130, then the central portion 301 of the SP module will transmit the content to the SP widget 302 residing on the HCP system 100, and the SP widget 302 thereby effectuates the printing of the content by a printer 130 of the HCP system 100.

As noted above, according to one embodiment of the present invention, one or both of steps 819 and 820 may be considered part of the activation step performed by the SP module. However, as also noted above, the invention is not so limited and the processing performed by steps 819 and 820 may also be considered separate, subsequent steps that are performed after the activation step of the SP module.

In one alternate embodiment, the supplemental program data relating to all of the available supplemental programs resides on the SP system 300 in its one or more databases. In such embodiments, the third party vendor system 400 is omitted, and the central portion 301 of the SP module does not have to reach out to the third party vendor system 400 to provide the patient with the documents or enroll the patient in the services.

In another embodiment of the present invention, the third party vendor system 400 may transmit the document directly to the patient or enroll the patient in the service upon receiving the request and the patient delivery module data. Therefore, in such embodiments, the central portion 301 of the SP module does not receive a document or confirmation signal from the third party content provider 400.

Moreover, it should be noted that some of the services require the patient to confirm their enrollment in the service. Therefore, enrollment cannot be fully effectuated by the SP module or the third party vendor system 400. In such instance, the SP module or the third party vendor system 400 would transmit the appropriate confirmation to the patient via the delivery mode chosen by the provider. Thereafter, if the confirmation is received by the SP module, then the SP module would transmit another enrollment signal back to the third party content provider 400. However, if the confirmation is received by the third party content provider 400, then the third party content provider 400 would enroll the patient in the service upon receiving the confirmation from the patient.

Further, in one embodiment of the present invention, a clinical staff personnel may perform the steps initiated by the provider 101. A clinical staff personnel may be a nurse, an office or hospital administrator, or any other personnel involved in the health care industry. In such embodiments, the clinical staff personnel would choose a previously prescribed substance to begin the process. Thereafter, the process would continue as described above, ultimately resulting in the patient receiving a document (e.g., coupon, educational material, etc.) or being enrolled in a service.

Finally, it should be noted that the SP system 300, and specifically the SP module, of the present invention further comprises control and management options for the provider 101 or an administrator of the HCP system 100. Therefore, using the control and management options, the provider 101 or administrator may adjust the look, functionality, and processes of the SP module, including but not limited to, adding, removing, or editing provider and patient preferences, altering the GUIs generated and displayed by the SP module, etc.

Figure 16:
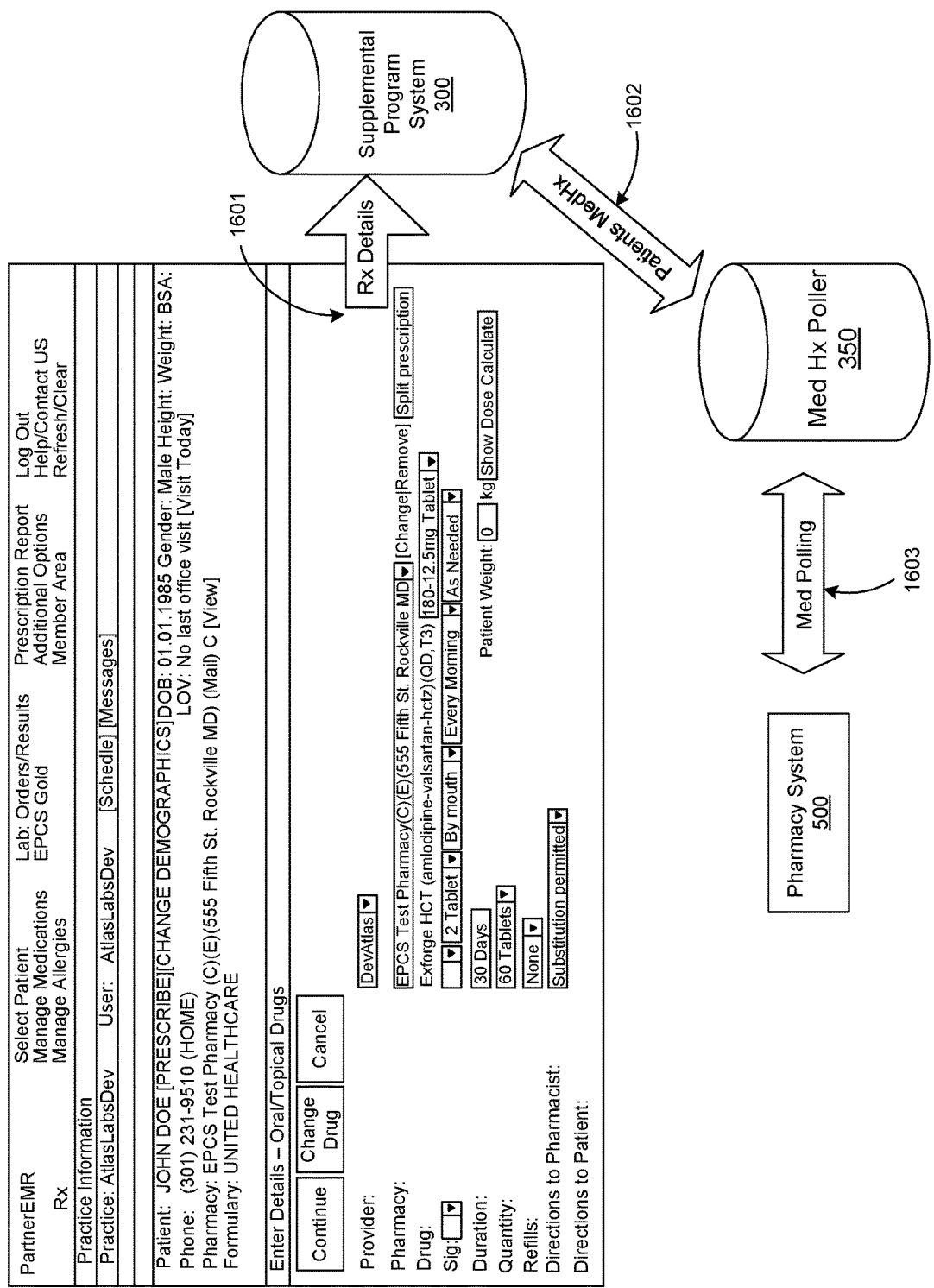
FIG. 16 is a flow diagram of a method of acquiring patient medication history data according to an embodiment of the present invention.

Referring now to FIG. 16, a flow diagram of one method of acquiring patient medication history data according to an embodiment of the present invention is illustrated. As shown, the process begins when the SP module residing on the SP system 300 retrieves data relating to an electronic prescription from the EP module, thereby completing step 1601. This may be accomplished in a manner similar to as discussed above.

Upon receiving the electronic prescription data, the SP module parses the data to determine information relating to the patient, such as, but not limited to the name of the patient, the age of the patient, and other identifying information. Further, the SP module may also parse the electronic prescription data to determine information relating to the prescribed substance, the provider, and/or the payor. Next, the SP module transmits the retrieved patient data (potentially along with other relevant data) to a Medication History Poller System, thereby completing step 1602.

The Medication History Poller System receives and stores the patient data. Next, the Medication History Poller System transmits some of the patient data along with a request for patient medication history information to the pharmacy system 500 and/or the payor system 600, thereby completing step 1603. Thereafter, the Medication History Poller System receives medication history data relating to the patient from the pharmacy system 500 and/or the payor system 600. It should be noted that in other embodiments of the present invention, the Medication History Poller System may be part of the SP module. Further, it should be noted that, as discussed above, the pharmacy system 500 may comprise a prescription routing sub-system 501 (e.g., Surescripts®) and the prescription filling sub-systems 502.

Upon receiving the medication history data relating to the patient, the Medication History Poller System transmits the medication history data relating to the patient back to the SP module residing on the SP system 300. It should be noted that in some embodiments of the present invention, the Medication History Poller System parses and analyzes the medication history data relating to the patient to determine adherence data relating to the patient, including but not limited to, the patient's adherence history in general, the patient's adherence history over a specific time frame, and/or the patient's adherence history in relation to a specific prescribed substance or plurality of prescribed substances for the same disease state.

Upon receiving the medication history data relating to the patient from the Medication History Poller System, the central portion 301 of the SP module uses the patient's medication history data when determining eligibility of each of the plurality of available supplemental programs. Further, the central portion 301 of the SP module may further store the patient's medication history information in either or both of the records database 304 or a patient adherence database residing within the memory 313 of the SP system 300.

Referring now to FIGS. 17-28, event diagrams for supplementing patient and provider interactions to increase patient adherence according to other embodiments of the present invention are illustrated. It should be noted that the diagrams and methods described in reference to FIGS. 17-28 are in no way limiting of the present invention.

Figure 17:
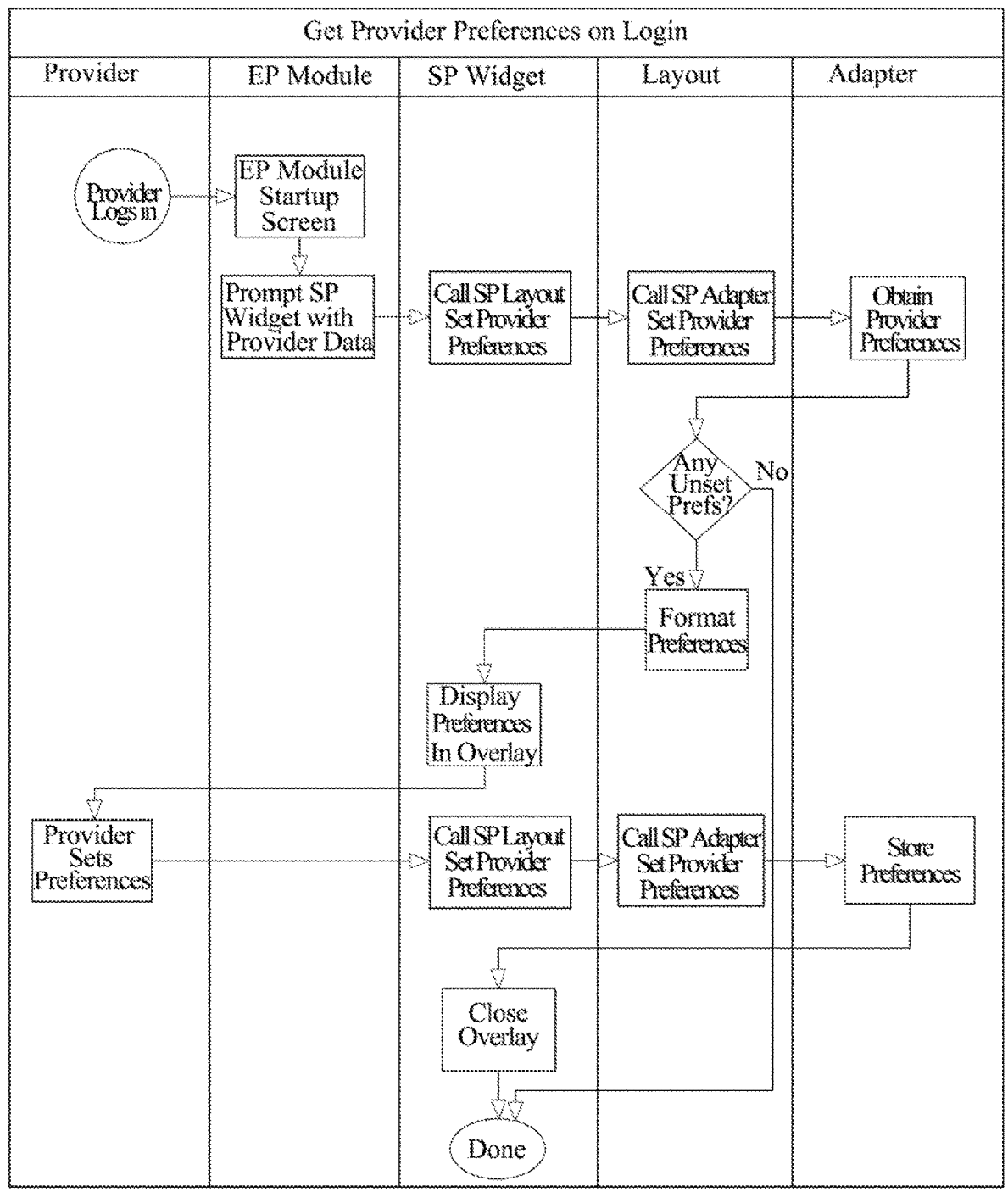
FIGS. 17-28 are event diagrams of methods for supplementing patient and provider interactions to increase patient adherence according to embodiments of the present invention.

Referring to FIG. 17, an event diagram of one method for acquiring provider 101 preference data according to an embodiment of the present invention is illustrated. The method of FIG. 17 begins when the health care provider 101 logs into the EP module using their terminal 120. Thereafter, the EP module displays the startup screen to the provider 101 on the display device 121. Next, the EP module prompts the SP widget 302 to acquire provider preference information from the SP module. Upon being prompted by the EP module, the SP widget 302 calls the central portion 301 of the SP module. Specifically, as exemplified in FIG. 17, the SP widget 302 calls a layout portion of the central portion 301 of the SP module to set the provider's preferences.

According to one embodiment of the present invention, the central portion 301 of the SP module comprises two sub-portions, a layout and an adapter. The layout of the SP module generates the GUIs that are displayed to the provider 101 via the display device 121. The adapter of the SP module performs the transmission and receipt of data between the central portion 301 of the SP module and the other modules and systems of the system 1000.

After being called by the SP widget 302, the layout calls the adapter to set the provider's preferences. Thereafter, the adapter obtains a plurality of different provider preferences offered by the SP module. Next, the layout determines whether any provider preferences had been previously set by the provider 101 by searching the records database 304 of the SP system 300. If all of the preferences have been set by the provider 101, then the process ends. However, if there is at least one unset provider preference, then the layout generates a GUI comprising the unset preferences and transmits the GUI to the SP widget 302. Upon receiving the GUI, the SP widget 302 displays the GUI comprising the unset provider preferences to the provider 101 via the display device 121.

Next, the provider 101 sets their preferences using the input means 122 and via the GUI displayed on the display device 121. Thereafter, the SP widget 302 transmits a signal to the layout to set the provider's preferences. Upon receiving the provider's preferences, the layout calls the adapter to set the provider's preferences, and the adapter stores the provider preference information in the records database 304 of the SP system 300.

Figure 18:
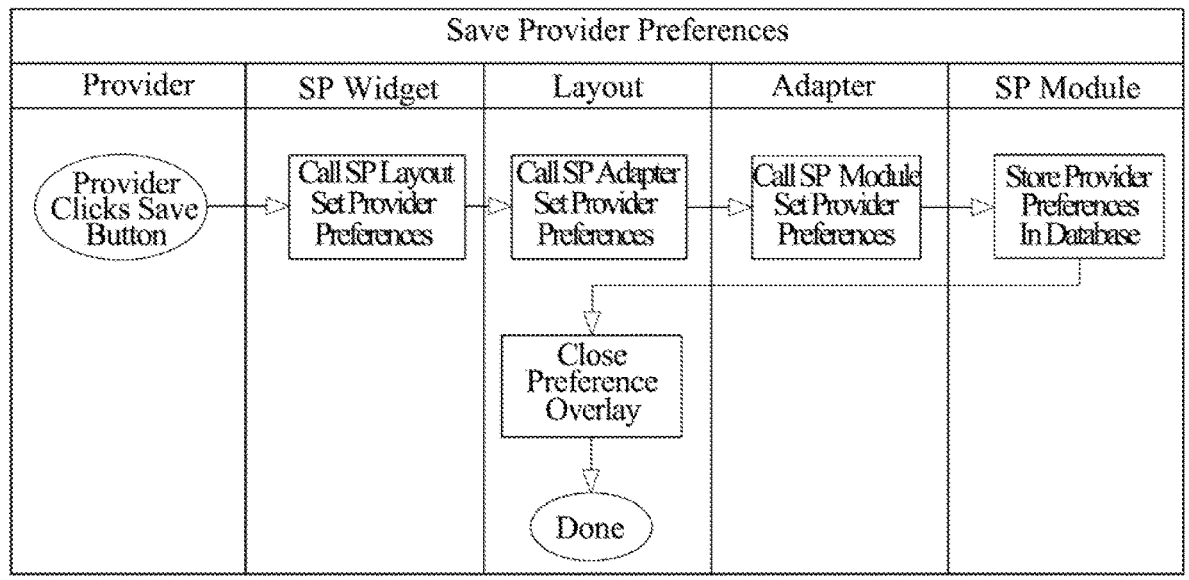

Referring to FIG. 18, an event diagram of one method for storing provider 101 preference data according to an embodiment of the present invention is illustrated. The method begins after the provider 101 selects their preferences in an appropriate GUI generated by the SP module and displayed via the display device 121. After selecting their preferences, the provider 101 actuates a save button on a GUI displayed by the SP widget 302. Actuating the save button causes the SP widget 302 to call the layout of the SP module, which in turn calls the adapter of the SP module, which causes the SP module to store the prescribed preference data in the records database 304.

Figure 19:
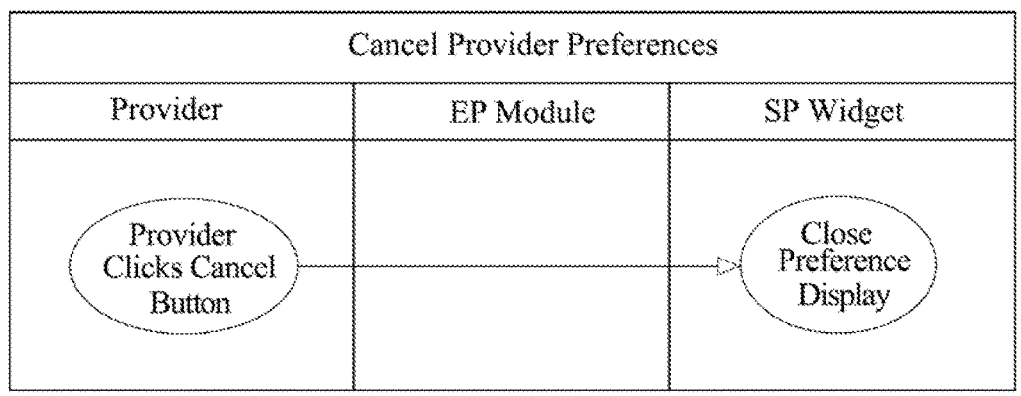

Referring to FIG. 19, an event diagram of one method for cancelling provider 101 preferences according to an embodiment of the present invention is illustrated. The method begins when the provider 101 actuates a cancel button on a GUI displayed by the SP widget 302. This causes the SP widget to close or cancel out of the preference GUI.

Figure 20:
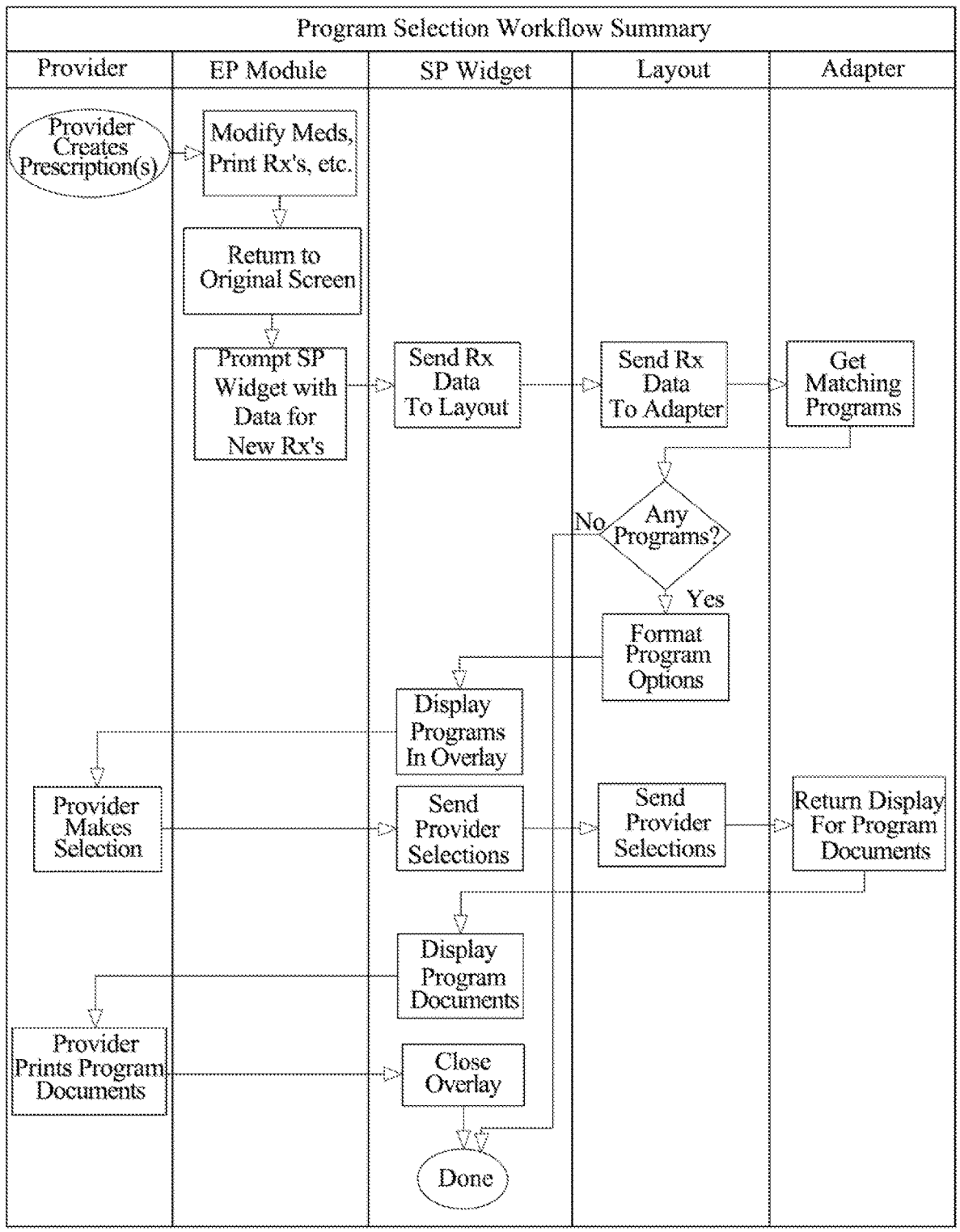

Referring to FIG. 20, an event diagram of one method for selecting supplemental programs according to an embodiment of the present invention is illustrated. The method begins when the provider 101 uses the EP module to create a new electronic prescription for a substance. After creating the electronic prescription, the provider 101 has the ability to modify the prescription using the EP module. Thereafter, the EP module prompts the SP widget 302 with data relating to the electronic prescription. After being prompted by the EP module, the SP widget 302 retrieves electronic prescription data relating to the electronic prescription from the EP module. Upon retrieving the electronic prescription data, the SP widget 302 transmits the data to the layout of the SP module, which in turn transmits the electronic prescription data to the adapter of the SP module.

Upon receiving the electronic prescription data, the adapter determines if there are any programs, out of the plurality of available supplemental programs, for which the patient and the electronic prescription are eligible. If there are not any eligible programs, then the process ends. However, if there are eligible supplemental programs, then the layout of the SP module formats the supplemental program option in a created GUI. Formatting may include a selection of the available delivery modes of each supplemental program and the generation of the GUIs that are to present the eligible supplemental programs to the provider 101. At least one GUI is then displayed by the SP widget 302 to the provider 101, so that the provider 101 may select and confirm which of the eligible supplemental programs they would like activated for the patient.

After the provider 101 makes a selection of eligible supplemental programs, the SP widget 302 transmits the provider's selections to layout of the SP module. The layout then transmits the provider's selection to the adapter. Thereafter, the adapter retrieves the selected supplemental programs from the supplemental program database 303 and transmits the selected eligible supplemental programs to the SP widget 302 for display to the provider 101 via the display device 121. Thereafter, the provider 101 may print the eligible supplemental programs for delivery to the patient.

Figure 21:
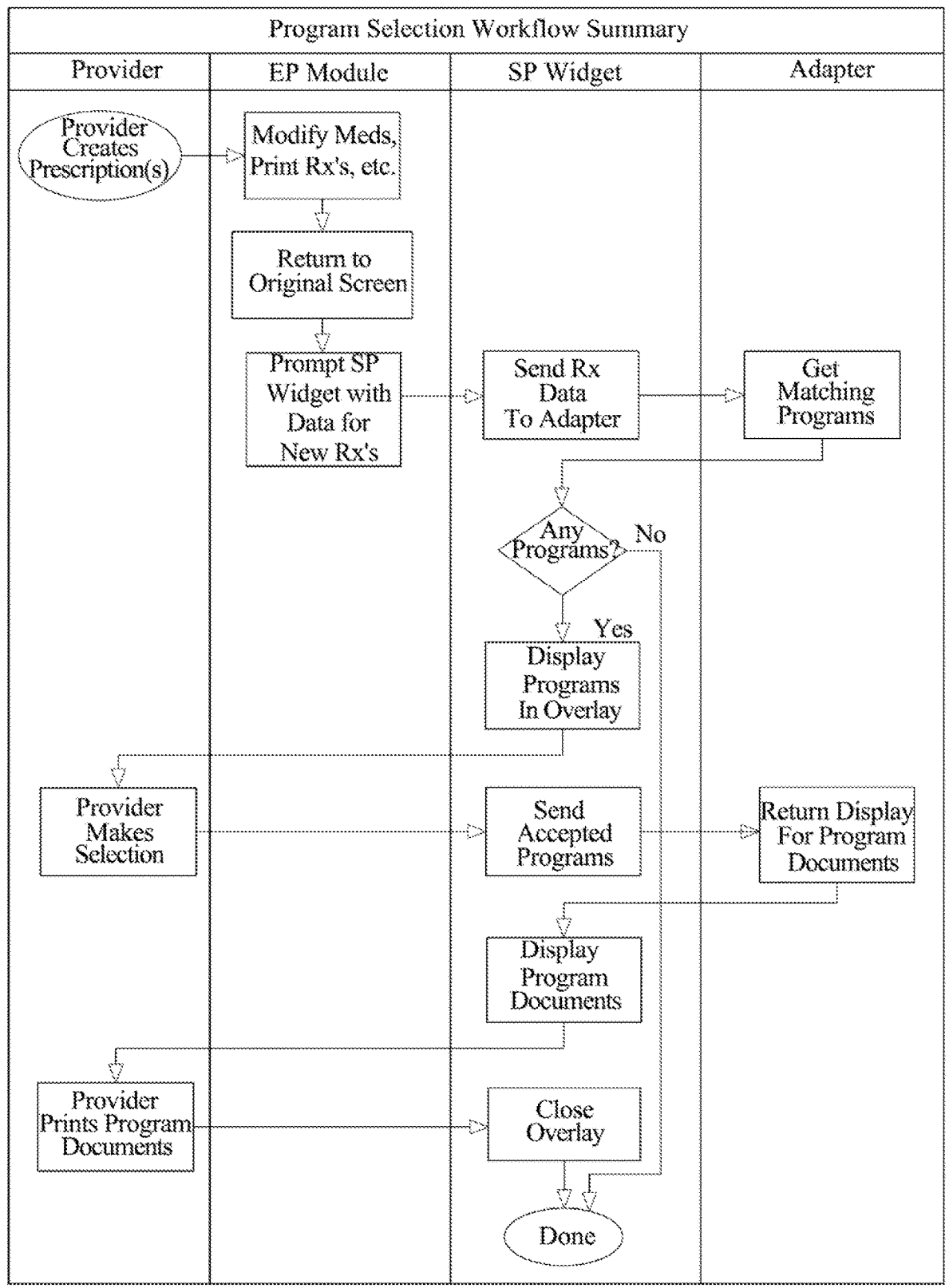

Referring to FIG. 21, an event diagram of another method for selecting supplemental programs according to an embodiment of the present invention is illustrated. The method of FIG. 21 is vastly similar to the method of FIG. 20. It should be noted that processes performed by the layout of the SP module in FIG. 20 are instead performed by the SP widget 302 in the method of FIG. 21. Such a system and method may be preferred to reduce the processing that occurs outside of the HCP system 100.

Figure 22:
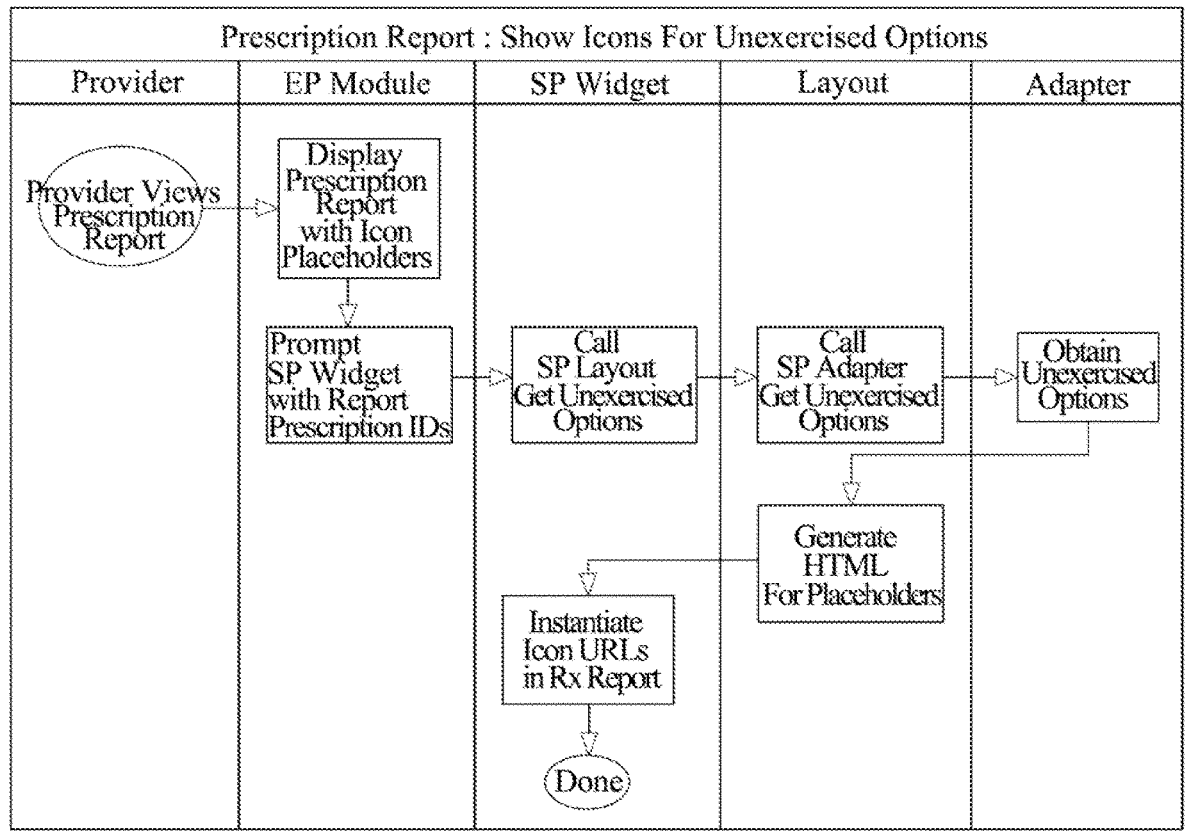

Referring to FIG. 22, an event diagram of one method for presenting unexercised options according to an embodiment of the present invention is illustrated. An unexercised option is an eligible supplemental program that the provider 101 did not select and confirm for activation. In one embodiment, the provider 101 may go back at a later time, and select unexercised options for activation by the SP module. This allows the provider 101 to activate supplemental programs for a patient outside of the prescription writing workflow.

According to one embodiment of the present invention, the method begins when the provider 101 selects and views a prescription report generated and display by the EP module. The EP module displays a prescription report that comprises icon placeholders, the icon placeholders representing prescriptions that the provider 101 previously selected for a subsequent selection of eligible supplemental programs. Next, the EP module prompts the SP widget 302 with report prescription identification data. Although exemplified as being displayed by the EP module, it should be noted that in alternate embodiments, the prescription report may be generated and displayed by the SP module.

Upon receiving the report prescription identification data, the SP widget 302 calls the layout of the SP module for the unexercised options that relate to each of the prescriptions identified by the report prescription identification data. Thereafter, the adapter obtains the unexercised options off the identified prescriptions, and the layout generates Hyper-Text Markup Language (HTML) for placeholders for the unexercised options. Finally, the SP widget 302 instantiates icon Uniform Resource Locators (URLs) for the prescription report.

Figure 23:
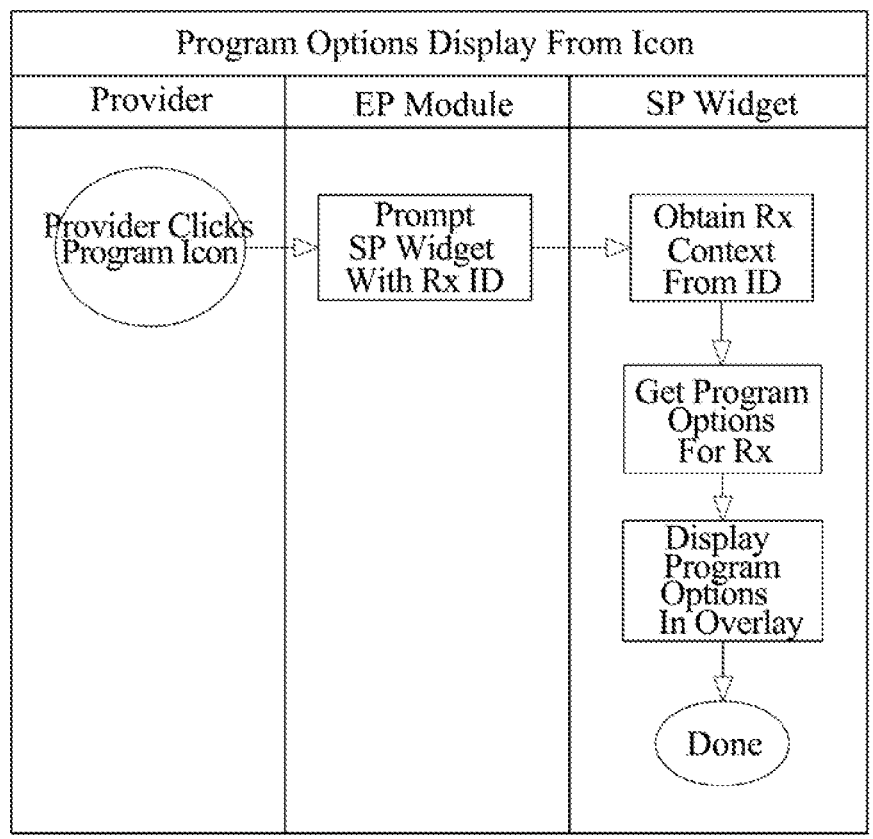

Referring to FIG. 23, an event diagram of one method for displaying supplemental program options according to an embodiment of the present invention is illustrated. This process begins when the provider 101 actuates a program icon from the prescription report, discussed above with reference to FIG. 22. The EP module receives the provider's input and prompts the SP widget 302 with the prescription identification. The SP widget 302 then obtains the prescription content from the prescription identification, retrieves the supplemental program options for the prescription and displays the supplemental program options to the provider 101 in an overlay, similar to that exemplified in FIG. 15. It should be noted that the SP widget 302 does not have to reach back out to the central portion of the SP module, because in such embodiments, the SP widget 302 comprises local memory in which the program options are stored.

Figure 24:
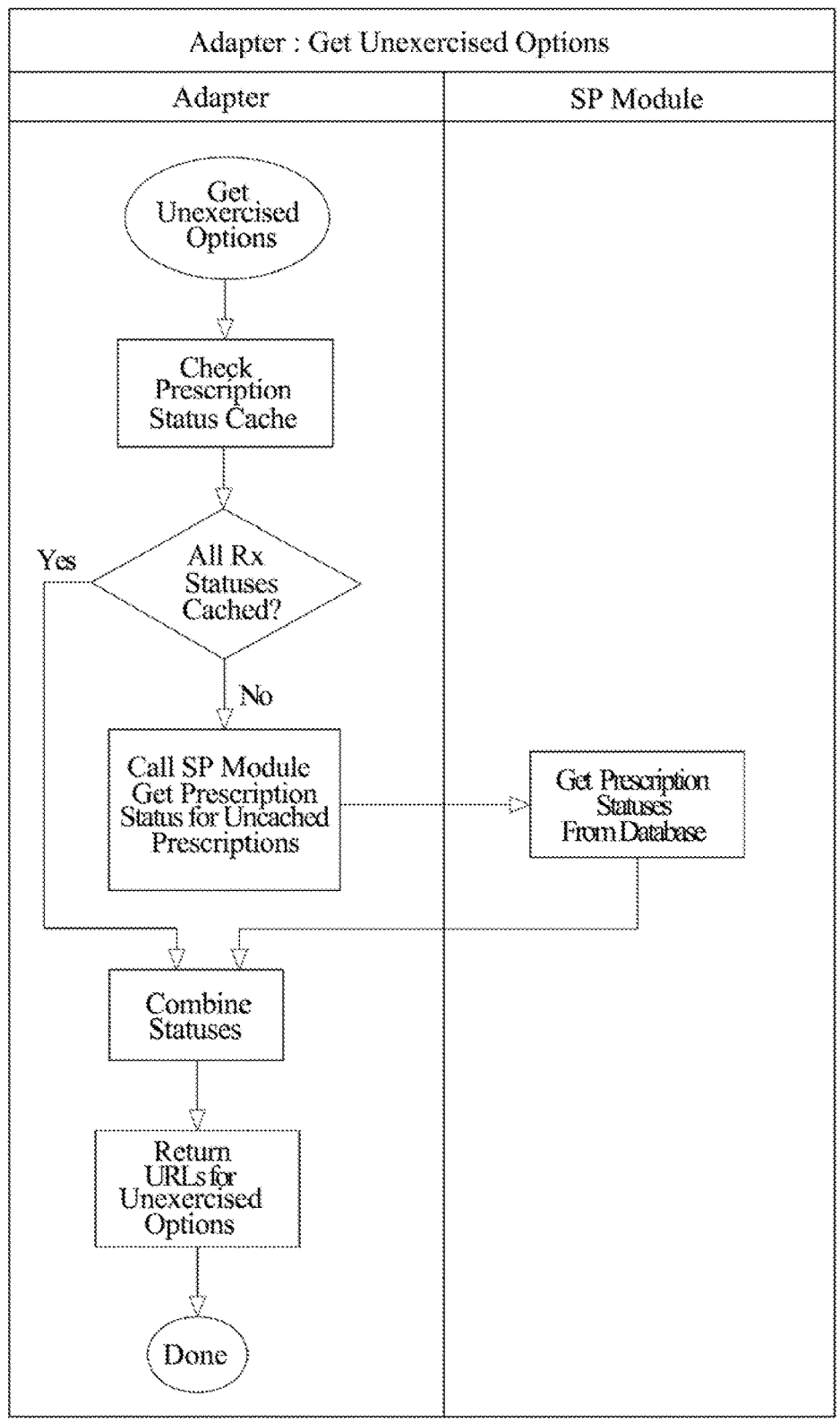

Referring to FIG. 24, an event diagram of one method of the adapter acquiring unexercised options according to an embodiment of the present invention is illustrated. The method exemplified in FIG. 24 is used when the SP widget 302 does not have stored the unexercised options of the prescriptions identified in the prescription report cached locally on the HCP system 100. As shown, the method of FIG. 24 begins with the adapter retrieving the unexercised options. Next, the adapter of the SP module checks to see if the prescription statuses are cached, and determines whether all the prescriptions have statuses that are cached. If not, then the adapter calls the SP module to get prescription statuses for all uncached prescriptions, and the SP module retrieves the prescription statuses from the records database 304. Thereafter, the adapter combines the statuses of the prescriptions and returns URLs for the unexercised options of each of the electronic prescriptions to the SP widget 302 for provider input.

Figure 25:
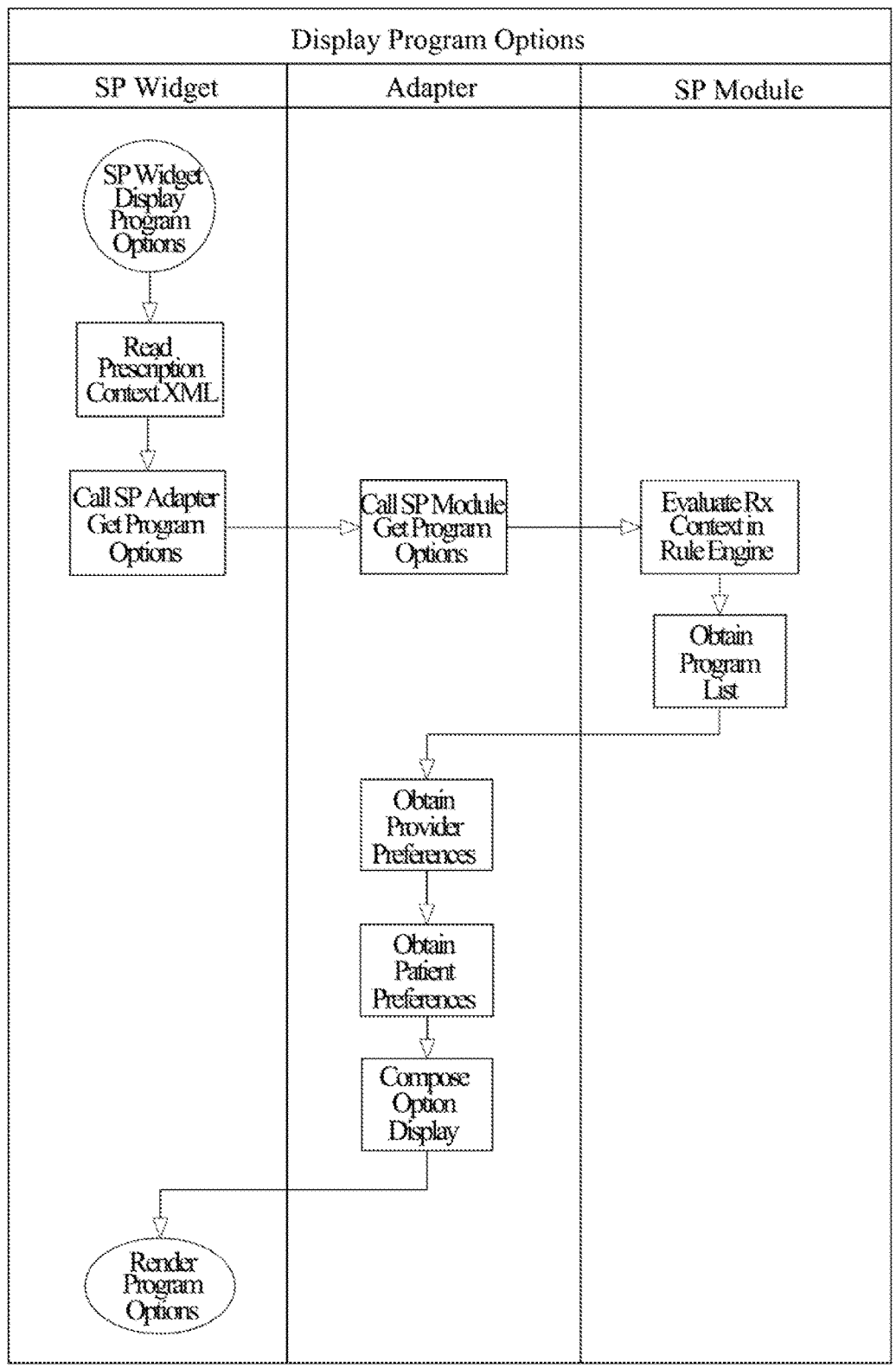

Referring to FIG. 25, an event diagram of one method for displaying supplemental program options according to an embodiment of the present invention is illustrated. The method begins with the SP widget 302 displaying supplemental program options to the provider 101 via the display device 121. The SP widget 302 then reads the electronic prescription context XML and calls the adapter of the central portion 301 of the SP module to get the options for the supplemental program. The SP module then evaluates the prescription context using the rules engine to obtain a list of eligible supplemental programs for the electronic prescriptions. After a list is obtained, the SP module obtains preference data relating to the provider 101 and the patient and composes a display for the supplemental program options. Finally, the SP widget receives a GUI comprising the supplemental program options and displays the GUI to the provider 101 via the display device 121.

Figure 26:
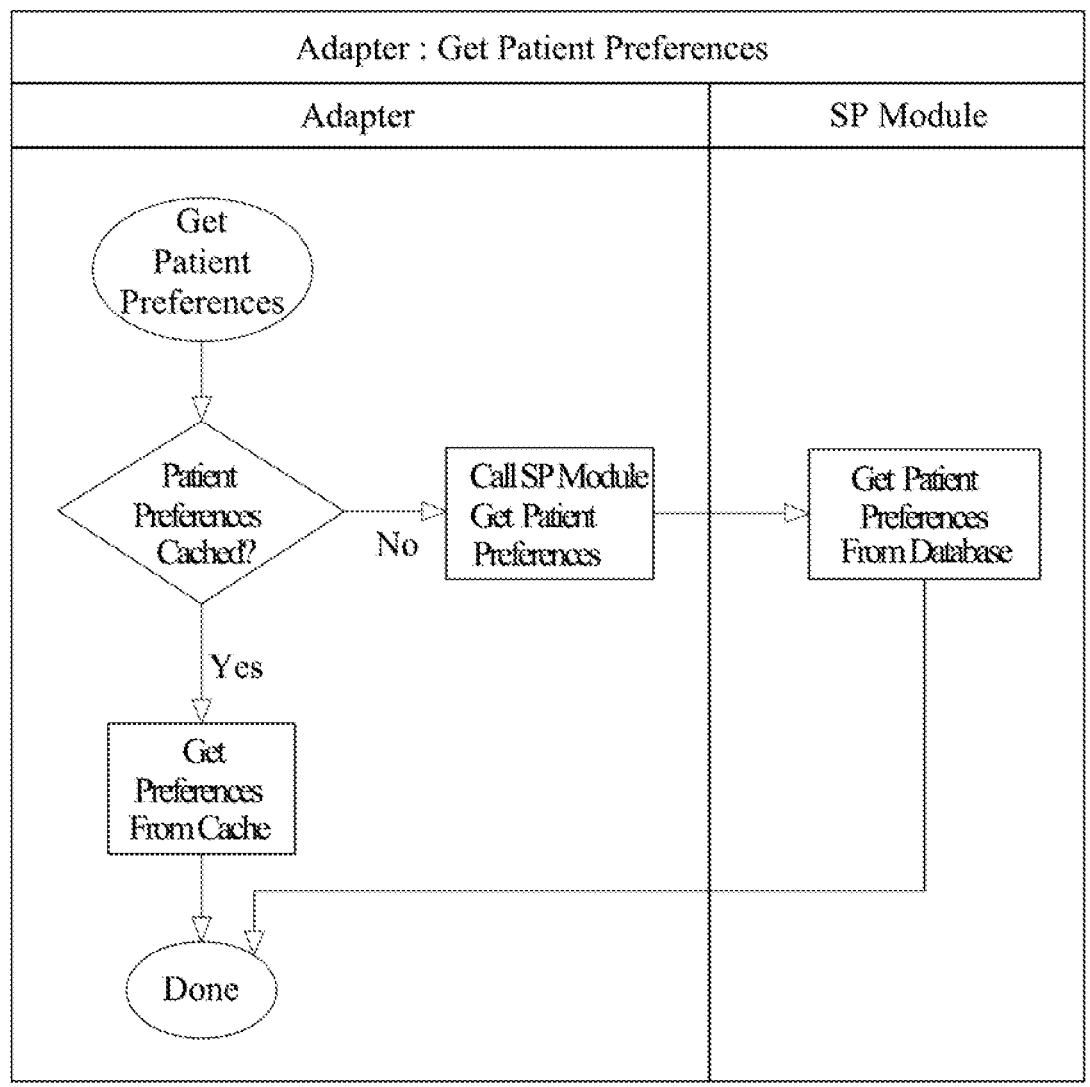

Referring to FIG. 26, an event diagram of one method for acquiring patient preference data according to an embodiment of the present invention is illustrated. The method begins with the adapter of the SP module receiving a request for patient preference data from the SP widget 302. The adapter determines whether the patient preferences are cached, and if so the adapter retrieves the patient preferences from the cached memory. If not, then the adapter retrieves the patient preferences from the record database 304.

Figure 27:
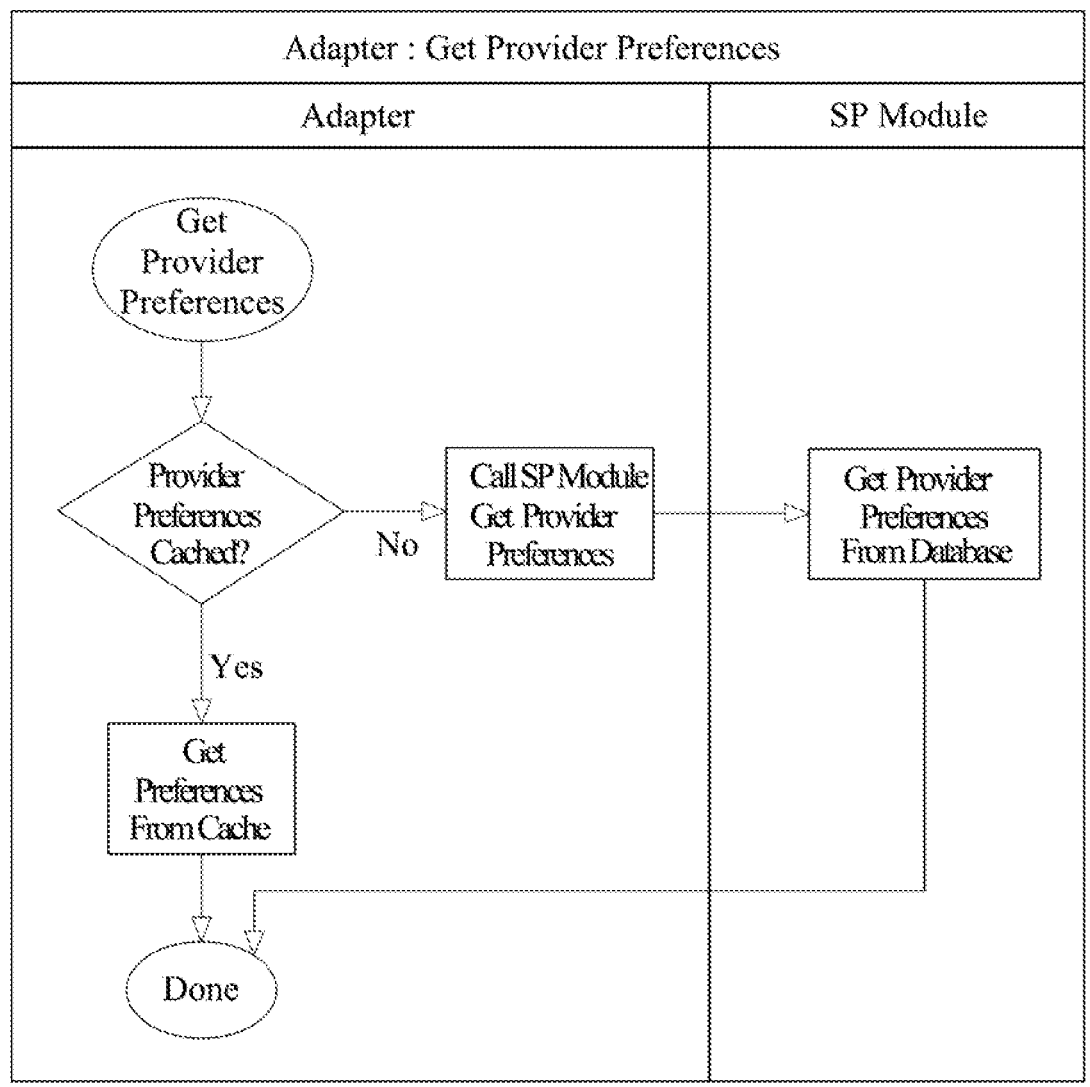

Referring to FIG. 27, an event diagram of another method for acquiring provider 101 preference data according to an embodiment of the present invention is illustrated. The method of FIG. 27 is very similar to that of FIG. 26. The method begins with the adapter of the SP module receiving a request for provider preference data from the SP widget 302. The adapter determines whether the provider preferences are cached, and if so the adapter retrieves the provider preferences from the cached memory. If not, then the adapter retrieves the provider preferences from the record database 304.

Figure 28:
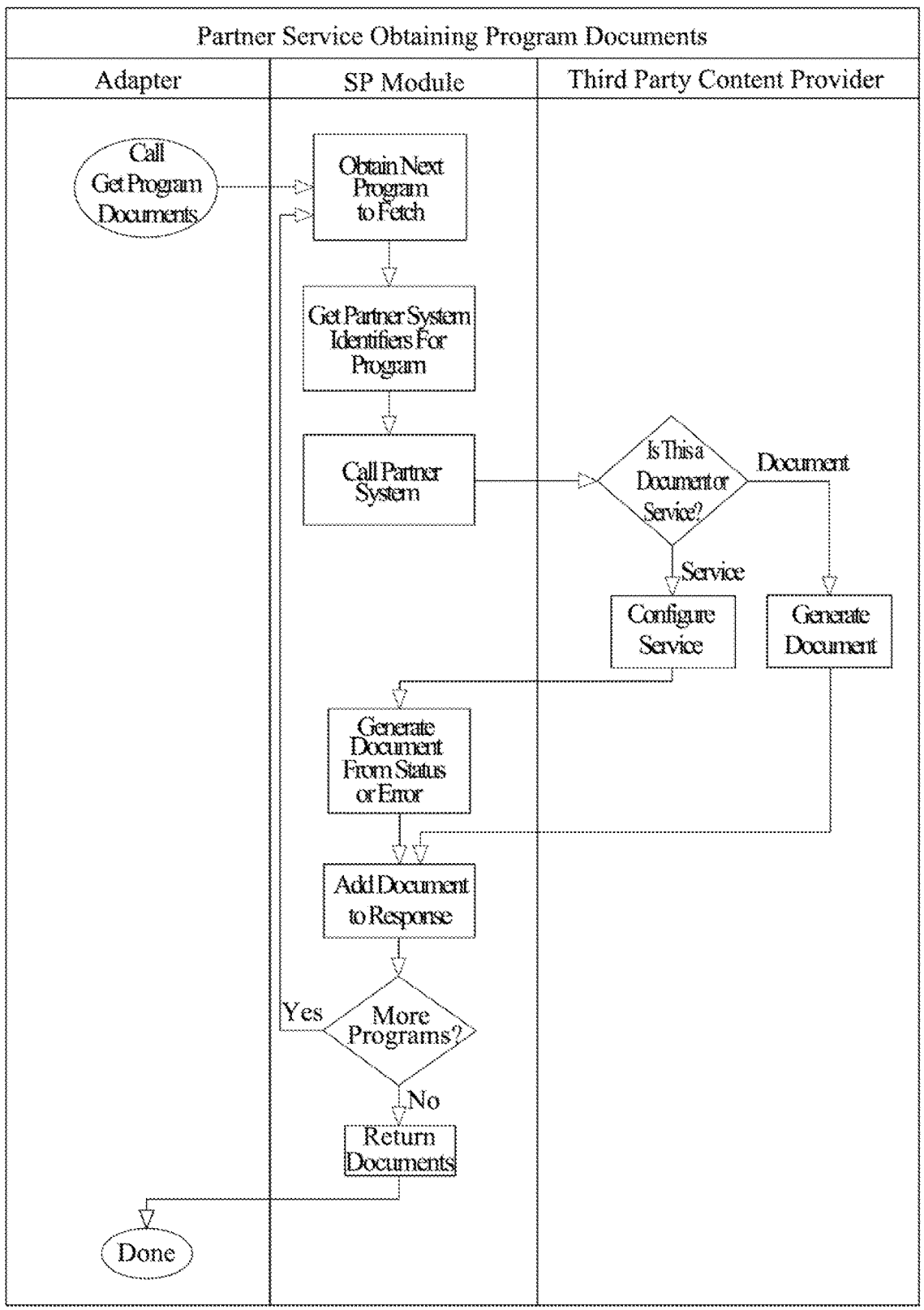

Referring to FIG. 28, an event diagram of one method for acquiring supplemental programs from a third party content provider 400 according to an embodiment of the present invention is illustrated. The method begins with the adapter calling the SP module for supplemental program documents that have been selected and confirmed by the provider 101. The SP module obtains one supplemental program at a time. The SP module first determines which supplemental program to fetch and then retrieves the third party content provider 400 identifiers for that particular supplemental program. The identifiers comprise information relating to the third party content provider 400 that stores the supplemental program. After retrieving the identifiers, the SP module calls the third party content provider system 400.

Upon receiving the signal from the SP module, the third party content provider 400 determines whether the request is for a document or a service based on the identifier of the supplemental program. If the request is for a document, then the third party content provider 400 generates the document. If the request is for a service, then the third party content provider 400 configures the service for the patient. Thereafter, the third party content provider 400 transmits a response to the SP module. The SP module then adds the document to a response and repeats the process for each of the supplemental programs that were selected and confirmed by the provider 101. After documents for all of the supplemental programs has been received by the SP module, the SP module returns the documents to the adapter, which in turn returns the documents to the SP widget 302 for presentation to the provider 101 via display device 121 and provider input.

Figure 29:
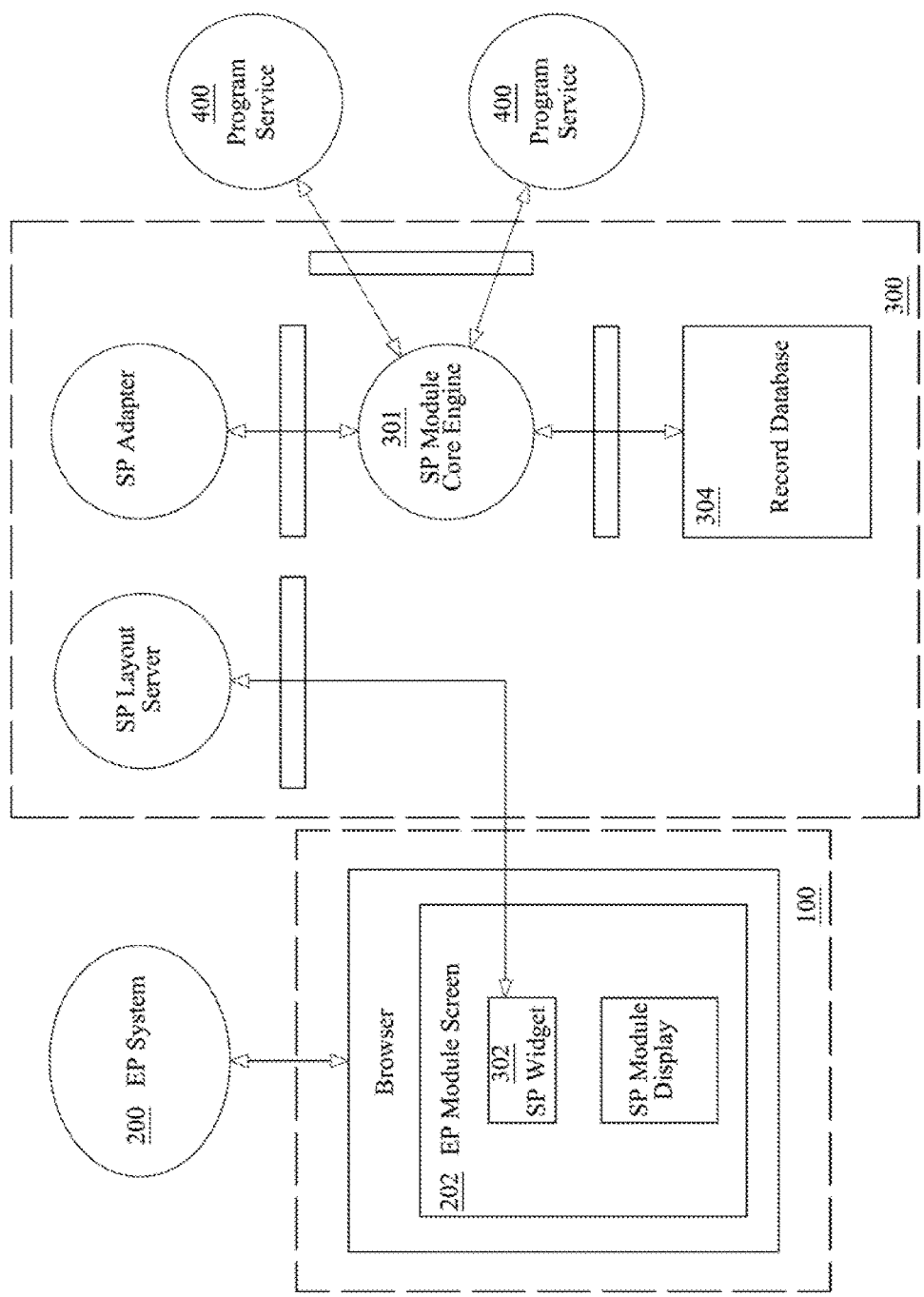
FIG. 29 is a schematic diagram of a system for increasing patient adherence through the activation of supplemental programs according to one embodiment of the present invention.

Referring to FIG. 29, a schematic diagram of a system for increasing patient adherence through the activation of supplemental programs according to another embodiment of the present invention is illustrated. As shown, the system comprises an HCP system 100, an EP system 200, an SP system 300, and third party content providers 400.

EduSave™

Referring to FIG. 9, an EduSAVE™ 900 document according to one embodiment of the present invention is illustrated. The EduSAVE™ 900 document is one type of combined educational coupon document and comprises a general information section 901, an educational information section 902, and a coupon section 903. The general information section 901 may comprise information relating to the health care provider 101 who issued the prescription for the patient, information relating to the patient, information relating to the pharmacy filling sub-system 502, and/or information relating to the patient's payor (e.g., health insurance company). The educational information section 902 comprises either general and/or specific information relating to the substance being prescribed and/or the disease state of the patient for which the substance is being prescribed. Finally, the coupon section 903 comprises coupon information relating to a discount, a rebate, or a voucher for the patient for the substance being prescribed. Although described as combining general information, educational information, and coupon information, it should be noted that in alternate embodiments of the present invention, the EduSAVE™ 900 document may comprises just educational information and coupon information, or any combination of health care provider 101 information, patient information, payor information, and pharmacy information along with educational information and coupon information.

One reason the EduSAVE™ 900 document is beneficial is because it provides for a single document that comprises both educational information and coupon information. Therefore, when the patient brings the EduSAVE™ 900 document to their pharmacy for redemption of the coupon, they are encouraged to read the educational information provided therewith. Further, if the patient has any questions or concerns regarding the substance after they have left the provider's office, the patient may easily access the provider's contact information on the EduSAVE™ 900 document.

According to one embodiment of the present invention, after an electronic prescription for the substance is created by a health care provider 101, the SP widget 302 retrieves data relating to the electronic prescription from the thin-client portion of the EP module 203. The SP widget 302 then transmits the electronic prescription data to the central portion 301 of the SP module residing on the SP system 300, such that the central portion 301 of the SP module receives the electronic prescription data. The electronic prescription data comprises first patient data that is specific to the patient, first prescribed substance data that is specific to the prescribed substance, first provider data that is specific to the provider 101, and first payor data that is specific to the payor. It should be noted that the specifics of the electronic prescription data are discussed in detail above.

However, the invention is not so limited, and in an alternate embodiment of the present invention, the electronic prescription data may not relate to an electronic prescription currently being prescribed by a health care provider 101 for a patient, but rather relate to a refill, a renewal, or a previously prescribed substance. In such embodiments, the electronic prescription data may be received by the SP module from one of the other databases of the system 1000 (e.g., the EP database 201, the records database 304, the patient prescription history database 505, etc.). Stated another way, the electronic prescription data may, but does not necessarily have to be generated by a health care provider 101.

Once the central portion 301 of the SP module receives the electronic prescription data, the central portion 301 of the SP module retrieves additional data prior to determining educational data and coupon data for the prescribed substance. The additional (or second) data may comprise one or more of patient data, prescribed substance data, provider data, and payor data. Further, the additional (or second) patient data may comprise patient adherence data. According to one embodiment of the present invention, the additional (or second) data is retrieved by the SP module from the records database 304 of the SP system 300. However, it should be noted that the invention is not so limited and in alternate embodiments, the central portion 301 of the SP module may only retrieve a portion of the data listed herein or may not retrieve any additional data prior to determining educational data and coupon data for the prescribed substance.

After receiving electronic prescription data, and possibly after retrieving additional data from the records database 304, the SP module determines educational data relating to the prescribed substance and coupon data relating to the prescribed substance. In one embodiment of the present invention, the determination is accomplished by the central portion 301 of the SP module in response to receiving the electronic prescription data. Thus, it may be said that the SP module determines the educational data and coupon data automatically upon receiving electronic prescription data according to one embodiment of the present invention. In one embodiment of the present invention, the determination of both the educational data and coupon data comprises the central portion 301 of the SP module searching one or more databases, such as the supplemental program database 303 or one of the databases 401, 402, 403, 404 of the appropriate third party content provider 400, for educational data and coupon data both relating to the prescribed substance. It should be noted that the determination of both the educational data and coupon data may be accomplished by the central portion 301 of the SP module using any combination of the first patient data, first prescribed substance data, first provider data, and first payor received from the electronic prescription data, potentially along with any of the additional (or second) data (patient data, prescribed substance data, provider data, and payor data) retrieved by the SP module.

In one embodiment of the present invention, the determination of educational data and coupon data for the prescribed substance requires the central portion 301 of the SP module to determine both educational data and coupon data for which the patient is eligible based on the electronic prescription. This is similar to as discussed above with reference to the determination of eligible supplemental programs. Therefore, in such embodiments, the educational data and coupon data may comprise rules that must be met in order for the educational data and coupon data to be eligible for the electronic prescription of the patient. Thus, in accordance with one embodiment of the present invention, the determination of both the educational data and coupon data may be accomplished by the SP module in a manner similar to as discussed above with reference to supplemental programs (FIG. 8a and steps 806-808).

However, the invention is not so limited, and in another embodiment of the present invention, the SP module simply transmits any combination of data (electronic prescription data and additional, retrieved data) to a third party system. This, in turn, causes the third party system to determine the educational data and/or the coupon data upon receiving the appropriate data from the SP module. Thus, in this embodiment of the present invention, the third party system determines the educational data and/or the coupon data that relates to the prescribed substance. Finally, upon determining the educational data and/or the coupon data, the third party system transmits the educational data and/or the coupon data to the SP module. Therefore, it may be said that the central portion 301 of the SP module receives the educational data and/or the coupon data from one or more of the databases 401, 402, 403, 404 of the appropriate third party content provider 400.

Upon determining the educational data and coupon data that relates to the prescribed substance, the central portion 301 of the SP module retrieves from one or more databases, such as the supplemental program database 303 or one of the databases 401, 402, 403, 404 of the appropriate third party content provider 400, the educational data and the coupon data. Thereafter, the central portion 301 of the SP module combines the educational data and the coupon data into a single data file, which may be considered a combined educational coupon since the file comprises both educational data and coupon data. It should be noted that when the central portion 301 of the SP module combines the educational data and the coupon data into a single data file, the central portion 301 of the SP module may combine a portion of or the entirety of the educational data and/or coupon data. Thus, the single data file may comprise just a portion of either or both of the educational data and the coupon data. Further, in one embodiment of the present invention, the single data file may be a text-based file, an image-based file, or a combined text and image based file. One example of a combined educational coupon is the EduSAVE™ 900 document exemplified in FIG. 9.

Further, in one embodiment of the present invention, prior to generating a single data file comprising the educational data and the coupon data, the central portion 301 of the SP module presents to a health care provider 101, in the display device 121, a list of the education data and the coupon data for selection and acceptance by the health care provider 101. Thereafter, the central portion 301 of the SP module generates the single data file, or the combined educational coupon, upon both the educational data and the coupon data being selected and accepted by the health care provider 101. It should be noted that this may be accomplished in any manner discussed above with reference to steps 811-814 of FIG. 8b. Finally, in one embodiment of the present invention, the central portion 301 of the SP module determines more than one separate portion of educational data and/or coupon data and presents the one or more educational data and/or coupon data to the health care provider 101 in a list via the display device 121. Thereafter, the health care provider 101 may select one or more of the educational data and/or coupon data, and the central portion 301 of the health care provider 101 combines the one or more of the educational data and/or coupon data into a single data file, the single data file being a combined educational coupon. Thus, the combined educational coupon is not limited to just one educational data file and one coupon data file, but may comprise more than one educational data file and/or coupon data file. Finally, after generating the combined educational coupon, the central portion 301 of the SP module may then store the combined education coupon in one or more databases (e.g., the records database 304 or the supplemental program database 303) of the SP system 300 for subsequent applications.

Finally, after the central portion 301 of the SP module has generated the single data file comprising the educational data and coupon data relating to the prescribed substance, the central portion 301 of the SP module may transmit the single data file to one or more systems or devices. These include, but are note limited to, a pharmacy filling sub-system 502, an HCP system 100, and a patient computer device. It may be beneficial to transmit the single data file to a pharmacy filling sub-system 502 so that the patient does not have to remember to bring the combined educational coupon with them when picking up the prescription. Rather, the combined educational coupon is waiting for them at the pharmacy filling sub-system 502, such that the pharmacist may automatically deduct the coupon from the purchase price of the prescription and the educational material may be provided to the patient upon receiving their prescription. Further, it may be beneficial to transmit the single data file to the HCP system 100 so that the HCP system 100 may make the combined educational coupon available to patient while they are still in the presence of their health care provider 101. Therefore, if the patient has any questions or concerns, they may immediately speak with their health care provider 101 upon receiving the combined educational coupon. Finally, it may be beneficial to transmit the single data file to a patient computer device, such as a personal computer, smart phone, printer, fax machine, or other electronic device owned or controlled by the patient. This allows the patient to receive and view the combined educational coupon at their convenience.

Nonetheless, it should be noted that in accordance with one embodiment of the present invention, the central portion 301 of the SP module generates a combined educational coupon using the process described above with respect to supplemental programs. In such embodiments, the central portion 301 of the SP module parses out educational information data from an eligible supplemental program that relates to educational material, and coupon data from an eligible supplemental program that relates to a coupon. Thereafter, the central portion 301 of the SP module combines the educational information data and the coupon data, potentially along with other general data (e.g., provider data, patient data, etc.) into a single data file to create the combined educational coupon. Thereafter, the central portion 301 of the SP module may store the combined education coupon in the supplemental program database 303 of the SP system 300 for subsequent applications. Further, after creating the combined educational coupon, the central portion 301 of the SP module may transmit the combined educational coupon to the HCP system 100 as a single data file.

Further, it should be noted that in one embodiment of the present invention, the central portion 301 of the SP module may be considered a non-transitory computer-readable storage medium that is encoded with instructions which, when executed by the processor 311, perform a method of receiving data relating to an electronic prescription of a prescribed substance for a patient; searching one or more databases for educational data relating to the prescribed substance and coupon data relating to the prescribed substance; determining educational data relating to the prescribed substance and coupon data relating to the prescribed substance; retrieving from the one or more databases the educational data relating to the prescribed substance and the coupon data relating to the prescribed substance; and generating a single data file comprising the educational data relating to the prescribed substance and the coupon data relating to the prescribed substance.

Finally, it should be noted that in one embodiment of the present invention, the SP system 300 may be considered a computer system for electronically generating educational coupons for a prescribed substance, which comprises a processor 311; a storage device 313; a network interface 312; and instructions residing on the storage unit 313, which when executed by the processor 311, causes the processor 311 to: a) receive electronic prescription data for a prescribed substance for a patient; b) determine educational data relating to the prescribed substance and coupon data relating to the prescribed substance; and c) generate a single data file comprising the educational data relating to the prescribed substance and the coupon data relating to the prescribed substance.

Tailoring General and Specific Educational Content

As noted above, the supplemental programs comprise both general educational content and specific educational content. In one embodiment of the present invention, the general educational content comprises information relating to the prescribed substance, while the specific educational content comprises information relating, not only to the prescribed substance, but also the specific diagnostic reason(s) that the substance was prescribed to the patient, such as but not limited to, the specific disease(s) for which the substance was prescribed, along with a wide variety of signs, symptoms, abnormal findings, complaints, social circumstances, and external causes of injury or disease for which the substance was prescribed. Thus, the educational content (or material), both general and specific, is tailored to the specific needs and diagnoses of the patient.

Similar to as discussed above and according to one embodiment of the present invention, after an electronic prescription for the substance is created by a health care provider 101, the SP widget 302 retrieves data relating to the electronic prescription from the thin-client portion of the EP module 203. Further, the SP widget 302 may also retrieve a diagnostic code that is entered by the health care provider 101. Specifically, the provider 101 enters a diagnostic code into the SP widget 302 using the input device 122 of the terminal 120. The diagnostic code may be entered prior to, during, or after the creation of the electronic prescription by the health care provider 101.

A diagnostic code is a string of characters and/or numbers that are used to represent medical diseases and/or a wide variety of signs, symptoms, abnormal findings, complaints, social circumstances, and external causes of injury or disease. According to one embodiment, the diagnostic code is entered or provided by the health care provider 101 and provides a more specific reasoning as to why the patient is being prescribed a particular substance. For example, in one embodiment, the diagnostic code is an International Classification of Diseases, Ninth Revision (ICD-9) code entered by the provider 101 during the patient's visit.

After receiving data relating to an electronic prescription and a diagnostic code, the SP widget 302 then transmits the electronic prescription data and the diagnostic code to the central portion 301 of the SP module residing on the SP system 300, such that the central portion 301 of the SP module receives the electronic prescription data and the diagnostic code. It should be noted that the diagnostic code may, but does not necessarily have to be received in conjunction with the electronic prescription data. As discussed in detail above, the electronic prescription data comprises first patient data that is specific to the patient, first prescribed substance data that is specific to the prescribed substance, first provider data that is specific to the provider 101, and first payor data that is specific to the payor. Further, in one embodiment of the present invention, the electronic prescription data further comprises a National Drug Code identifier of the prescribed substance. The National Drug Code identifier is a unique product identifier for prescribed substances that are intended for human use. Finally, it should be noted that in one embodiment of the present invention, the electronic prescription data comprises the diagnostic code.

Further, in an alternate embodiment of the present invention, the electronic prescription data does not relate to an electronic prescription currently being prescribed by a health care provider 101 for a patient, but rather relates to a refill, a renewal, or a previously prescribed substance. In such embodiments, the electronic prescription data may be received by the SP module from one of the other databases of the system 1000 (e.g., the EP database 201, the records database 304, the patient prescription history database 505, etc.). Stated another way, the electronic prescription data may, but does not necessarily have to be generated by a health care provider 101.

Once the central portion 301 of the SP module receives the electronic prescription data and the diagnostic code, the central portion 301 of the SP module retrieves additional data prior to determining general and specific educational data. As discussed in more detail above, the additional (or second) data may comprise one or more of patient data, prescribed substance data, provider data, and payor data. Further, the additional (or second) patient data may comprise patient adherence data. According to one embodiment of the present invention, the additional (or second) data is retrieved by the SP module from the records database 304 of the SP system 300. However, it should be noted that the invention is not so limited and in alternate embodiments, the central portion 301 of the SP module may only retrieve a portion of the data listed herein or may not retrieve any additional data prior to determining general and specific educational data.

After receiving electronic prescription data and the diagnostic code, and possibly after retrieving additional data from the records database 304, the central portion 301 of the SP module searches one or more databases, such as the supplemental program database 303 or one of the databases 401, 402, 403, 404 of the appropriate third party content provider 400, for general educational data and specific educational data both relating to the prescribed substance. The general educational data relates to the prescribed substance, but is independent of the diagnostic code. Thus, the general educational data comprises broad and wide-ranging information that relates generally to the prescribed substance or the disease state for which the substance was prescribed to the patient. For example, general educational data may comprise information relating to high blood pressure in general.

By contrast, the specific educational data relates to the prescribed substance and is based on the received diagnostic code. Thus, the specific educational data comprises specific information about the particular prescribed substance or the disease state of the prescribed substance, and is particular to the exact reasons for which the provider 101 has written the prescription for the patient. For example, specific educational data may comprise information relating to malignant hypertension or renal hypertension, whereby the general educational data simply relates to high blood pressure in a broader or more general sense. Stated another way, the specific educational content may relate to one or more of the specific disease(s) for which the substance was prescribed, and/or the signs, symptoms, abnormal findings, complaints, social circumstances, and/or external causes of injury or disease for which the substance was prescribed to the patient. Further, as discussed in detail above, the educational data (both general and specific) may relate to an educational document or an educational service, as discussed above in more detail.

It should be noted that the determination of both the general and specific educational data may be accomplished by the central portion 301 of the SP module using any combination of the diagnostic code, the first patient data, first prescribed substance data, first provider data, and first payor received from the electronic prescription data, potentially along with any of the additional (or second) data (patient data, prescribed substance data, provider data, and payor data) retrieved by the SP module. Further, in one embodiment of the present invention, the general educational data is searched using the National Drug Code identifier, along with any combination of the electronic prescription data and retrieved data discussed above. Similarly, it should be noted that the specific educational data is searched using the diagnostic code received by the central portion 301 of the SP module, along with any combination of the electronic prescription data and retrieved data discussed above.

In one embodiment of the present invention, in order for the central portion 301 of the SP module to determine both the general educational data and the specific educational data, the central portion 301 of the SP module must also determine which general and specific educational data the patient is eligible for based on the electronic prescription. This is similar to as discussed above with reference to the determination of eligible supplemental programs. Therefore, in such embodiments, the general educational data and the specific educational data may comprise rules that must be met in order for the general educational data and the specific educational data to be eligible for the electronic prescription of the patient. Moreover, in accordance with one embodiment of the present invention, the determination of both the general educational data and the specific educational data may be accomplished by the central portion 301 of the SP module in a manner similar to as discussed above with reference to supplemental programs (FIG. 8a and steps 806-808).

However, the invention is not so limited, and in another embodiment of the present invention, the SP module simply transmits any combination of data (electronic prescription data, diagnostic code, National Drug Code identifier, and additional, retrieved data) to a third party system. This, in turn, causes the third party system to determine the general educational data and/or the specific educational data upon receiving the appropriate data from the SP module. Thus, in this embodiment of the present invention, the third party system determines the general educational data and/or the specific educational data that relates to the prescribed substance. Finally, upon determining the general educational data and/or the specific educational data, the third party system transmits the general educational data and/or the specific educational data to the SP module. Therefore, it may be said that the central portion 301 of the SP module receives the general educational data and/or the specific educational data from one or more of the databases 401, 402, 403, 404 of the appropriate third party content provider 400.

Upon determining the general educational data and the specific educational data that relates to the prescribed substance and the diagnostic code, the central portion 301 of the SP module retrieves from one or more databases, such as the supplemental program database 303 or one of the databases 401, 402, 403, 404 of the appropriate third party content provider 400, the general educational data and the specific educational data. According to one embodiment of the present invention, the central portion 301 of the SP module retrieves two data files, a first data file that is the general educational data and a second data file that is the specific education data. Thereafter, the central portion 301 of the SP module may combine the first data file (general educational data) and the second data file (specific educational data) into a single data file, thus creating a single data file that comprises both general educational data and specific educational data. It should be noted that when the central portion 301 of the SP module combines the general and specific educational data into a single data file, the central portion 301 of the SP module may combine a portion of or the entirety of the general educational data and the specific educational data. Thus, the single data file may comprise just a portion of either or both of the general and specific educational data. Moreover, according to one embodiment of the present invention, the central portion 301 of the SP module may combine one or more general education data file with one or more specific educational data file. However, it should be noted that the invention is not so limited, and in some embodiments of the present invention, the general educational data and the specific educational data is not combined into a single data file.

Further, in one embodiment of the present invention, the central portion 301 of the SP module presents to a health care provider 101, in the display device 121, a list that comprises the general education data and the specific educational data for selection and acceptance by the health care provider 101. In such embodiments, each of the general education data and the specific education data presented in the display device 121 is selectable and de-selectable by the health care provider 101 using the input device 122. It should be noted that the display of the list and the selection and acceptance of the general and specific educational data may be accomplished in any manner similar to as discussed above with reference to supplemental programs in steps 811-814 of FIG. 8b. Further, it should be noted that the list is not limited to only one general educational data file and one specific educational file, but rather may include any number of general and/or specific educational files for selection and acceptance by the health care provider 101.

According to one embodiment of the present invention, after a list of the general education data and the specific educational data is presented in the display device 121 to the health care provider 101 for provisioning to the patient, the central portion 301 of the SP module makes the general educational data and the specific educational data that is selected and confirmed by the health care provider 101 available to the patient. In one embodiment, this is accomplished by the SP module transmitting the general education data and the specific educational data that is selected and confirmed by the health care provider 101 to a patient computer device. This may be accomplished using at least one of email, SMS. WAP, and a mobile application.

Therefore, the diagnostic code may be used, in addition to the electronic prescription data and any additional retrieved data, by the central portion 301 of the SP module to determine if there is both general educational data and specific educational data for which the patient is eligible. Therefore, by using a diagnostic code (e.g., the ICD-9 code) to determine if there is any eligible specific educational data relating to why the prescribed substance was prescribed to the patient, the present invention may provide both general and specific educational material to the patient. For instance, the patient may receive general information relating to the substance they are being prescribed or the disease state in which they are diagnosed, while also receiving specific educational material directed to the specific reason(s) the patient has been prescribed the particular substance. This is beneficial because the educational documents and/or services help the patient in understanding not only their general health concerns and prescribed substances, but also their specific health concerns along with their specific diagnoses. Thus, the educational material (both general and specific) that is made available to the patient may be tailored to the specific needs and diagnoses of the patient.

Further, it should be noted that in one embodiment of the present invention, the central portion 301 of the SP module may be considered a non-transitory computer-readable storage medium that is encoded with instructions which, when executed by the processor 311, perform a method of receiving electronic prescription data for a prescribed substance for a patient, said electronic prescription data including a diagnostic code; searching one or more databases to determine: (1) general educational data relating to the prescribed substance independent of the diagnostic code; and (2) specific educational data relating to the prescribed substance based on the diagnostic code; and presenting to a health care provider, in a display device, a list of the general educational data and the specific educational data determined in step b) for provisioning to the patient.

Finally, it should be noted that in one embodiment of the present invention, the SP system 300 may be considered a computer system for electronically generating educational coupons for a prescribed substance, which comprises a processor 311; a storage device 313; a network interface 312; and instructions residing on the storage unit 313, which when executed by the processor 311, causes the processor 311 to: a) receive electronic prescription data for a prescribed substance for a patient, said electronic prescription data including a diagnostic code; b) search one or more databases to determine: (1) general educational data relating to the prescribed substance independent of the diagnostic code; and (2) specific educational data relating to the prescribed substance based on the diagnostic code; and c) present to a health care provider, in a display device, a list of the general educational data and the specific educational data determined in step b) for provisioning to the patient.

Method of Using Cohorts to Determine Effectiveness of Supplemental Programs

According to another embodiment of the present invention, the system 1000 described above may be used to determine the effectiveness of supplemental programs on patient adherence through the use of a plurality of cohorts. Generally, as used herein, a cohort is a group of health care providers 101 who activate the same supplemental programs for a particular prescribed substance. As discussed in more detail below, in accordance with one embodiment of the present invention a plurality of cohorts, each comprising different permutations (or groupings) of supplemental programs, are used to determine the respective effectiveness of the different permutations of supplemental programs on patient adherence to one or more prescribed substances.

According to one embodiment of the present invention, a method of determining the effectiveness of a plurality of available supplemental programs on patient adherence comprises four steps: (1) defining a plurality of cohorts, each cohort comprising at least one health care provider; (2) receiving data relating to an electronic prescription of the one or more prescribed substances generated by a health care provider and activating the supplemental programs associated with the cohort to which the health care provider belongs; (3) receiving patient adherence data relating to electronic prescriptions for the one or more prescribed substances issued by the plurality of health care providers; and (4) analyzing the patient adherence data to determine the effectiveness of the different permutations of the supplemental programs on patient adherence.

Although the processes and functions described below are described and exemplified as being performed by the SP module in general, it should be understood that the invention is not so limited, and in alternate embodiments the processes and function described herein with reference to cohorts may be performed by any single portion, the central portion 301 or the SP widget 302, or a combination of the portions of the SP module.

Referring to FIG. 4, it should be noted that the memory 313 of the server 310 of the SP system 300 further comprises a cohort database 305, a patient adherence generation module 306, and a patient adherence database 307. As explained in more detail below, the cohort database 305 stores, among other things, information relating to a plurality of health care providers 101 who are part of at least one cohort, along with information relating to each of the cohorts defined by the SP module. For instance, after defining the cohorts, the SP module stores information relating to each cohort (e.g., the target drug data, the provider cohort data, the assigned health care providers 101, the assigned permutation of supplemental programs, the cohort rules, the maximum counter, etc.) in the cohort database 305 of the SP system 300.

As also discussed in more detail below, the patient adherence generation module 306 receives data relating to the patient's prescription history for the target drug from the pharmacy system 500 and/or the payor system 600. This information is referred to as patient medication history data. After receiving the patient medication history data, the patient adherence generation module 306 stores the patient medication history data in one or more databases, such as, but not limited to the patient adherence database 307. Thereafter, the patient adherence generation module 306 analyzes the patient medication history data to generate patient adherence data from the received patient medication history data. Finally, the patient adherence generation module 306 stores the patient adherence data in the patient adherence database 307 for further processing. In certain embodiments, the patient adherence generation module 306 obtains all of the drug fill data that it can for a patient for all drugs, not just the drugs for which the patient has prescriptions. Although in the exemplified embodiment the patient adherence generation module 306 does not use the data for drugs without a known prescription, it is contemplated that in certain other embodiments the patient adherence generation module 306 could use the data from both drugs with a known prescription and drugs without a known prescription.

Generally, and as discussed in more detail below, patient medication history data comprises information relating to the medication history of the patient and the patient's fill history for various prescriptions. As also discussed in more detail below, patient adherence data comprises information relating to the patient's adherence to previous prescriptions. Although sometimes described with reference to the target drug of a cohort, it should be noted that the patient medication history data and patient adherence data is not so limited, and in alternate embodiments of the present invention the patient medication history data and/or the patient adherence data may refer to prescriptions for any substances of the patient. Moreover, it should be noted that the patient adherence database 307 may store patient adherence data relating to various different cohorts for the same target drug, along with patient adherence data relating to various different cohorts for different target drugs. One non-limiting example of a patient adherence generation module 306 is the HMACS™ system by DrFirst®.

As discussed in more detail below, the patient adherence generation module 306 receives the patient medication history data either directly or indirectly from another system, such as but not limited to the pharmacy system 500 and the payor system 600. After receiving the patient medication history data, the patient adherence generation module 306 generates the patient adherence data using one or more algorithms that are stored in the patient adherence database 307. Thereafter, the SP module receives the patient adherence data from the patient adherence database 307 so that the SP module may parse and analyze the patient adherence data by cohort to determine the effectiveness of a plurality of different permutations of supplemental programs on patient adherence.

As noted above and as discussed in more detail below, the patient adherence database 307 stores information relating to one or more previously prescribed substances of one or more patients, such as, but not limited to, patient medication history data and patient adherence data. It should be noted that in other embodiments of the present invention, prescription data, patient medication history data, and patient adherence data may be stored on separate databases.

Since, in the exemplified embodiment of FIG. 4, the patient adherence generation module 306 resides within the memory 313 of the SP system 300, it may be said that the SP system 300 receives patient medication history data, parses the patient medication history data, and analyzes the data to generate adherence data for the patient for the target drug. Nonetheless, it should be noted that in other embodiments of the present invention, the patient adherence generation module 306 may reside on another system or within its own system as part of system 1000. Similarly, in other embodiments of the present invention, the adherence database 307 may also reside within the memory of another system of system 1000. For example, according to one embodiment of the present invention and as discussed in more detail below, the patient adherence generation module 306 resides on a separate system as part of the system 1000, and the adherence database 307 resides within the memory of the separate system, such that the patient adherence generation module 306 and adherence database 307 reside on their own separate system (e.g., a patient adherence system).

1. Defining a Plurality of Cohorts

As noted above, the first step of determining the effectiveness of a plurality of supplemental programs on patient adherence comprises the defining (or creating) of a plurality of cohorts, whereby each cohort comprises a plurality of health care providers 101. Generally, the process of defining the plurality of cohorts comprises two steps: (1) assigning a sub-set of a plurality of health care providers 101 to each of the plurality of cohorts; and (2) assigning a different permutation of supplemental programs to each of the plurality of cohorts.

As used herein, the plurality of cohorts is used to test the effectiveness of different permutations of supplemental programs on patient adherence to a particular substance or a plurality of prescribed substances for a particular disease state. Therefore, each cohort out of the plurality of cohorts (of the same program cohort group) all relate to the same prescribed substance(s). For example, a particular prescribed substance, such as Lipitor®, may be assigned to a plurality of cohorts (of the same program cohort group), so that different permutations of supplemental programs may be tested to determine their effectiveness on the patients' adherence to Lipitor®. For further example, a plurality of prescribed substances, such as Lipitor®, Lescol®, Mevacor®, Pravachol®, and Zocor®, for the same disease state, high cholesterol, may be assigned to a plurality of cohorts so that different permutations of supplemental programs may be tested to determine their effectiveness on the patients' adherence to the prescribed substance for that particular disease state (high cholesterol).

It should be noted that when a plurality of cohorts are all related to one another (e.g., are used together as a single test group for the same prescribed substance(s)) they are considered to be part of the same program cohort group. Therefore, according to one embodiment of the present invention, a program cohort group is a group of a plurality of cohorts for the same prescribed substance or plurality of prescribed substances for a particular disease state. However, it should be noted that there may be different program cohort groups that relate to the same prescribed substance. Further, as discussed in more detail below, the related program cohort group for each of the plurality of cohorts is stored within the cohort database 305 of the SP system 300.

As noted above, each cohort of a plurality of cohorts is assigned a sub-set of health care providers 101. Further, as discussed in more detail below, each sub-set of health care providers 101 has a commonality of prescribing factors with relation to the prescribed substance(s) of the program cohort group. It should be noted that although a provider 101 may be associated with only one out of a plurality of cohorts for a particular prescribed substance (or plurality of prescribed substances for a particular disease state), a provider 101 may be a part of other, unrelated program cohort groups. Stated more simply, a provider 101 may only be associated with one cohort of a particular program cohort group, but the provider 101 may be associated with different cohorts of different program cohort groups.

Figure 30:
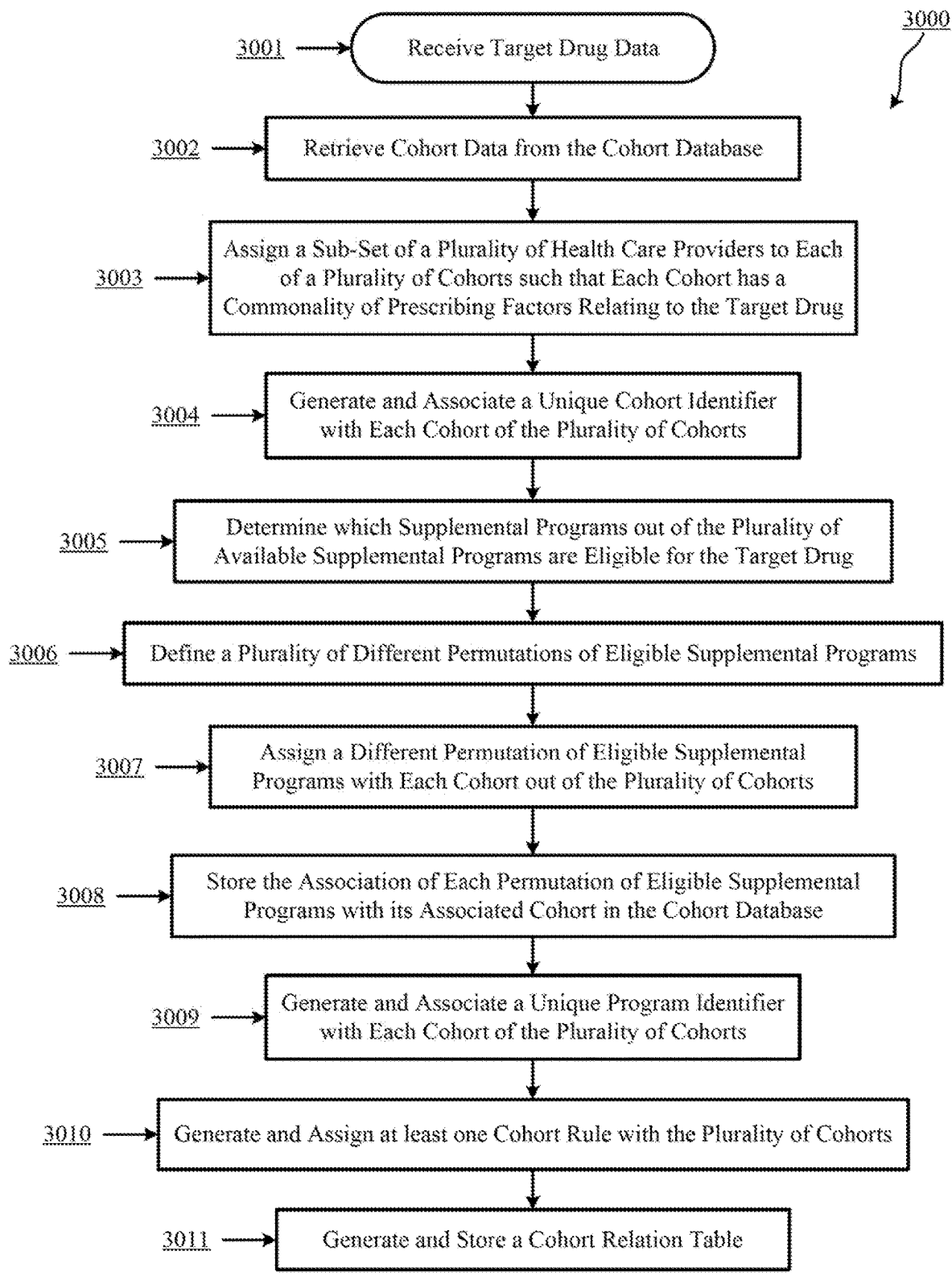
FIG. 30 is a flow chart of a method for defining a plurality of cohorts of a program cohort group according to one embodiment of the present invention.

Referring to FIG. 30, a flow chart of a method 3000 for defining a plurality of cohorts of a program cohort group according to one embodiment of the present invention is illustrated. To begin, the SP module first receives target drug data, thereby completing step 3001. The target drug data comprises information relating to a particular prescribed substance or a plurality of prescribed substances for a particular disease state to which the plurality of cohorts will relate. After receiving the target drug data, the SP module stores the target drug data in the cohort database 305 of the SP system 300 in correlation with a program cohort group.

Therefore, the target drug data defines for which prescribed substance(s) the effectiveness of the available supplemental programs on patient adherence will be analyzed by the SP module. Stated another way, the SP module defines a plurality of cohorts to analyze the effectiveness of the available supplemental programs on patient adherence for only the prescribed substance(s) identified by the target drug data. For example, using the examples set forth above, the target drug data may be just Lipitor® or it may be the combination of Lipitor®, Lescol®, Mevacor®, Pravachol®, and Zocor®. For purposes of simplicity, the term "target drug" will be used to denote the particular prescribed substance or the plurality of prescribed substances for a particular disease state that is defined by the received target drug data. Thus, the term target drug may comprise one or more than one prescribed substance.

According to one embodiment of the present invention, the target drug data is received by the SP module via inputs from the administrator of the SP system 300. It should be noted that an administrator of the SP system 300 may be one or more individuals who have access to and may control the SP system 300 (including the modules residing thereon). In such embodiments, by defining the target drug data, the administrator of the SP system 300 selects the particular prescribed substance(s) that will be used for the cohorts of a program cohort group. It should be noted that the invention is not so limited, and in alternate embodiments the SP module may receive the target drug data from a pharmaceutical company or the target drug data may be derived jointly by both the administrator of the SP system 300 and a third party (e.g., a pharmaceutical company).

Still referring to FIG. 30, after the SP module receives the target drug data, the SP module retrieves provider cohort data from the cohort database 305 of the SP system 300, thereby completing step 3002. As discussed in more detail below, the provider cohort data comprises information relating to each of the plurality of health care providers 101, and more specifically, comprises information relating to the provider's history of prescribing the target drug.

According to one embodiment of the present invention, the provider cohort data comprises a decile level for one or more prescribed substances and/or a medical specialty of the health care provider 101. As understood in the art, a decile level is a rating or level, on a scale from 1 to 10, for which the provider 101 has prescribed a particular prescribed substance or prescribed substances for a particular disease state. For example, a provider 101 who has prescribed Lipitor® more than another provider 101 will have a higher decile level. Therefore, the SP module assigns a sub-set of the plurality of health care providers 101 to each of the plurality of cohorts such that the average decile level of the health care providers 101 assigned to each cohort of a program cohort group is similar. By assigning health care providers 101 to the cohorts based on their decile level, each of the plurality of cohorts of a program cohort group has a commonality of prescribing factors relating to the target drug. However, as discussed below, the invention is not so limited and in alternate embodiments, the SP module assigns health care providers 101 to a cohort based on other factors so long as each cohort of a program cohort group has a commonality of prescribing factors.

As noted above, the use of a decile level is one way to define the cohorts such that there is a commonality of prescribing factors between the health care providers 101 of each cohort of a program cohort group. The present invention may utilize any number of other methods to assign health care providers 101 such that each cohort has a commonality of prescribing factors. Therefore, the commonality of prescribing factors relates to the target drug, ensures that each cohort has a similar cross-section of providers 101 as they relate to the target drug, and may be defined by the SP module in any manner. For example, the SP module may define the commonality of prescribing factors between the plurality of health care provider 101 as a decile level, as a rate of prescription of the prescribed substance(s) defined by the target drug data, or a total number of prescriptions written by each provider 101 for the prescribed substance(s) defined by the target drug data. A commonality of prescribing factors could also be determined by the age groups of the prescriber's patients, or age and demographics of the town in which the prescriber is located.

Still referring to FIG. 30, after retrieving the provider cohort data relating to each of the plurality of health care providers 101, the SP module assigns a sub-set of a plurality of health care providers 101 to each of a plurality of cohorts based on the retrieved provider cohort data, thereby completing step 3003. Stated another way, the SP module assigns at least one health care provider 101, and preferably more than one health care provider 101 to each of the plurality of cohorts of a program cohort group. In one embodiment of the present invention, the SP module assigns the health care providers 101 to the plurality of cohorts using the provider's NPI numbers. After assigning a sub-set of the plurality of providers 101 to each of the cohorts of a program cohort group, the SP module stores the provider's NPI number in the cohort database 305 in association with the cohort identifier, as discussed below in more detail. However, the invention is not so limited and in alternate embodiments the assignment of health care providers 101 to cohorts may be done using name or any other identifying factor of the health care providers 101.

Further, it should be noted that the plurality of health care providers 101 that is broken down in sub-sets and assigned to the cohorts of a program control group may be chosen by the SP module via one or more methods. For example, the plurality of health care providers 101 may be selected using geographic location, commonality of prescribing factors, and/or input by an administrator of the SP module.

Figure 31:
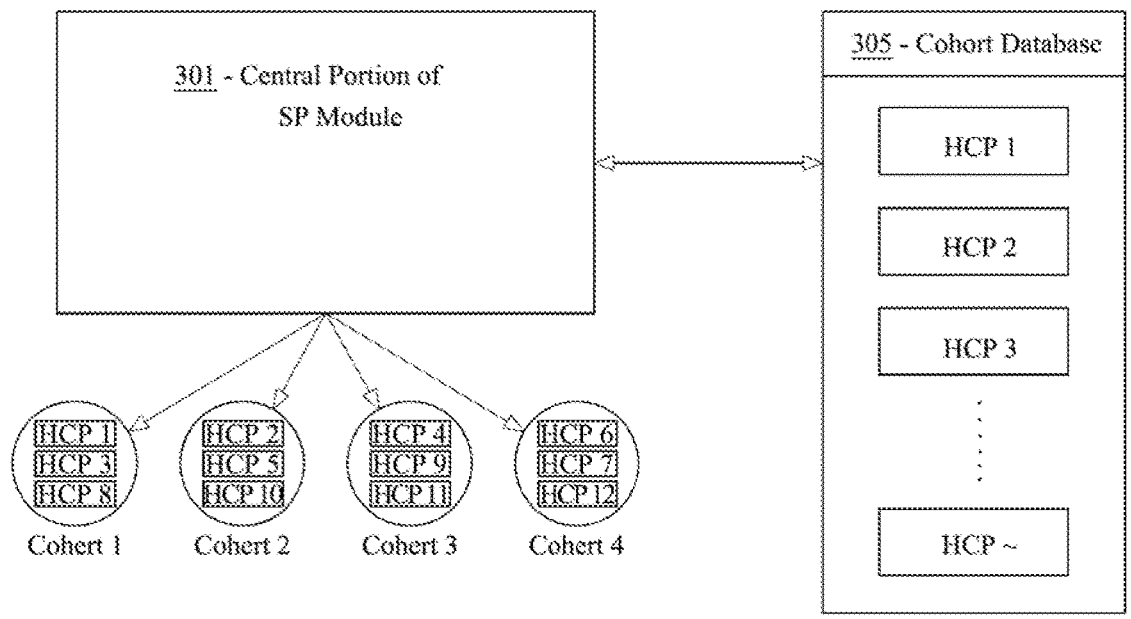
FIG. 31 is a schematic diagram depicting how the SP module defines a plurality of cohorts according to one embodiment of the present invention.

Referring to FIG. 31, a schematic diagram depicting how the SP module defines a plurality of cohorts according to one embodiment of the present invention is illustrated. The SP module retrieving provider 101 information (e.g., provider NPI numbers) from the cohort database 305 or the records database 303. After retrieving the provider 101 information, the SP module defines a plurality of cohorts such that each of the plurality of cohorts comprises a sub-set of the plurality of health care providers 101. It should be noted that in the preferred embodiment, each of the plurality of health care providers 101 is assigned to only one cohort of a program cohort group. For example, as shown in FIG. 31, cohort 1 is defined to comprise health care providers (HCP) 101 number 1, 3 and 8, cohort 2 is defined to comprise HCP 101 number 2, 4, and 10, cohort 3 is defined to comprise HCP 101 number 5, 9, and 11, and cohort 4 is defined to comprise HCP 101 number 6, 7, and 12. Although not exemplified, the health care providers 101 are assigned to each of the cohorts such that each cohort has a commonality of prescribing factors between their assigned providers 101.

Although four cohorts are defined by the SP module in the example exemplified by FIG. 31, the invention is not so limited and in alternate embodiments the SP module may define any number of cohorts for a particular program cohort group. Stated another way, the plurality of cohorts comprises at least two cohorts and may comprise any number of cohorts. Further, although each cohort of FIG. 31 is assigned only three health care providers 101, the invention is not so limited and in alternate embodiments, each cohort may be defined to comprise any number of health care providers 101 so long as each cohort has a commonality of prescribing factors between its assigned health care providers 101. Therefore, according to one embodiment of the present invention, different cohorts of a program cohort group may comprise a different number of health care providers 101.

Referring back to FIG. 30, and as mentioned above, alter assigning a sub-set of health care providers 101 to each of the plurality of cohorts, the SP module generates a cohort identifier for each of the plurality of cohorts. In one embodiment, the cohort identifier is a unique string of numbers used by the SP module to identify that particular cohort. After generating a cohort identifier for each of the plurality of cohorts, the SP module associates the cohort identifier with each of the plurality of health care providers 101 of that particular cohort, thereby completing step 3004. Therefore, each health care provider 101 of a sub-set of health care providers 101 of a particular cohort is associated with the same unique cohort identifier of that cohort. Thereafter, the SP module stores the association of health care provider 101 (e.g. NPI number) and cohort identifier in the cohort database 305 of the SP system 300. As a result, and as discussed in more detail below, the SP module may more easily identify the associated cohort of a particular health care provider 101 using the provider's associated cohort identifier stored in the cohort database 305.

As noted above and in accordance with one embodiment of the present invention, the assignment of providers 101 between cohorts is accomplished by the SP module via inputs from the administrator of the SP system 300. In one embodiment, the instructions from the administrator of the SP system 300 specify which provider 101 is assigned to which cohort. In another embodiment, the instructions from the administrator of the SP system 300 specify rules by which the providers 101 will be assigned to each cohort (e.g., geographic location, specialty, prescribing history of the target drug, etc.). In yet another embodiment of the present invention, the SP module does not receive instructions, but rather automatically assigns providers 101 to each cohort using an algorithm stored within the cohort database 305, such that each cohort has a commonality of prescribing factors.

After assigning a sub-set of a plurality of health care providers 101 to each of the cohorts, the SP module assigns a different permutation of eligible supplemental programs to each cohort. As discussed above, the supplemental program database 303 of the SP system 300 stores general supplemental program data, including, but not limited to the name of the supplemental program, general information relating to the supplemental program, and the rules of each supplemental program. As noted above, each supplemental program comprises rules (non-cohort rules), such as a particular prescribed substance(s) for which the program is eligible and information relating to which patients are eligible for the supplemental program.

Still referring to FIG. 30, prior to assigning a different permutation of eligible supplemental programs to each cohort, the SP module determines which supplemental programs out of the plurality of available supplemental programs are eligible for target drug of the plurality of cohorts, thereby completing step 3005. According to one embodiment of the present invention, eligibility is determined by the SP module based on the target drug defined by the received target drug data. Therefore, the SP module determines which supplemental programs out of the available supplemental programs are eligible for the cohorts based on the received target drug data.

After determining which of the available supplemental programs are eligible for the plurality of cohorts based on the received target drug data, the SP module retrieves information relating to the plurality of eligible supplemental programs from the supplemental program database 303 of the SP system 300. After retrieving information relating to the plurality of eligible supplemental programs, the SP module defines a plurality of different permutations of the eligible supplemental programs, whereby the number of permutations of eligible supplemental programs equals the number of different cohorts of the program cohort group, thereby completing step 3006. Therefore, the SP module creates an equal number of permutations of eligible supplemental programs and cohorts. Finally, after defining a plurality of different permutations of the eligible supplemental programs for the target drug, the SP module assigns a different permutation of supplemental programs with each cohort of the program cohort group, thereby completing step 3007.

According to one embodiment of the present invention, the SP module receives instructions regarding how to define the different permutations of eligible supplemental programs from the administrator of the SP system 300. For example, the administrator of the SP system 300 may transmit instructions to the SP module which dictate the exact configurations of each of the different permutations of eligible supplemental programs. This may be beneficial if the administrator would like to test specifically the effectiveness of particular combinations of supplemental programs on patient adherence. In such embodiments, if the instructions comprise the specific permutations of eligible supplemental programs, then the SP module may not have to determine which supplemental programs are eligible for the target drug, define a plurality of different permutations, and/or assign the different permutations to each of the cohorts.

In the preferred embodiment of the present invention, one of the permutations of supplemental programs is created such that the cohort of which it is associated is a control group. A control group is a cohort which is assigned a permutation of supplemental programs that either does not comprise any supplemental programs or comprises one or more supplemental programs that are also common to all of the plurality of permutations of supplemental programs assigned to the other cohorts of the program cohort group. Stated another way, a permutation of supplemental programs may be used as a control group if: (1) it does not comprise any supplemental programs; or (2) only comprises supplemental programs that are also included in each of the other permutations of supplemental programs of a program cohort group. The use of a control group is beneficial because it provides a baseline for the SP module to analyze the effectiveness of the other supplemental programs on patient adherence. Nonetheless, although it is preferred that one of the plurality of cohorts is a control group, it should be noted that in alternate embodiments of the present invention a control group may be omitted.

Further, according to one embodiment of the present invention, each cohort further comprises a current counter and a maximum counter. The maximum counter defines/stores the maximum number of times the permutation of supplemental programs for a cohort may be activated by the SP module, while the current counter defines/stores the number of times the permutation of supplemental programs for a particular cohort has been activated to date. Therefore, by using both a current count and a maximum counter, the SP module may ensure that the permutation of supplemental programs for each cohort of a program cohort group get activated an equal number of times. As discussed in more detail below, by limiting the total number of times the SP module may activate the permutation of supplemental programs for each cohort, each permutation of supplemental programs will have been activated the same number of times when the SP module determines the effectiveness of each permutation. This helps to provide a more accurate representation of the effectiveness of the supplemental programs on patient adherence. Further, in one embodiment of the present invention, when the current counter of all the cohorts of a program cohort group reach the maximum counter, the SP module ceases to activate the permutations of supplemental programs for the cohorts of the program cohort group, and analyzes patient adherence data to determine the effectiveness of the different permutations of the supplemental programs on patient adherence.

Figure 32:
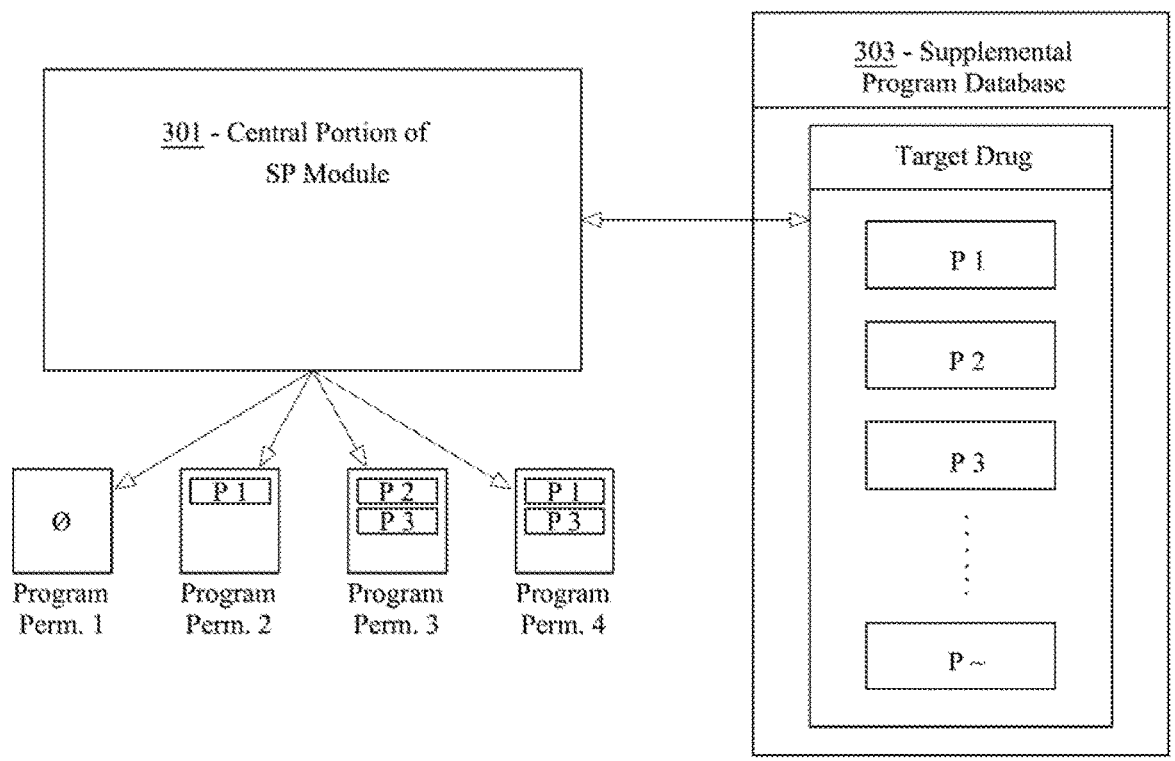
FIG. 32 is a schematic diagram of a method of defining a plurality of different permutations of eligible supplemental programs for a target drug according to one embodiment of the present invention.

Referring to FIG. 32, a schematic diagram of a method of defining a plurality of different permutations of eligible supplemental programs for a target drug according to one embodiment of the present invention is illustrated. As exemplified, the SP module retrieves supplemental program data from the supplemental program database 303, the supplemental program data relating to supplemental programs which are eligible for the target drug. After retrieving the supplemental program data, the SP module defines a plurality of different permutations of eligible supplemental programs. This may be accomplished by the rules engine of the SP module or via instructions received by the SP module from the administrator of the SP system 300, as discussed in detail above.

Referring to FIG. 32, the permutations of supplemental programs are defined by the SP module such that permutation number 1 does not comprise any eligible, supplemental programs, permutation number 2 comprises supplemental program number 1, permutation number 3 comprises supplemental program number 2 and 3, and permutation number 4 comprises supplemental program number 1 and 3. It should be noted that FIG. 32 is but just one example of the SP module defining a plurality of different permutations of supplemental programs. It should be noted that the present invention is not limited to the number of permutations of supplemental programs or the number of supplemental programs per permutation.

Figure 33:
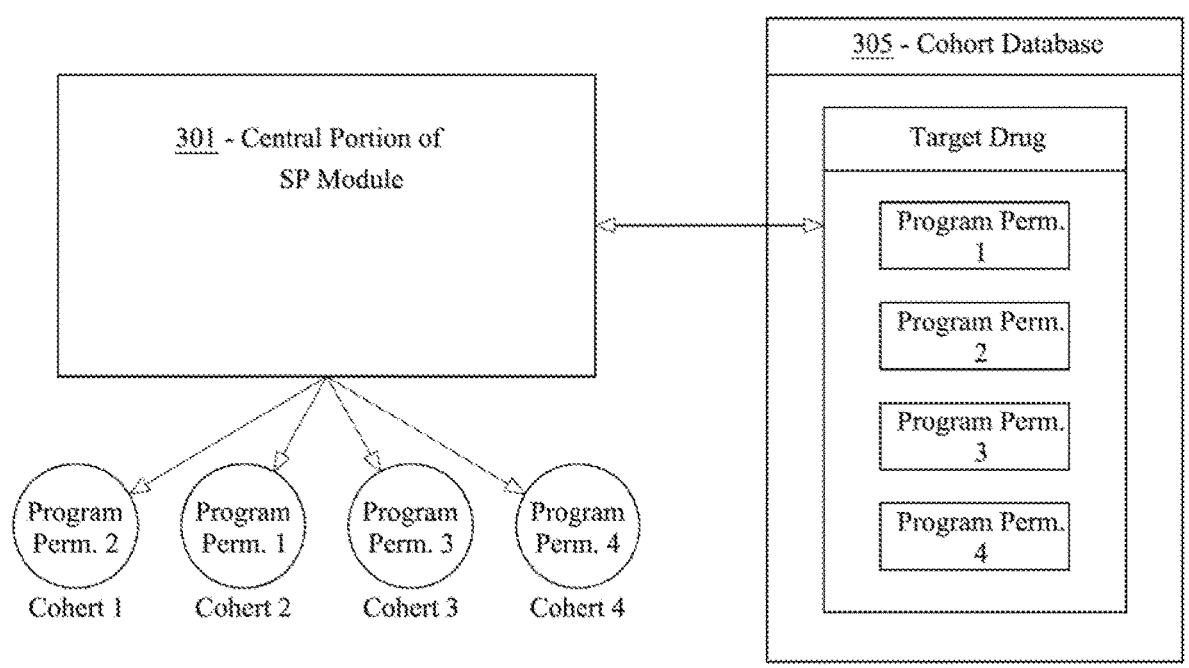
FIG. 33 is a schematic diagram of a method of assigning a different permutation of eligible supplemental programs to each cohort out of a plurality of cohorts of a program cohort group according to one embodiment of the present invention.

Referring to FIG. 33, a schematic diagram of a method of assigning a different permutation of eligible supplemental programs to each cohort out of a plurality of cohorts of a program cohort group according to one embodiment of the present invention is illustrated. After creating the plurality of permutations of the eligible supplemental programs, the SP module assigns a different permutation of eligible supplemental programs to each cohort. According to one embodiment of the present invention, the SP module may receive instructions from the administrator of the SP system 300 that defines how the SP module is to assign the different permutations of eligible supplemental programs to each cohort. However, the invention is not so limited, and in alternate embodiments of the present invention, the SP module may assign the permutation of supplemental programs to each cohort using an algorithm stored within the cohort database 305 that dictates how the permutations are to be assigned to each cohort.

For example and as exemplified in FIG. 33, the central portion 301 the SP module assigns program permutation number 2 to cohort number 1, program permutation number 1 to cohort number 2, program permutation number 3 to cohort number 3, and program permutation number 4 to cohort number 4. It should be noted that this is just one non-limiting example of the assignment of permutations of supplemental programs to cohorts in accordance with the present invention. Specifically, it should be noted that the permutations of the present invention are not limited to any specific number of supplemental programs. Therefore, although only a maximum of two supplemental programs are exemplified in any one permutation, in alternate embodiments of the present invention, a permutation may comprise any number of eligible supplemental programs.

As discussed in more detail below, since permutation number 1 does not comprise any supplemental programs, cohort number 2, which was assigned permutation number 1, is a control group. Stated another way, cohort 2 (and supplemental program permutation number 1) is a control group in which no supplemental programs are available for the target drug. For further example, it should be noted that a control group may comprise at least one supplemental program, as long as the supplemental program(s) of the control group are also assigned to the other cohorts of the program cohort group.

Referring back to FIG. 30, after assigning a different permutation of eligible supplemental programs to each of the cohorts, the SP module stores the association of each permutation of eligible supplemental programs with its associated cohort in the cohort database 305 of the SP system 300, thereby completing step 3008. Therefore, the cohort database 305 comprises a correlated list of the cohorts, the assigned health care providers 101 of each cohort, and the assigned permutation of supplemental programs of each cohort.

According to one embodiment of the present invention, the SP module generates a program identifier for each of the different permutations of supplemental programs. Similar to the cohort identifier discussed above, in one embodiment of the present invention the program identifier is a unique string of numbers used by the SP module to identify that particular permutation of supplemental programs. After generating a program identifier for each of the different permutations of supplemental programs, the SP module associates a program identifier with each of the plurality of health care providers 101 based on their associated cohort, thereby completing step 3009. Thereafter, the SP module stores the association in the cohort database 305 of the SP system 300.

Therefore, according to one embodiment of the present invention, all of the health care providers 101 of a particular cohort are associated with the unique cohort identifier of their associated cohort and the unique program identifier of the associated permutation of supplemental programs of their cohort in the cohort database 305. As a result, and as discussed in more detail below, the SP module may more easily identify the associated cohort and permutation of supplemental programs of a particular health care provider 101 using the cohort identifier and the program identifier stored in the cohort database 305.

Next, the SP module generates at least one cohort rule, and assigns at least one cohort rule to each cohort of the plurality of cohorts, thereby completing step 3010. A cohort rule is similar to a rule, as discussed in detail above, but a cohort rule is a restriction assigned to each of the plurality of cohorts, whereas the rules discussed above are restrictions assigned to at least one supplemental program. Therefore, the cohort rules further restrict a cohort to additional constraints in addition to the target drug and provider 101 restrictions discussed above. Thus, in order for a prescription to qualify for the permutation of supplemental programs of a cohort, the prescription must meet the target drug, provider 101, and cohort rules of a particular cohort. After generating and assigning cohort rules to each of the cohorts of a program cohort group, the SP module stores the cohort rules in association with each cohort in the cohort database 305.

As discussed in more detail below, the rules engine of the SP module applies the cohort rule to the prescription for the target drug to determine whether the prescription qualifies for the cohort, and thus the permutation of supplemental programs of that cohort. Therefore, although a prescription may be for a target drug of a cohort in which the provider 101 belongs, the cohort may still not be eligible for the permutation of supplemental programs of the cohort unless the prescription also meets the cohort rule(s). Thus, in such embodiments, a prescription will only be deemed eligible for a cohort if the rules engine of the SP module determines that the prescribed substance is the target drug of a cohort, the provider 101 is assigned to the cohort, and the prescription meets the cohort rules of the cohort. Nonetheless, it should be noted that the invention is not so limited, and in alternate embodiments of the present invention, each of the plurality of cohorts may not be assigned any cohort rules.

It should further be noted that the cohort rules are exclusionary rules, meaning that if there is an applicable cohort rule for a prescription, then other non-cohort rules (or "rules" as discussed above) are not applied by the rules engine of the SP module when determining whether the prescription qualifies for the cohort, and in turn the permutation of supplemental programs of that cohort. Additionally, in one embodiment of the present invention, the cohort rules comprise the name of the target drug so that the SP module may more easily apply the cohort rules to received prescription data. However, the invention is not so limited, an in alternate embodiments of the present invention, the SP module may apply both the cohort rules and non-conflicting non-cohort rules.

A cohort rule may be similar to any of the non-cohort rules discussed above. For further example, a cohort rule may relate to the dosage strength of the substance (e.g., the prescription of the target drug must be for 60 mg pills or the prescription of the target drug must be equal to or greater than 30 mg pills), the duration in which the patient has been receiving prescriptions for the target drug (e.g., the patient must have been prescribed the drug for at least 90 days prior to the current prescription), the age of the patient (e.g., the prescription must be for a patient who is greater than 18 years old or a patient who is less than or equal to 60 years old), the Medication Persistency Rate (MPR) of the patient, or any other patient adherence data.

Similar to the set-up of the permutations of supplemental programs, according to one embodiment of the present invention, the SP module receives instruction from an administrator of the SP system relating to the generation of the cohort rules of a plurality of cohorts. For example, the administrator of the SP system 300 may transmit instructions to the SP module which dictate the exact cohort rules for the plurality of cohorts. This may be beneficial if the administrator would like to specifically test the effectiveness of supplemental programs on a particular patient type, patients at a particular usage stage of the target drug, or prescriptions for a particular strength of the target drug. However, in an alternate embodiment of the present invention, the rules engine of the SP module generates the cohort rules such that each of the plurality of cohorts are configured to be activated for the most common types of patients receiving prescriptions for the target drug or for patients with a specific MPR range (e.g. patients who have an MPR between 30%-80%).

In accordance with one embodiment of the present invention, the cohort rules may be reconfigured or altered by the SP module at any time. For example, the administrator of the SP system 300 may determine that the results being received from a particular cohort are not ideal. Therefore, the administrator may remove, alter, or reconfigure any cohort rules at any stage after the cohorts are created. By allowing the administrator to alter the cohort rules after the cohorts are in use, the SP module enables the administrator to correct or alter the qualifications required for each cohort. For instance, in one embodiment, the SP module may allow an administrator to use a sliding scale to adjust the range of a particular cohort rule (e.g., a cohort rules restriction qualification of the cohort to prescriptions whose patients have an MPR in a certain range).

Further, in another embodiment of the present invention, the SP module may comprise an algorithm that is configured to automatically adjust a cohort rule based on a percentage of prescription that pass or fail the cohort rule. For example, the SP module may automatically adjust a cohort rules restriction qualification of the cohort to prescriptions whose patients have an MPR between 40-80% to an MPR between 30-90% in order to increase the number of prescriptions qualifying for the cohort.

Further, according to one embodiment of the present invention, one or more cohort rules may be used by the SP module to define the target drug of each cohort, select and allocate providers 101 for each cohort, define the maximum counter of each cohort, and/or select and allocate the permutation of supplemental programs for each cohort. In such instances, the SP module may not receive instructions from the administrator of the SP system 300 that define how to assign providers 101 between cohorts and/or select and allocate the permutation of supplemental programs for each cohort. For example, instead of receiving instructions relating to the specific assignment of providers 101 between cohorts, the SP module may receive instructions defining a cohort rule that automatically allocates specific permutations of supplemental programs to specific providers (e.g., providers living in a certain geographic location are allocated a particular permutation of supplemental programs for a particular prescribed substance(s)). Therefore, in such embodiments, the cohorts will be automatically defined and created by the SP module using cohort rules.

Still referring to FIG. 30 and as discussed above, the SP module stores a correlated list of the information relating to cohorts in the cohort database 305 to aid the SP module in performing additional processing steps. In step 3011, the SP module stores the cohort information in a cohort relation table created by the SP module, the cohort relation table being stored by the SP module in the cohort database 305 of the SP system 300. The cohort relation table associates or links a plurality of data relating to each cohort. For example, the cohort relation table may associate or link any combination of the data relating to each cohort, such as but not limited to, the cohort identifier of a cohort, the provider NPI numbers of a cohort, the target drug of a cohort, the permutation of supplemental programs of a cohort, the current and maximum counter of a cohort and/or the cohort rules of a cohort. Therefore, when the SP module receives prescription data, the rules engine may use the cohort relation table to determine whether a cohort is applicable to the received prescription data, the associated supplemental programs of a cohort, and the current and maximum counter of a cohort.

Referring to FIG. 34, a cohort relation table 3400 according to one embodiment of the present invention is illustrated. As discussed above, according to one embodiment of the present invention, the cohort database 305 stores a cross-referenced listing of cohort identifiers, health care provider NPI numbers, target drug(s), permutation of supplemental programs, current/maximum counter, and cohort rules. Nonetheless, it should be noted that the cohort relation table may comprise a cross-referencing of any number of cohort related data items. Further, it should be noted that the information listed in the cohort relation table 3400 is generically illustrated for purposes of simplicity.

The cohort relation table 3400 may be utilized by the SP module when cross-referencing the cohort database 305, such that the cross-referencing is accomplished using the cohort relation table 3400. This enables the SP module to determine whether a health care provider 101 is associated with a cohort, and if so, what specific cohort, what permutation of supplemental programs associated with the cohort, etc. the SP module should apply for an electronic prescription.

Although exemplified as a single table, it should be noted that in alternate embodiments of the present invention, the cohort relation table may consist of multiple separate tables that are linked to one another (e.g., mapping tables). Therefore, the SP module may determine associated data of one element (e.g., a cohort, a health care provider 101, a target drug, etc.) by searching through the appropriate mapping tables stored within the cohort database 305 of the SP system 300.

Further, in accordance with one embodiment of the present invention, the SP module may change a provider 101 between cohorts using the cohort relation table. Therefore, the SP module may move providers 101 between cohorts, and such changes would update their cohort association stored within the cohort relation table in the cohort database 305.

After storing the cohort relation table in the cohort database 305, the SP module has defined the plurality of cohorts of a program cohort group.

2. Receiving Data Relating to an Electronic Prescription and Activating the Supplemental Programs Associated with the Health Care Provider's Cohort After a plurality of cohorts is defined by the SP module, the SP module is ready to analyze the effectiveness of the different permutations of supplemental programs on patient adherence for the target drug. However, the first step is for the SP module to activate the permutation of supplemental programs of each of the cohorts for electronic prescriptions. As discussed in more detail below, the SP module receives information relating to an electronic prescription for the target drug written by one of the health care providers 101, determines whether the health care provider 101 is part of an existing cohort, and activates that provider's permutation of supplemental programs for the patient upon the provider's request. Thereafter, the SP module receives patient adherence data and analyzes the effectiveness of the activated supplemental programs on the patient's adherence to the target drug. It should be noted, as discussed above, that the target drug may be just one or a plurality of prescribed substances as indicated by the target drug data.

Figure 35A:
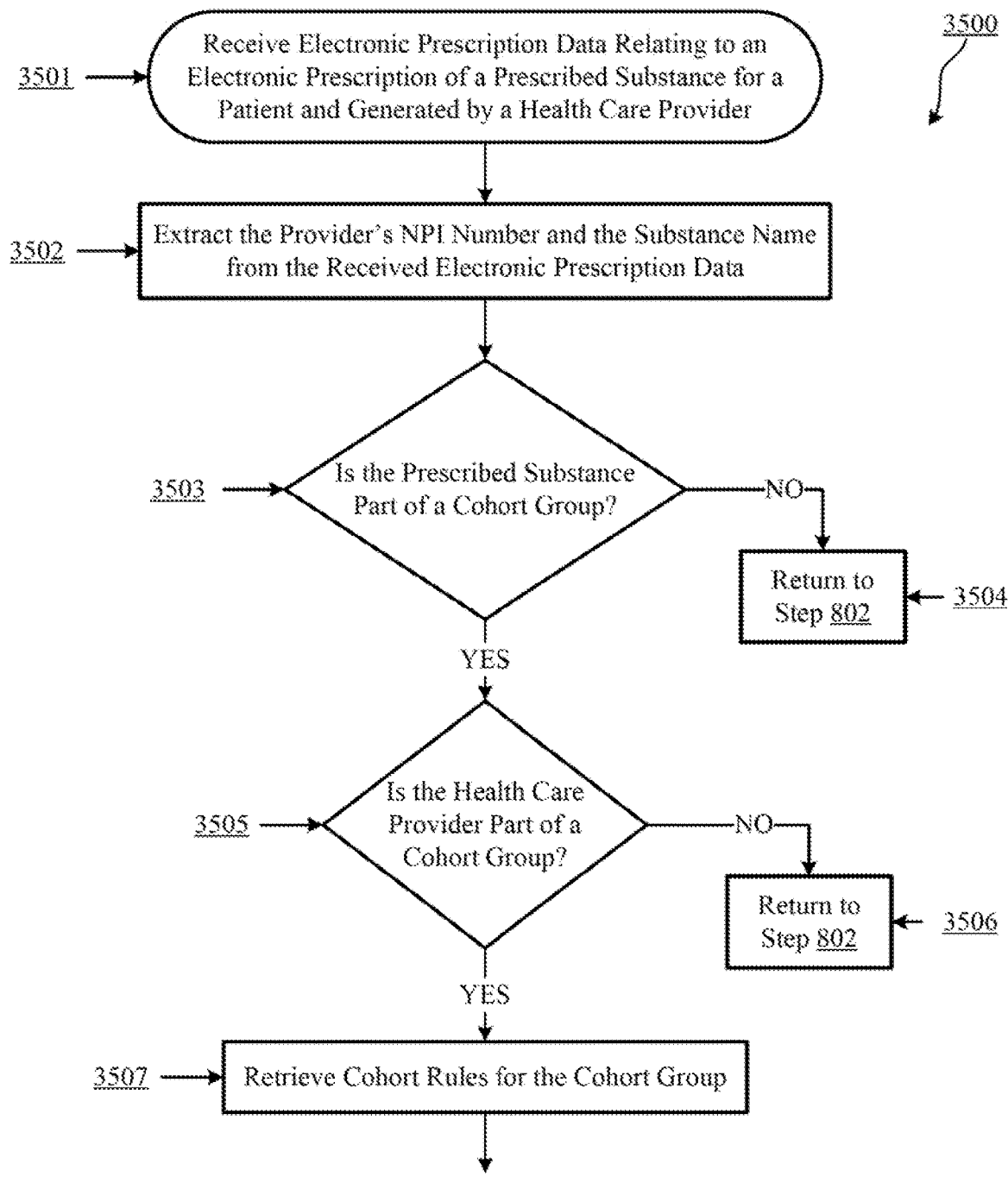
FIGS. 35a-35b are a flow chart of a method for receiving data relating to an electronic prescription for the target drug and activating the permutation of supplemental programs associated with the health care provider's cohort for the target drug according to one embodiment of the present invention.
Figure 35B:
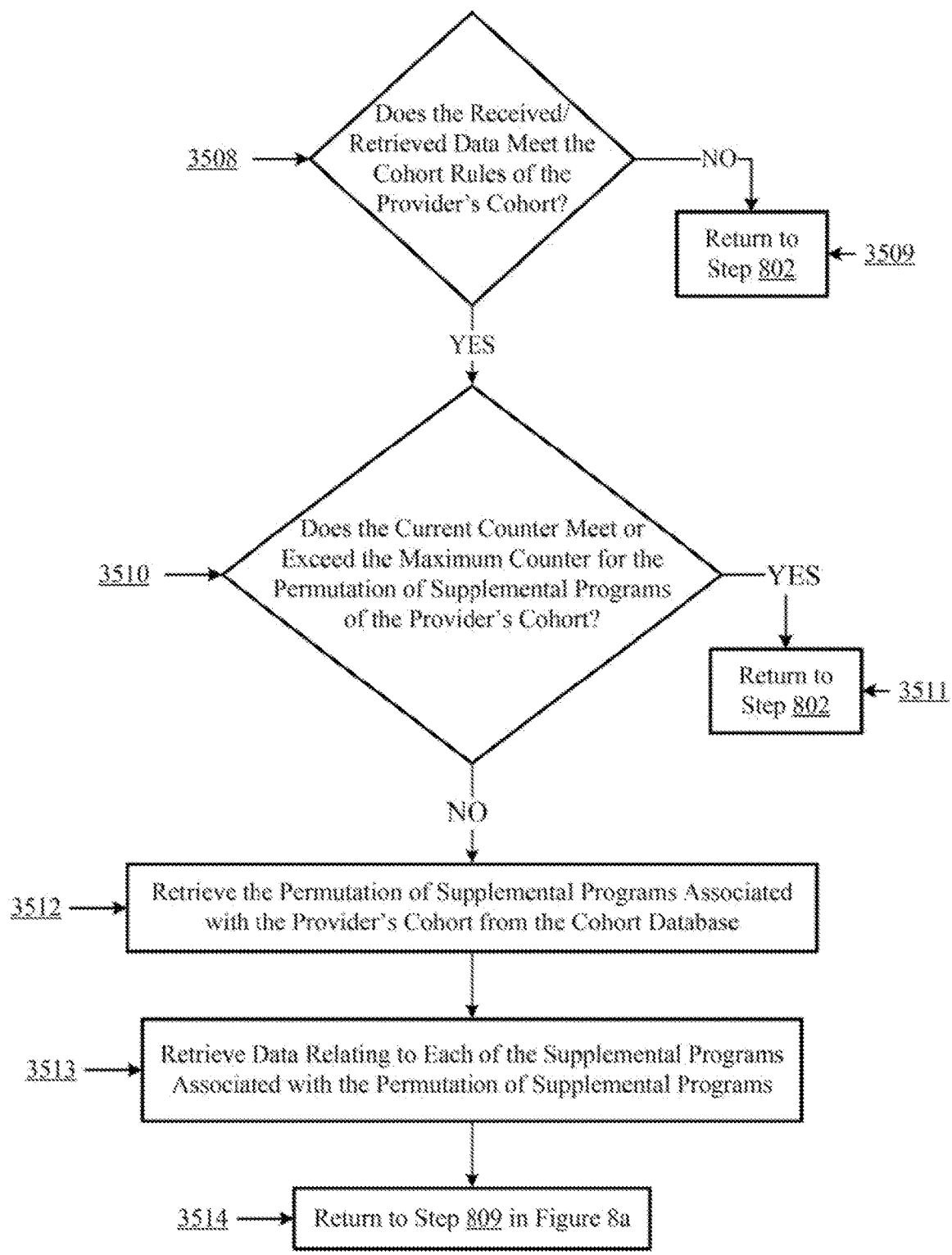

Referring to FIGS. 35a-35b, a flow chart of a method 3500 for receiving data relating to an electronic prescription for the target drug and activating the permutation of supplemental programs associated with the health care provider's cohort for the target drug according to one embodiment of the present invention is illustrated. It should be noted that the method 3500 of FIGS. 35a-35b may be considered an intervening method that works in conjunction with the method 800 exemplified in FIGS. 8a-8c. For example, according to one embodiment of the present invention, the method 3500 picks up after the health care provider 101 writes an electronic prescription for a prescribed substance using the thin client portion 203 of the EP module and the SP widget 302 retrieves data relating to the electronic prescription from the thin-client portion of the EP module 203. Therefore, the method 3500 begins with the central portion 301 of the SP module receiving data relating to the electronic prescription of the prescribed substance for the patient, similar to as discussed above with respect to step 801 of FIG. 8a, thereby completing step 3501.

Further, it should be noted that the method 3500 occurs after the performance of method 3000 by the SP module. Finally, as discussed above with respect to the method 800, the method 3500 is not a one-time transmission of information, but rather a recurrent process that occurs each time a health care provider 101 writes and/or transmits an electronic prescription.

After receiving the electronic prescription data, the SP module extracts the NPI number of the health care provider 101 who wrote the prescription and the prescribed substance of the electronic prescription from the received electronic prescription data, thereby completing step 3502. As noted above, the electronic prescription data comprises first patient data that is specific to the patient, first prescribed substance data that is specific to the prescribed substance, first provider data that is specific to the health care provider 101, and first payor data that is Next, the central portion 301 of the SP module determines whether the prescribed substance of the electronic prescription is part of a particular cohort in decision step 3503. According to one embodiment of the present invention, the central portion 301 of the SP module cross-references the prescribed substance data from the electronic prescription with cohort relation table stored in the cohort database 305 of the SP system 300 to determine if the prescribed substance of the electronic prescription is the target drug of one or more cohorts. For example, according to one embodiment of the present invention, the SP module determines whether the target drug name is associated with any of the defined cohorts.

If the prescribed substance is not associated with any cohorts, then the method moves to step 3504, and as a result, returns to step 802 in FIG. 8*a*. In such instances, the prescribed substance is not associated with any cohorts and, therefore the method returns to step 802 of FIG. 8. Nonetheless, the SP module may still determine eligible supplemental programs for the patient based on the received electronic prescription data, as discussed above in detail with respect to FIGS. 8*a*-8*b*. However, if the prescribed substance is the same as the (or a) target drug of one or more cohorts, then the method continues to step 3505.

Thereafter, the SP module determines whether the health care provider 101 who wrote the prescription is part of one of the cohorts identified in decision step 3505. According to one embodiment of the present invention, the SP module cross-references the provider data from the electronic prescription with the cohort database 305 of the SP system 300 to determine if the provider 101 has an associated cohort, and further if the target drug of the associated cohort is the same as the prescribed substance. For example, in one embodiment of the present invention, the SP module determines whether the provider's NPI number is associated with any of the cohorts for the target drug.

If the health care provider 101 is not associated with any cohorts, then the method moves to step 3506, and as a result, returns to step 802 in FIG. 8*a*. In such instances, even though the prescribed substance is the target drug of one or more cohorts, the provider 101 is not associated with any of the cohorts of that target drug, and therefore the cohort(s) of the target drug are not relevant for determining supplemental programs. Nonetheless, the SP module may still determine eligible supplemental programs for the patient based on the received electronic prescription data, as discussed above in detail with respect to FIGS. 8*a*-8*b*. However, if the health care provider 101 is associated with a cohort of the prescribed substance, then the process continues on to step 3507.

If the method continues to step 3507, then the health care provider 101 is associated with at least one cohort and the prescribed substance is the (or a) target drug of the provider's associated cohort. At that point, the rules engine of the SP module retrieves the cohort rules for that cohort from the cohort relation table stored within the cohort database 305. As noted above, the cohort rules define rules or restrictions that are used by the rules engine to determine whether or not the electronic prescription is eligible for the cohort, and in turn the permutation of supplemental programs of the cohort. It should be noted that in accordance with one embodiment of the present invention, the rules engine of the SP module further retrieves patient data, prescribed substance data, provider data, and/or payor data from the records database 304 of the SP module. This is similar to as discussed with reference to steps 802-805 of FIG. 8*a*.

Referring to FIG. 35*b*, at step 3508 the rules engine of the SP module determines whether the received (and potentially retrieved) data meets the cohort rules of the provider's cohort. If the received/retrieved data does not meet the cohort rules, then the method moves to step 3509 and returns to step 802 of FIG. 8*a*. In such instances, even though the provider 101 is a part of a cohort and the prescribed substance is the target drug of that cohort, the electronic prescription does not meet the other requirements, or cohort rules, of that cohort. Therefore, the electronic prescription is not eligible for the permutation of supplemental programs for that cohort.

However, if the received/retrieved data does meet the cohort rules, then electronic prescription is eligible for the cohort and the method continues to step 3510. At step 3510, the SP module determines whether the current counter of the permutation of supplemental programs meets or exceeds the maximum counter of the permutation of supplemental programs. The SP module makes the determination by checking the cohort relation table stored within the cohort database 305. If the current counter does meet or exceed the maximum counter of the permutation of supplemental programs, then the method continues to step 3511 and returns to step 802 in FIG. 8*a*. In such instances, even though the provider 101 is a part of a cohort, the prescribed substance is the target drug of that cohort, and the electronic prescription meets the cohort rules of that cohort, the permutation of supplemental programs for that cohort has been met or exceeded, so the SP module will not continue to activate that permutation of supplemental programs. However, if the current counter does not meet or exceed the maximum counter of the permutation of supplemental programs, then the method continues to step 3512. Further, it should be noted that in embodiments when the cohort does not comprise a current and maximum counter for the permutation of supplemental programs, steps 3510 and 3511 may be omitted.

At step 3512, the SP module retrieves the permutation of supplemental programs associated with the provider's cohort from the cohort database 305. According to one embodiment of the present invention, the SP module retrieves the cohort identifier of the provider's cohort from the cohort database 305, and in turn, using the cohort identifier, retrieves the program identifier of the cohort from the cohort database 305. The program identifier identifying each of the supplemental programs of the permutation of supplemental programs associated with the provider's cohort.

After retrieving the permutation of supplemental programs from the cohort database 305, the SP module retrieves data relating to each of the supplemental programs associated with the permutation of supplemental programs, thereby completing step 3513. Next, the method continues to step 3514, and as a result, returns to step 809 in FIG. 8*a*. Thereafter, the method may continue as discussed above with reference to FIGS. 8*a*-8*c*. The method may include, but not limited to, any of the embodiments described above.

Therefore, according to one embodiment of the present invention and as discussed in greater detail above, the SP module generates and displays a GUI comprising a list of the supplemental programs associated with the provider's cohort on the display device 121 for the provider's input. Therefore, each of the supplemental programs of the permutation of supplemental programs associated with the cohort to which the health care provider 101 belongs is displayed to the health care provider 101 for selection and activation. Also similar to as discussed above, the SP module will activate each of the supplemental programs associated with the cohort to which the health care provider 101 belongs that are selected and activated by the health care provider 101 using the input device 122 of the HCP system 100. As noted above, activation of a supplemental program may comprise many different steps, including, but not limited to, the delivery or transmission of content to the patient, the transmitting of patient information to sign a patient up for a service, or any other form as discussed above in detail.

However, the invention is not so limited and according to one embodiment of the present invention, and unlike as described above, the provider 101 does not have the opportunity to select or de-select the supplemental programs. Rather, since the provider 101 is associated with the particular cohort, all of the supplemental programs associated with that cohort are automatically activated by the SP module. In such embodiments, a GUI may be, but is not necessarily, displayed to the provider 101 via the display device 121. The supplemental programs are simply activated by the SP module for the patient.

It should be noted that among the processes discussed above that may be incorporated into the embodiments where the prescribing health care provider 101 is a part of a cohort, the use of delivery modes may be incorporated into herein. For example, in one embodiment of the present invention the SP module may retrieve delivery mode data relating to the patient and the supplemental programs of the cohort from the record database 304 and supplemental program database 303 respectively, as discussed in detail above. Thereafter, the SP module may compare delivery mode data relating to the patient with the delivery mode data relating to the supplemental programs to determine common delivery modes, and displaying the common delivery modes of the supplemental programs in the GUI via the display device 121 for selection and acceptance by the health care provider 101, as also discussed above in greater detail. Finally, in such embodiments, if activation of a supplemental program of the cohort causes content to be delivered to the patient, the delivery of the content is via the delivery mode that is selected and accepted by the health care provider 101.

Furthermore, it should be noted that in alternate embodiments of the present invention the SP module widget 302 and not the central portion 301 of the SP module performs the processes relating to the use of the plurality of cohorts. For example, in one embodiment of the present invention, the SP module widget 302 and not the central portion 301 of the SP module determines whether the provider 101 is a part of a particular cohort and/or whether the prescribed substance of the electronic prescription is the (or a) target drug of the provider's associated cohort. In such embodiments, the SP module widget 302 may track electronic prescriptions being prescribed by each one of the plurality of health care providers 101 that are part of one of the plurality of cohorts. Similar to above, the SP module widget 302 may cross-reference electronic prescription data with the cohort database 305. In such embodiments, the cohort database 305 may reside within the memory 113 of the HCP system 100. Thereafter, when a health care provider 101 out of the plurality of health care providers 101 that is a part of one of the plurality of cohorts writes an electronic prescription for the (or a) target drug of that cohort, the SP module widget 302 retrieves electronic prescription data for the target drug from the thin-client portion of the EP module 203 and transmits the electronic prescription data for the target drug to the central portion 301 of the SP module.

Generally, it should be noted that since each cohort is assigned a different permutation of supplemental programs, each cohort may be used to analyze the effectiveness of a specific permutation of supplemental programs on patient adherence. Stated another way, and as discussed in more detail below, each of the plurality of cohorts analyzes the effectiveness of its assigned supplemental programs on patient adherence for the prescribed substance(s) identified by the target drug data.

Figure 36A:
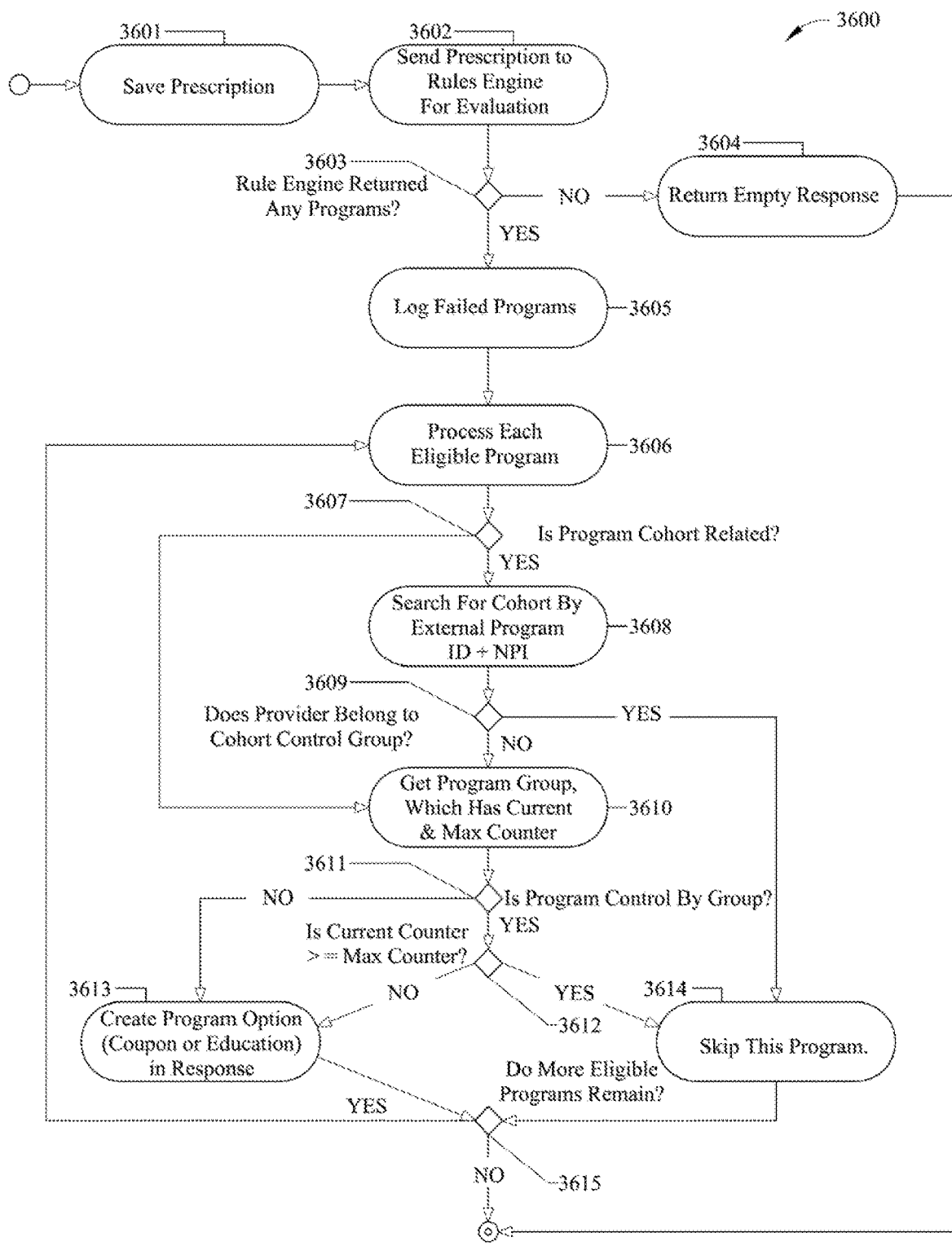
FIG. 36a is a flow chart of a method of retrieving supplemental program data in accordance with an alternate embodiment of the present invention.
Figure 36B:
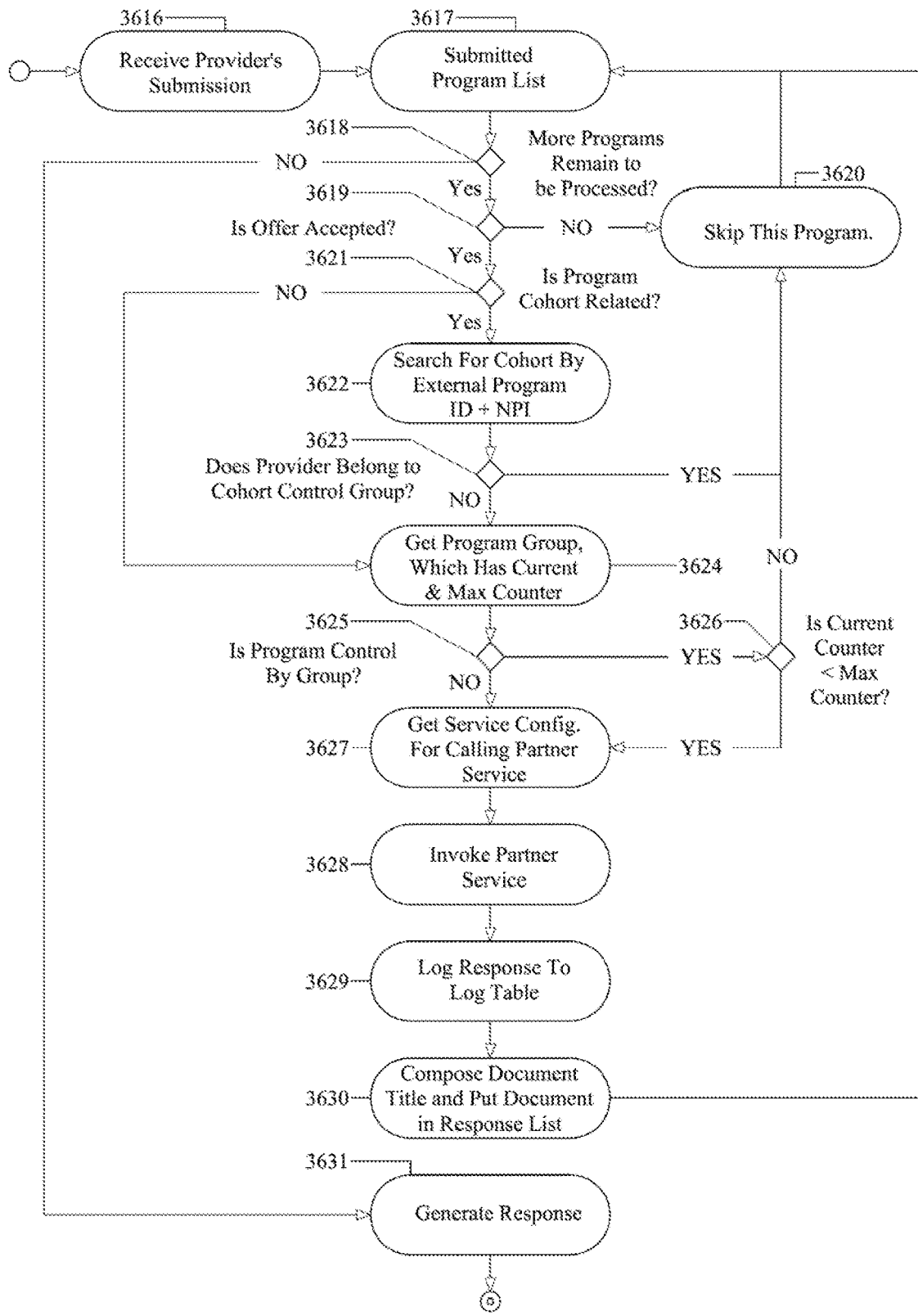
FIG. 36b is a flow chart of a method of generating a document list of all eligible supplemental programs that are selected and accepted by a provider for an electronic prescription according to an alternate embodiment of the present invention.
Figure 36C:
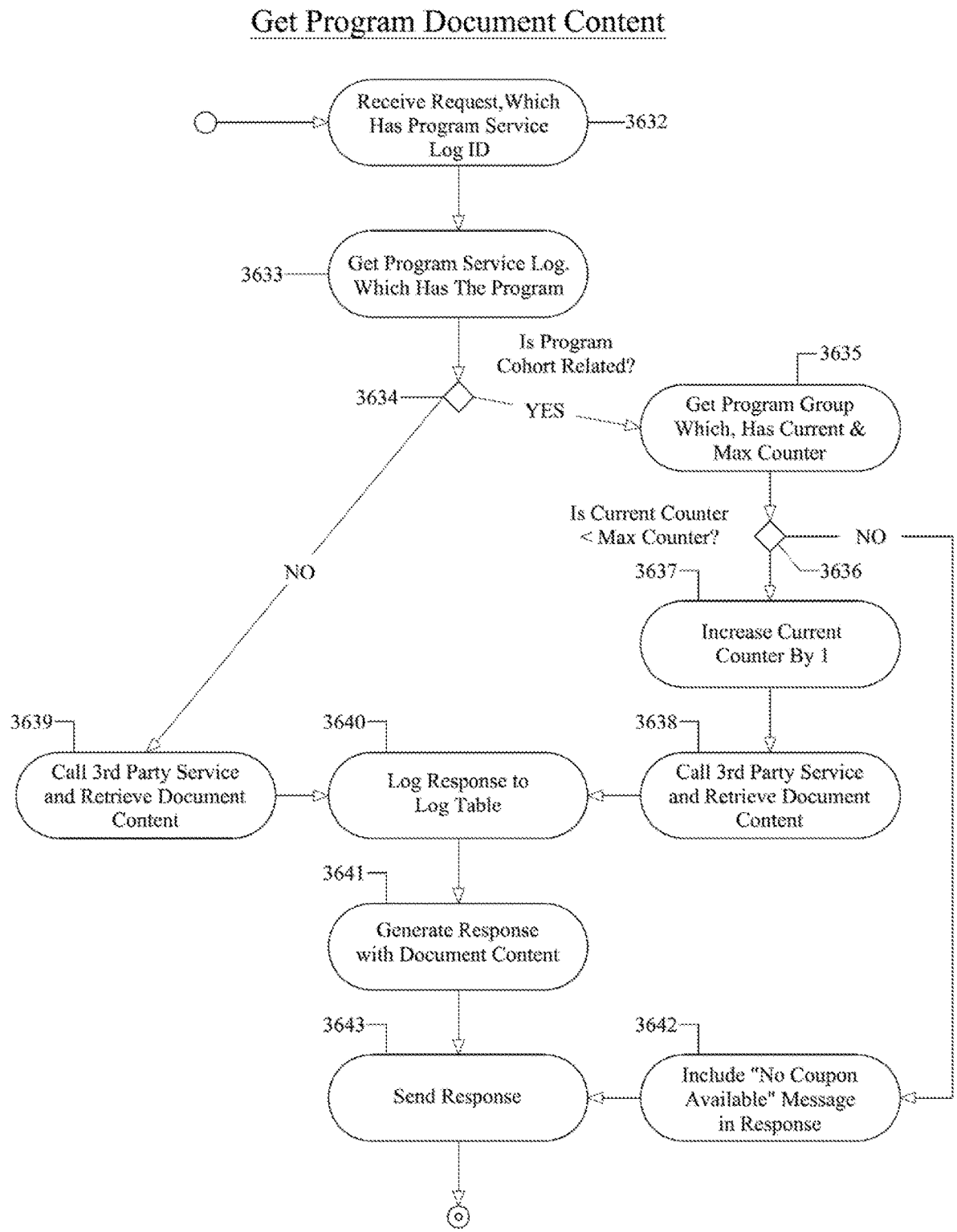
FIG. 36c is a flow chart of a method of retrieving the document associated with supplemental programs that are selected and accepted by a provider for an electronic prescription according to an alternate embodiment of the present invention.

2a. Alternate Embodiment of Processing a Prescription to Determine Eligible Supplemental Programs Via Cohorts Referring to FIG. 36*a*, a flow chart of a method 3600 of retrieving supplemental program data in accordance with an alternate embodiment of the present invention is illustrated. Referring to FIG. 36*b*, a method 3600 of generating a document list of all eligible supplemental programs that are selected and accepted by a provider 101 for an electronic prescription according to one embodiment of the present invention is illustrated. Referring to FIG. 36*c*, a method 3600 of retrieving the document associated with supplemental programs that are selected and accepted by a provider 101 for an electronic prescription according to one embodiment of the present invention is illustrated.

It should be noted that the method 3600 is an alternate method to method 3500 discussed in reference to FIGS. 35*a*-35*b* above. Specifically, as opposed to the method 3500, in which the rules engine first determines whether the electronic prescription is eligible for a supplemental program prior to determining if there are any eligible supplemental programs, in the method 3600 the rules engine first determines if there are any supplemental programs for which the electronic prescription is eligible, and then subsequently determines whether any of the eligible supplemental programs are part of a predefined cohort of the provider 101. It should be further noted that in alternate embodiments of the present invention, the SP module may perform a combination of any of the steps of methods 3500 and 3600 when determining eligible supplemental programs for cohort related electronic prescriptions.

Further, it should be noted that steps 3601-3631 are performed by the rules engine of the SP module, while steps 3632-3634 are performed by the central portion 301 of the SP module. Therefore, although the process of steps 3601-3631 is discussed with reference to the "SP module," it should be noted that the steps 3601-3631 are performed by the rules engine of the SP module. Nonetheless, the invention is not so limited and according to other embodiments of the present invention, the central portion 301 of the SP module and/or the rules engine may perform any of the steps 3601-3634 discussed below.

The method begins at step 3601 with the SP module storing received electronic prescription data in the memory 313 of the SP system 300. According to one embodiment of the present invention, the electronic prescription data may be stored in the record database 304. However, it should be noted that in other embodiments of the present invention, the electronic prescription data may be stored in its own database or in temporary memory within the SP system 300.

After storing the electronic prescription data, the SP module transmits the electronic prescription data to the rules engine for evaluation, thereby completing step 3602. Next, the rules engine evaluates the electronic prescription data to determine if there are any eligible supplemental programs out of the plurality available supplemental programs for the electronic prescription, thereby completing step 3603. If there are no eligible supplemental programs for the prescription, then an empty response is returned in step 3604, and the method ends. However, if there is at least one eligible supplemental program returned, then the method continues to step 3605.

At step 3605, the SP module stores, in a failed programs log in the record database 304, a listing of all of the supplemental programs of the target drug for which the electronic prescription was not eligible. For example, if the prescribed substance met the rules for the supplemental program, but the provider 101 or dosage of the substance did not meet the rules of the supplemental program, then that information is stored within the failed programs log. By storing all of the ineligible supplemental programs for each received prescription, the failed programs log provides a means by which the administrator of the SP system 300 may analyze why certain supplemental programs are being activated more or less than others. This is beneficial in determining how to increase or decrease the activation of certain supplemental programs.

Thereafter, the SP module processes each eligible supplemental program, preferably one at a time, in step 3606. First, at decision step 3607, the rule engine of the SP module determines whether the supplemental program is cohort related. According to one embodiment, the SP module cross references the program identifier of the supplemental program with the cohort relation table (or mapping tables) stored within the cohort database 305. This is beneficial if some of the supplemental programs returned by the rule engine in step 3603 are cohort related while others are not.

If the returned supplemental program is not cohort related (i.e., the provider 101 and/or the substance is not part of the same cohort, or the cohort rules are not met), then the method 3600 continues to step 3610. However, if the supplemental program is cohort related, then the method continues to step 3608. At step 3608, the rules engine of the SP module searches for the provider's cohort using the supplemental program identifier and the NPI number of the provider 101. Specifically, the rules engine cross-references the cohort relation table (or mapping tables) stored within the cohort database 305 to determine the specific cohort in which the supplemental program and electronic prescription belong.

Upon determining the provider's cohort for the substance of the electronic prescription, the rules engine of the SP module determines whether the provider's cohort is a control cohort (or control group), thereby completing decision step 3609. As discussed above, a control group is a cohort which is assigned a permutation of supplemental programs that either does not comprise any supplemental programs or comprises one or more supplemental programs that are also common to all of the plurality of permutations of supplemental programs of the other related plurality of cohorts. If the provider's cohort is a control group, then the method continues to step 3614, and a program option for the eligible supplemental program is not generated for display to the provider 101. However, if the provider's cohort is not the control group, then the method continues to step 3610.

Nonetheless, it should be noted that in some embodiments of the present invention, the method may continue to step 3610 although the provider's cohort is the control group. Specifically, this may be the case if the provider's control group is assigned a plurality of supplemental programs that are common to all of the plurality of permutations of supplemental programs assigned to each of the other cohorts of the program cohort group. In such instances, it is important that the supplemental programs assigned to the control group are also activated. Therefore, in such instance, the method may continue to step 3610.

At step 3610, the rules engine of the SP module retrieves the program cohort group of the provider's cohort, which may comprise a current counter and a max counter of the cohort, from the cohort database 305 of the SP system 300.

After retrieving the program cohort group (and the current and max counter of the supplemental program for the provider's cohort), the SP module determines whether activation of the supplemental program is controlled by the provider's cohort in decision step 3611. It should be noted that one method of controlling the activation of a supplemental program is through the use of a current and max counter. If the activation of the supplemental program is not controlled by a current and max counter (e.g., the supplemental program is not related to a cohort, or the provider's cohort does not comprise a corresponding max counter for the supplemental program), then the method continues to step 3613. However, if the activation of the supplemental program is controlled by the current and max counter, then the method continues to step 3612.

At decision step 3612, the SP module determines whether the current counter of the supplemental program for the provider's cohort is greater than or equal to the maximum counter of the supplemental program for the provider's cohort. If the current counter is greater than or equal to the maximum counter, then the supplemental program has been activated its allotted amount of times for the particular cohort, and as such, the method continues to step 3614. At step 3614, the SP module skips the supplemental program such that the eligible supplemental program is not activated. However, if the current counter is less than the maximum counter, then the supplemental program has not been activated its allotted amount of times for the particular cohort, and as such, the method continues to step 3613.

At step 3613, the SP module generates a supplemental program option for the supplemental program in a response. As discussed below with reference to FIG. 36b, the response will be transmitted by the central portion 301 of the SP module to the SP widget 302 residing on the HCP system 100 so that the SP module may receive the provider's selection and activation of the eligible supplemental programs. According to one embodiment of the present invention, a response is a pop-up window 1010, such as that exemplified in FIG. 15, and the supplemental program option is the information relating to the eligible supplemental program option 1012 display in the pop-up window 1010 on the display device 121 to the provider 101 for the provider's selection and acceptance of each eligible supplemental program. It should be noted that the pop-up window 1010 and the information relating to the eligible supplemental program 1012 is but just one non-limiting example of a response for the supplemental program in accordance with the present invention.

It should be noted that the response may comprise information relating to supplemental programs that are part of the provider's cohort, along with information relating to supplemental programs that are not part of the provider's cohort. However, in one embodiment of the present invention, the SP module removes from the response the information relating to all non-cohort relating supplemental programs so that only those supplemental programs that are part of the provider's cohort are displayed to the provider 101.

After generating the supplemental program option in the response, the SP module continues to decision step 3615. At decision step 3615, the SP module determines whether the any more eligible supplemental programs remaining to be processed at step 3606. In one embodiment, this determination is made by the SP module through a cross-referencing of the supplemental programs determined to be eligible by the rules engine in step 3603. If there remains additional eligible supplemental programs that need to be processed through steps 3606-3615, then the method returns to step 3606 and another eligible supplemental program is processed. After all of the supplemental programs determined by the rules engine in step 3603 to be eligible have been processed through step 3606-3615, the method of FIG. 36a is complete.

Referring to FIG. 36b, a method 3600 of generating a document list of all eligible supplemental programs that are selected and accepted by a provider 101 for an electronic prescription according to one embodiment of the present invention is illustrated. It should be noted that the method of FIG. 36b is a continuation of the method of FIG. 36a. Therefore, as illustrated, the method 3600 of FIG. 36b begins with step 3616. It should be noted that between step 3615 and step 3616, the central portion 301 of the SP module has transmitted the response comprising the information relating to the eligible supplemental programs to the SP widget 302, the SP widget 302 has displayed a list of the eligible supplemental programs on the display device 121 to the provider 101, the provider 101 has selected and accepted the eligible supplemental programs they would like to activate for the patient, and the SP widget 302 has generated a signal indicating the supplemental programs that were both selected and accepted by the provider 101.

At step 3616, the SP module receives a signal from the SP widget 320 indicating which of the supplemental programs are both selected and accepted by the provider 101. In one embodiment, the signal may be the activation signal as discussed above with reference to FIGS. 8a-8c. Next, at step 3617, the SP module retrieves the list of eligible supplemental programs that were displayed for the provider's selection and acceptance. The submitted program list comprising the information relating to each of the eligible supplemental programs, regardless of whether the supplemental programs were selected and accepted by the provider 101 for activation.

Thereafter, at decision step 3618, the SP module determines whether there are any supplemental programs that remain to be processed by the SP module. If so, then the SP module selects one supplemental program from the supplemental program list and determines whether the signal received from the SP widget 302 indicates that the supplemental program was selected and accepted by the provider 101. If the supplemental program was not selected and accepted by the provider 101, then the method continues to step 3620 and the supplemental program does not get activated. However, if the supplemental program was selected and accepted by the provider 101, then the method continues to step 3621.

It should be noted that the process of steps 3621-3623 is very similar to the process of steps 3607-3609 discussed above with respect to FIG. 36a. At decision step 3621, the SP module determines whether the supplemental program is cohort related. As noted above, in one embodiment, the SP module cross references the program identifier of the supplemental program with the cohort relation table (or mapping tables) stored within the cohort database 305. Further, it should be noted that in one embodiment of the present invention, steps 3621-3623 are omitted. In such embodiments, the method goes from step 3620 directly to step 3624.

If the supplemental program is not cohort related, then the method continues to step 3624. However, if the supplemental program is cohort related, then the method continues to step 3622. At step 3622, the rules engine of the SP module searches for the provider's cohort using the supplemental program identifier and the NPI number of the provider 101. Specifically, the rules engine cross-references the cohort relation table (or mapping tables) stored within the cohort database 305 to determine the specific cohort in which the supplemental program and electronic prescription belong.

Upon determining the provider's cohort, the rules engine of the SP module determines whether the provider's cohort is a control cohort (or control group), thereby completing decision step 3623. If the provider's cohort is a control group, then the method continues to step 3620, and the eligible supplemental program is not activated. However, if the provider's cohort is not the control group, then the method continues to step 3624.

Nonetheless, similar to as discussed above, in some embodiments of the present invention, the method may continue to step 3624 although the provider's cohort is the control group. Specifically, this may be the case if the provider's control group is assigned a plurality of supplemental programs that are common to all of the plurality of permutations of supplemental programs assigned to each of the other cohorts of the program cohort group. In such instances, it is important that the supplemental programs assigned to the control group are also activated. Therefore, in such instance, the method may continue to step 3624.

At step 3624, the rules engine of the SP module retrieves the program cohort group of the provider's cohort, which may comprises a current counter and a max counter of the cohort, from the cohort database 305 of the SP system 300. After retrieving the program cohort group (and the current and max counter of the supplemental program for the provider's cohort), the SP module determines whether activation of the supplemental program is controlled by the provider's cohort in decision step 3625. If the activation of the supplemental program is not controlled by a current and max counter, then the method continues to step 3627. However, if the activation of the supplemental program is controlled by the current and max counter, then the method continues to step 3626.

At decision step 3626, the SP module determines whether the current counter of the supplemental program for the provider's cohort is greater than or equal to the maximum counter of the supplemental program for the provider's cohort. If the current counter is greater than or equal to the maximum counter, then the supplemental program has been activated its allotted amount of times for the particular cohort, and as such, the method continues to step 3620. At step 3620, the SP module skips the supplemental program such that the eligible supplemental program is not activated. However, if the current counter is less than the maximum counter, then the supplemental program has not been activated its allotted amount of times for the particular cohort, and as such, the method continues to step 3627.

At step 3627, the SP module retrieves the service configuration from the supplemental program database 303 for calling a third party program vendor 400. The service configuration comprises information relating to the specific third party program vendor 400 that comprises the supplemental program. As noted above, in accordance with one embodiment of the present invention, the SP module does not store the physical documents or run the services that are the supplemental programs. Rather, the SP module simply stores information relating to the supplemental programs so that upon activation, the SP module may retrieve the actual document from the appropriate third party program vendor 400 or enroll the patient in the service by transmitting patient data to the appropriate third party program vendor 400. Nonetheless, in one embodiment of the present invention, the SP module does store the actual documents and run the actual services that are the supplemental programs. In such embodiments, steps 3627-3629 may be omitted.

Next, at step 3628, the SP module transmits a signal to the appropriate third party program vendor 400 to invoke the vendor 400 to confirm that the third part program vendor 400 does in fact have stored the actual document or service relating to the supplemental program. Thereafter, the SP module receives the confirmation signal from the appropriate third party program vendor 400, and logs the confirmation from the third party program vendor 400 in a log table at step 3629, the log table being stored within the cohort database 305.

Next, at step 3630, the SP module generates the supplemental program title and puts the supplemental program title in a response list, the response list stored in the cohort database 305. As discussed in more detail below, the response list comprises the titles of the supplemental programs that were selected and accepted by the provider 101. After putting the document title in the response list, the method returns to steps 3617 and 3618 and the SP module determines if there are any remaining supplemental programs that need to be processed. Upon the SP module processing each of the selected and accepted supplemental programs, the method continues to step 3631 and the SP module generates a response, the response comprising the response list that comprises the titles of the supplemental programs that were selected and accepted by the provider 101.

Referring to FIG. 36c, a method 3600 of retrieving the document associated with supplemental programs that are selected and accepted by a provider 101 for an electronic prescription according to one embodiment of the present invention is illustrated. It should be noted that the method of FIG. 36c is a continuation of the method of FIG. 36b.

At step 3632, the central portion 301 of the SP module receives a request from the rules engine which comprises the response listing a log identifier for the supplemental programs that were selected and accepted by the provider 101 for activation. The log identifier has the program identifiers for the supplemental programs that were selected and accepted by the health care provider 101.

Next, in step 3633, the central portion 301 of the SP module retrieves the supplemental program service log from one or more of the databases of the SP system 300. The supplemental program service log indicates the supplemental programs that were selected and accepted by the provider 101 for activation.

Next, at decision step 3634, the central portion 301 of the SP module determines whether the supplemental program is related to the provider's cohort. If the supplemental program is cohort related, then the method continues to step 3635 and the central portion 301 of the SP module retrieves the program group of the supplemental program, which comprises the current and maximum counter. However, if the supplemental program is not cohort related, then the method continues to step 3639, as discussed in more detail below.

Assuming the supplemental program is cohort related and after retrieving the current and maximum counter of the supplemental program for the provider's cohort, the central portion 301 of the SP module determines whether the current counter is less than the maximum counter at decision step 3636. If the current counter is not less than the maximum counter, then the central portion 301 of the SP module generates a message indicating that the supplemental program is not available for activation (e.g., "No Coupon Available"), and includes that message in a response that is transmitted to the SP widget 302 for display to the provider 101 on the display device 121. However, if the current count is less than the maximum counter, then the central portion 301 of the SP module increases the current counter by one, such increase being stored in the cohort database 305, thereby completing step 3637.

Next, the central portion 301 of the SP module calls the appropriate third party program vendor 400 and retrieves the actual document or information relating to the service of the supplemental program. In one embodiment, the central portion 301 of the SP module transmits the program identifier to the third party program vendor 400 and receives the actual document or information relating to the service of the supplemental program from the third party program vendor 400. However, the invention is not so limited, and in alternate embodiments the central portion 301 of the SP module may transmits any signal indicating the specific supplemental program to the appropriate third party program vendor 400.

Referring back to step 3634, if the supplemental program is not cohort related, then the central portion 301 of the SP module calls the appropriate third party program vendor 400 and retrieves the actual document or information relating to the service of the supplemental program, thereby completing step 3639. This is similar to the process described with respect to step 3638.

Thereafter, the SP module receives the actual document or information relating to the service of the supplemental program from the appropriate third party program vendor 400, and stores the actual document or information relating to the service of the supplemental program in the supplemental program database 303 (or other temporary memory). Thus, the SP module has, within one or more of its databases, the actual document or information relating to the service of the supplemental program. Thereafter, the SP module logs the response from the third party program vendor 400 in a log table at step 3640, the log table being stored within the cohort database 305.

Next, the central portion 301 of the SP module generates a response that comprises the actual document or information relating to the service of the supplemental program. It should be noted that the response may comprise more than one document or other supplemental program related information. Thereafter, the central portion 301 of the SP module transmits the response, along with the associated documents and information, to the SP widget 302, thereby completing step 3643.

Upon receiving the response, the SP widget 302 may display a GUI to the provider 101 that allows the provider 101 to distribute the document or other supplemental program information to the patient. In an alternate embodiment of the present invention, the SP widget 302 may transmit the documents directly to a printer without requiring provider interaction. Nonetheless, it should be noted that, upon receiving the response, the SP widget 302 may cause the documents and other information to be disseminated in any manner consistent with the present invention.

3. Receiving Patient Adherence Data

After the SP module activates the supplemental programs of the cohort that were selected and accepted by the provider 101, the patient receives the activated supplemental programs. Thereafter, as discussed in detail below, the SP module receives patient adherence data relating to the electronic prescription. It should be noted that since there are a plurality of different cohorts and since each cohort comprises a sub-set of health care providers 101, the SP module will receive patient adherence data relating to a plurality of difference electronic prescriptions generated by different health care providers 101, some of these prescriptions for a target drug of a cohort and other not. Further, the SP module will be reaching patient adherence data while the program cohort groups are still active. Thereafter, upon receiving patient adherence data, the SP module must parse the patient adherence data by the cohort in which the patient adherence data relates.

As noted above, according to one embodiment of the present invention, the memory 313 of the SP system 300 further comprises a patient adherence generation module 306. The SP system 300, and more particularly the patient adherence generation module 306, receives patient medication history data relating to a plurality of electronic prescriptions for which supplemental programs were previously activated. It should be noted that the received patient medication history may, but does not have to relate to prescriptions that met all of the cohort rules and caused the activation of the permutation of supplemental programs for a cohort. Stated another way, the patient adherence generation module 306 receives patient medication history data relating to a plurality of electronic prescriptions, regardless of whether supplemental programs of a cohort (as opposed to supplemental programs in general) were activated for the prescription. As discussed in more detail below, the patient adherence generation module 306 receives the patient medication history data from another system, such as but not limited to the pharmacy system 500 and the payor system 600.

Generally, the patient medication history data comprises information relating to the medication history of the patient for one or more prescribed substances. This may, but does not necessary include prescriptions for the target drug of a cohort. For example, patient medication history may comprise any of the substance data described above (e.g. substance details such as the dosage, strength, form, duration, quantity, date, and refills) with reference to a prescription, the prescription start date and stop date, information relating to whether the patient picked up the prescription, the duration in which the prescription sat at the pharmacy prior to patient pickup, the number of refills of the prescription that the patient filled, and the time frame between refills in comparison to the duration of each prescription. Further, it should be noted that the patient medication history data may comprise information relating to any number of prescriptions for any number of patients, regardless of whether supplemental programs were activated by the SP module for those prescriptions.

However, in one embodiment of the present invention, the patient adherence generation module 306 only receives patient medication history data for prescriptions in which supplemental programs were activated. Further, in other embodiments, the patient adherence generation module 306 only receives patient medication history data for prescriptions of a target drug of a cohort in which the permutation of supplemental program of that cohort were activated.

After receiving the patient medication history data, the patient adherence generation module 306 generates patient adherence data from the received patient medication history data. After generating the patient adherence data, the patient adherence generation module 306 stores the patient adherence data in the patient adherence database 307. According to one embodiment of the present invention, the patient adherence generation module 306 generates the patient adherence data by applying the received patient medication history data to one or more algorithms configured to determine patient adherence metrics from the received patient medication history data. Through use of the algorithms, the patient adherence generation module 306 generates one or more adherence analytics for a particular prescription and/or medication history data of a patient. In such embodiments, the algorithms are stored in the patient adherence database 307 of the SP system 300.

It should be noted that, in accordance with one embodiment of the present invention, a prescription and drug fill (which is a type of patient medication history data—e.g., the date on which a prescription was filled by a patient) must qualify for calculating patient adherence for a given patient and substance in order to be used by the SP module when determining patient adherence data. A prescription qualifies if the prescription matches the target drug by name, has a stop date that is after the compliance interval start date, and is either the most recent matching prescription or has a stop date that is within N days (e.g. 30) of the start date of the next most recent prescription. A drug fill qualifies if it matches the target drug by name, has a fill date that is after the compliance interval start date, and has a fill date that is between the start and stop date of a qualifying prescription. The compliance interval start date is the start of a compliance interval of interest.

Generally, patient adherence data comprises information relating to a patient's adherence, compliance, and/or persistency to prescriptions issued to the patient. As noted above, the prescriptions may, but do not necessarily have to be for the target drug of a cohort. For example, the patient adherence data may comprise information relating to the patient's first fill compliance of a prescription, the patient's first fill interval of a prescription, the patient's compliance interval of a prescription, and any other information relating to the patient's adhere, compliance, or persistency to a prescription.

For further example, in one embodiment of the present invention, patient adherence data comprises first fill compliance (FFC) data and patient Medication Persistency Rate (MPR) data. Generally, FFC data comprises information relating to whether or not the patient has been prescribed a particular prescribed substance (e.g., the target drug) in the past and/or whether the patient picked-up or took the particular prescribed substance (e.g., the target drug) in the past.

Further, in one embodiment of the present invention, FFC data of a prescription has three possible values: (1) present; (2) absent: or (3) unknown. The FFC data has a value of present if there exists a qualifying drug fill where: (1) the fill date of the prescription is after the start date of the prescription; and (2) the fill date of the prescription is before the end of the end of the first fill interval of the prescription. In such instances, the prescription was filled by the patient after the prescription was written by the health care provider 101, but before the end of the first fill interval of the prescription. Therefore, the prescription is first fill compliant.

The FFC data has a value of unknown if the start date of the prescription is after the end of the first fill interval of the prescription. In such instances, the prescription occurred after the first fill interval and therefore may be a refill of the prescription. Thus, information relating to a refill of a prescription does not indicate whether the patient was compliant with filling their prescription on the first fill. In all other instances, the FFC data has a value of absent.

Generally, MPR data comprises information relating to the patient's adherence to a particular prescribed substance (e.g., the target drug). For example, MPR data may comprise information relating to the degree or extent of conformity of the patient to the recommendations about day-to-day treatment by the health care provider 101 with respect to the timing, dosage, and/or frequency of a particular prescribed substance (e.g., the target drug), information relating to the extent to which a patient acts in accordance with the prescribed interval and dose of a dosing regimen of the particular prescribed substance (e.g., the target drug), and information relating to the continuation of the treatment by the patient for the prescribed duration of the particular prescribed substance (e.g., the target drug). Therefore, in one embodiment of the present invention, the MPR data comprises, as a percentage, information relating to how often the patient filled a prescription compared with how often s/he could have filled it optimally. Finally, it should be noted that in some embodiments of the present invention, MPR data may be referred to as medication possession ratio data.

According to one embodiment of the present invention if there are fewer than three qualifying fills of a particular prescription, then the MPR data for that prescription has a value of unknown. Otherwise, if there are three or more qualifying fills of a particular prescription, then the MPR data is calculated as follows. First, the patient adherence generation module 306 of the SP system 300 calculates compliance interval days for the prescription. Compliance interval days is the number of days in a compliance interval, or the number of days that a supply of prescription is available to the patient during the compliance interval. For each qualifying prescription, the patient adherence generation module 306 determines the adjusted prescription start date (the later of the start date of the prescription and the compliance interval start date), the adjusted prescription stop date (the earlier of the prescription stop date or the current date), and the compliance interval clays of the prescription (the adjusted stop date minus the adjusted start date).

Next, the patient adherence generation module 306 calculates the total fill days of the prescription. Total fill days is a measure of the number of days that a supply of a prescription is actually filled by the patient during the compliance interval. For each qualifying prescription, the patient adherence generation module 306 calculates the adjusted fill start date (the later of the fill date of the prescription and the compliance interval start date of the prescription) and the adjusted fill stop date (the earlier of the fill date plus the fill days and the current date). Next, the patient adherence generation module 306 calculates the total fill days of the prescription (the adjusted fill stop date minus the adjust fill start date). Finally, the patient adherence generation module 306 calculates the MPR data for the prescription (the total fill days divided by the compliance interval days—multiplied by 100 to show as percentage).

After the patient adherence data is generated by the patient adherence generation module 306, the patient adherence generation module 306 transmits the patient adherence data to the central portion 301 of the SP module so that the SP module may parse and analyze the patient adherence data by cohort to determine the effectiveness of a plurality of different permutations of supplemental programs on patient adherence.

Figure 37A:
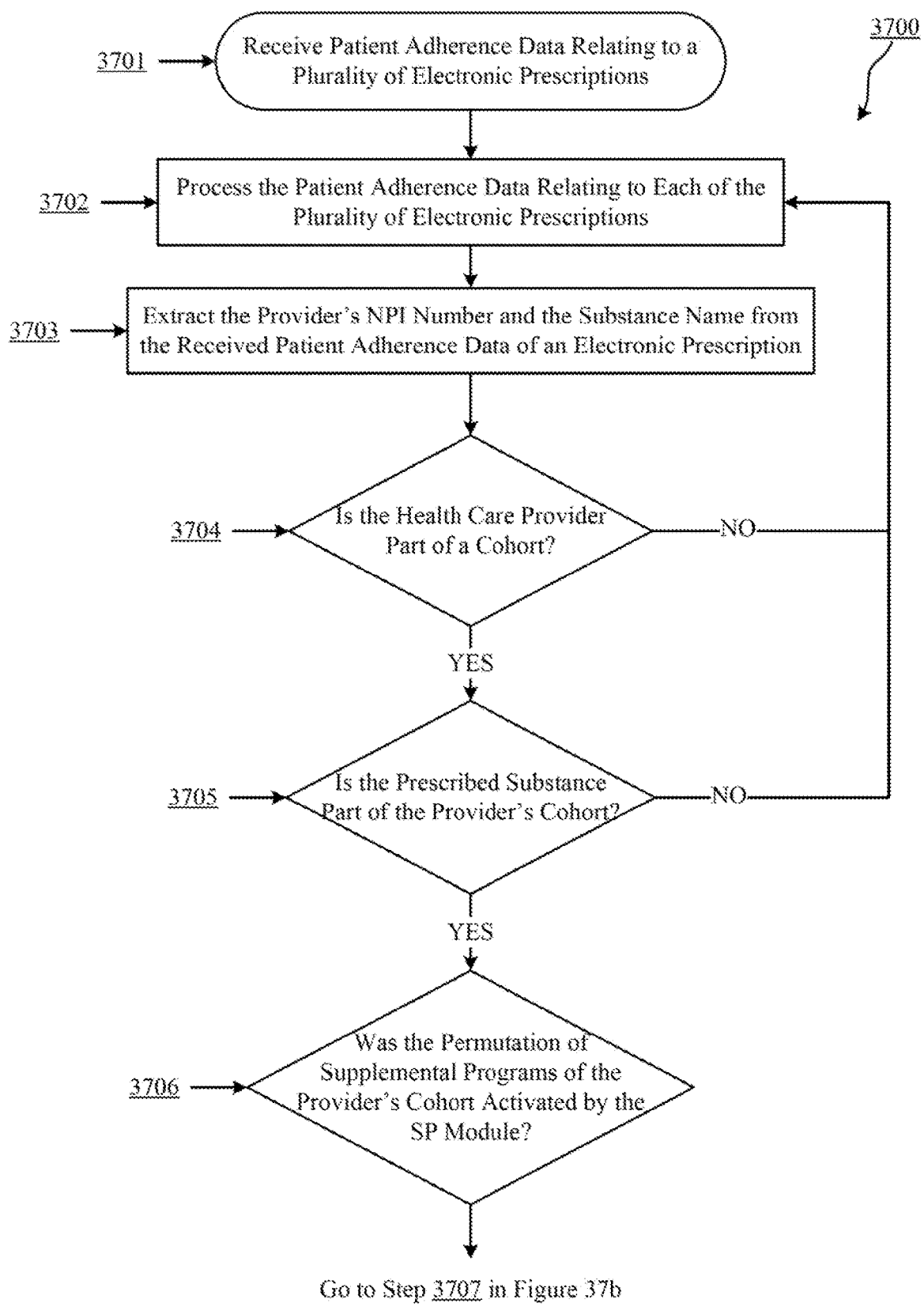
FIGS. 37a-37b are a flow chart of a method of parsing patient adherence data into data grouping based on a plurality of different cohorts according to an embodiment of the present invention.
Figure 37B:
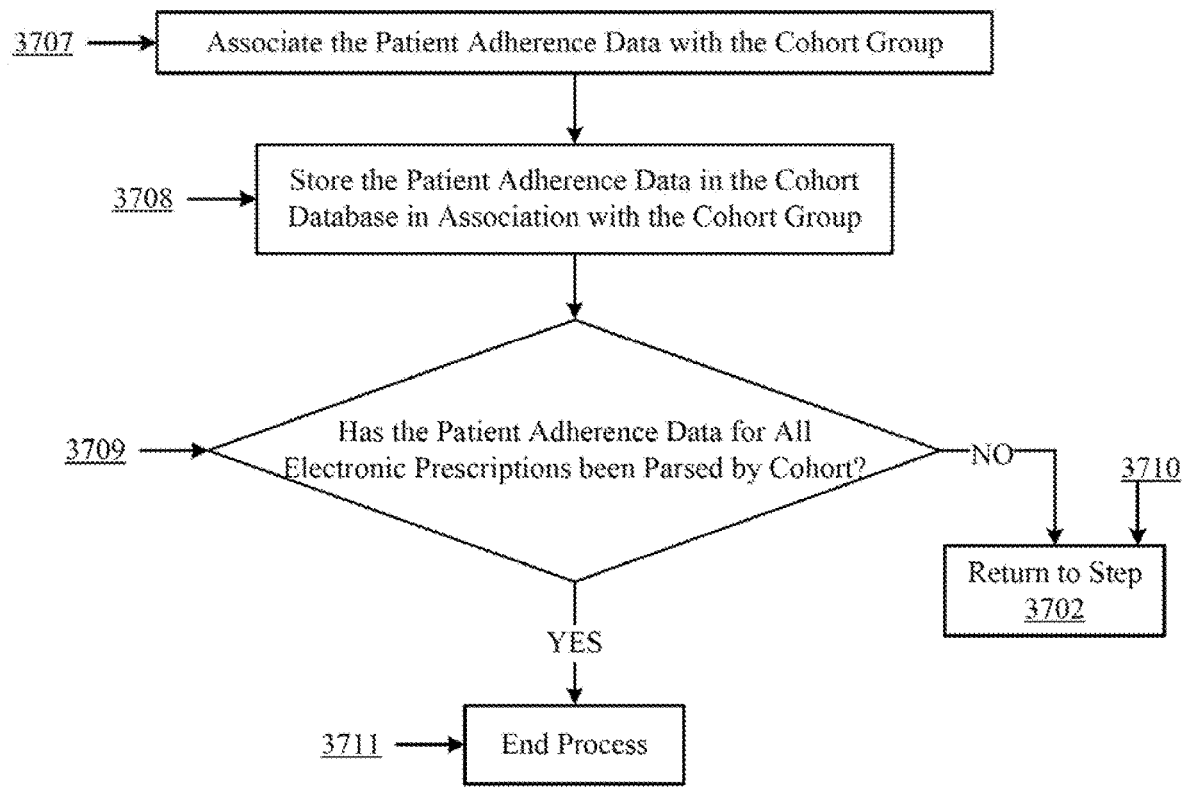

Referring to FIGS. 37*a*-37*b*, a flow chart of a method of parsing patient adherence data into data grouping based on a plurality of different cohorts according to an embodiment of the present invention is illustrated. The method 3700 begins when the SP module receives patient adherence data relating to a plurality of electronic prescriptions, thereby completing step 3701. It should be noted that the SP module may receive patient adherence data on a periodic basis (e.g., once a day), or the SP module may receive patient adherence data on a continuous basis. Further, the patient adherence data may relate to prescriptions that were associated with a particular cohort or not. As discussed in more detail below, the SP module parses the patient adherence data on the basis of cohort to determine the effectiveness of the permutation of supplemental programs of each cohort.

After receiving patient adherence data, the SP module processes the data and extracts the provider's NPI number and prescribed substance name from the electronic prescription associated with the patient adherence data, thereby completing step 3702 and 3703. It should be noted that the patient adherence data comprises information that relates to a corresponding electronic prescription processed by the EP module, and is therefore stored within the record database 304 of the SP system 300. As a result, the SP module can extract the provider's NPI number and substance name from the underlying electronic prescription associated with the patient adherence data.

After extracting the provider's NPI number and substance name, the SP module determines whether the health care provider 101 identified by the NPI number is associated or part of a cohort, thereby completing decision step 3704. According to one embodiment of the present invention, the determination is made by the SP module by a cross-referencing of the cohort relation table discussed above. In such instances, the SP module may cross-reference the provider's NPI number with the cohort relation table to determine whether the provider is part of a cohort. If the provider 101 identified by the NPI number is not associated with a cohort, then the method returns to step 3702 and the SP module processes patient adherence data relating to another prescription. However, if the provider 101 identified by the NPI number is associated with a cohort, then the method continues to decision step 3705.

At decision step 3705, the SP module determines whether the prescribed substance identified by the electronic prescription is associated with one of the provider's cohort(s) identified in step 3704. Similar to above and according to one embodiment of the present invention, the determination is made by the SP module by a cross-referencing of the cohort relation table discussed above. In such instances, the SP module may cross-reference the prescribed substance name with the cohort relation table to determine whether the prescribed substance is associated with one of the provider's cohort(s) identified in step 3704. If the prescribed substance name does not correspond with the prescribed substance of one of the provider's cohort(s), then the method returns to step 3702 and the SP module processes patient adherence data relating to another prescription. However, if the prescribed substance name does correspond with the provider's cohort, then the method continues to step 3706.

It should be noted that in such instances, the patient adherence data relates to an electronic prescription that meets all the cohort rules of the provider's cohort. However, at decision step 3706, the SP module determines whether the electronic prescription caused the permutation of supplemental programs of the provider's cohort were activated by the SP module. Stated another way, the SP module determines whether the cohort rules were met by the electronic prescription and whether the current counter was at or below the maximum counter when the SP module processed the electronic prescription when determining if the permutations of supplemental programs for the cohort would be activated.

In one embodiment of the present invention, when a permutation of supplemental programs of a cohort is activated for a prescription, the SP module tags the corresponding prescription. The corresponding prescription, the permutation of supplemental programs, and the tag are all stored in correlation with each other in the records database 304 or other databases of the SP system 300. Thereafter, the SP module uses the tag to determine whether the permutation of supplemental programs of a cohort was activated for an electronic prescription. For example, when receiving patient adherence data, SP module cross-references the records database 304 to see if the appropriate tag is associated with the corresponding prescription, thereby indicating that the permutation of supplemental programs was activated. Nonetheless, the invention is not so limited, and in alternate embodiments of the present invention, the patient adherence generation module 306 may determine whether the permutation of supplemental programs was activated for a particular prescription using other methods.

Next, after the SP module determines that the electronic prescription caused the permutation of supplemental programs of the provider's cohort to be activated by the SP module, the SP module associates the patient adherence data with the corresponding cohort of the health care provider 101, thereby completing step 3707. Thereafter, the SP module stores the patient adherence data in association with the health care provider's cohort in the cohort database 305, thereby completing step 3708.

Next, at decision step 3709, the SP module determines whether all of the received patient adherence data for all the prescriptions has been parsed by cohort. If so, then the process ends at step 3711. However, if there remains patient adherence data that has not been parsed by the SP module, then the Method 3700 continues to step 3710, and as such, returns to step 3702 discussed above.

According to one embodiment of the present invention, more than one prescription of a patient may be combined in order to determine compliance data. Thus, if a patient has more than one prescription for a given substance, it may be the case that the prescriptions should be combined for the purposes of calculating compliance data. For example, prescriptions may be combined if they are for the same patient and the same substance, and the prescriptions have overlapping prescription dates. For example, if prescription 1 has a start date of Mar. 1, 2011 and stop date of Jun. 1, 2011 and prescription 2 has a start date of May 1, 2011 and a stop date of Oct. 1, 2011, then the prescriptions may be combined and considered one prescription for the purposes of determining patient adherence data.

4. Analyzing the Patient Adherence Data to Determine the Effectiveness of the Different Permutations of Supplemental Programs on Patient Adherence After parsing the patient adherence data by cohort, the SP module analyzes the patient adherence data to determine the effectiveness of each of the different permutations of supplemental programs on patient adherence. In one embodiment of the present invention, when the current counter of all the cohorts of a program cohort group reach the maximum counter, the SP module ceases to activate the permutations of supplemental programs for the cohorts of the program cohort group, and begins to analyze patient adherence data to determine the effectiveness of the different permutations of the supplemental programs of a program cohort group on patient adherence. However, in other embodiments of the present invention, the SP module may analyze patient adherence data continuously in real-time, even as the SP module is also still activating permutations of supplemental programs for a program cohort group.

According to one embodiment of the present invention, one of the cohorts out of the plurality of cohorts of the program cohort group is a control group. Since the control group either does not comprise any associated supplemental programs (i.e., the permutation of supplemental programs of the control group is empty) or the control group comprises one or more supplemental programs that are also associated with every one of the other cohorts of the program cohort group, then the control group can be used as a basis of comparison to determine the effectiveness of the supplemental programs of the other cohorts of the program cohort group. Stated more simply, the SP module may determine the effectiveness of the permutations of supplemental programs by using the control group as a baseline indicator of standard patient adherence to the target drug.

In embodiments that do not comprise a control group, the basis of comparison may be the average patient adherence for the target drug in general. This may be determined by the SP module in many ways, including but not limited to, the patient adherence data for the target drug that is stored within the patient adherence database 307 and was generated by the patient adherence generation module 306. Further, in other embodiments that do not comprise a control group, the different cohorts may be simply compared to one another, with the assumption that the permutations of supplemental programs have a beneficial effect on patient adherence. After determining a basis of comparison (e.g., the control group), the SP module will analyze the patient adherence data of each cohort of a program cohort group to determine the effectiveness of each of the different permutations of supplemental programs on patient adherence.

In one embodiment of the present invention, the SP module determines the effectiveness using one or more algorithms that are configured to compare multiple sets of data to one another. According to one embodiment of the present invention, the algorithms are stored within the cohort database 305. The data that is compared to determine the effectiveness of the permutations of supplemental programs on patient adherence includes, but is not limited to, patient adherence data, coupon redemption data, and patient feedback data.

After the data is compared using the one or more algorithms, the SP module may display effectiveness data on a display device to an administrator of the SP system 300. This allows the administrator of the SP system 300 to visually interpret which permutation of supplemental programs was most effective for encouraging patient adherence to the target drug. As discussed in more detail below, the effectiveness data may be displayed in graphical representations or in numerical values.

Figure 38A:
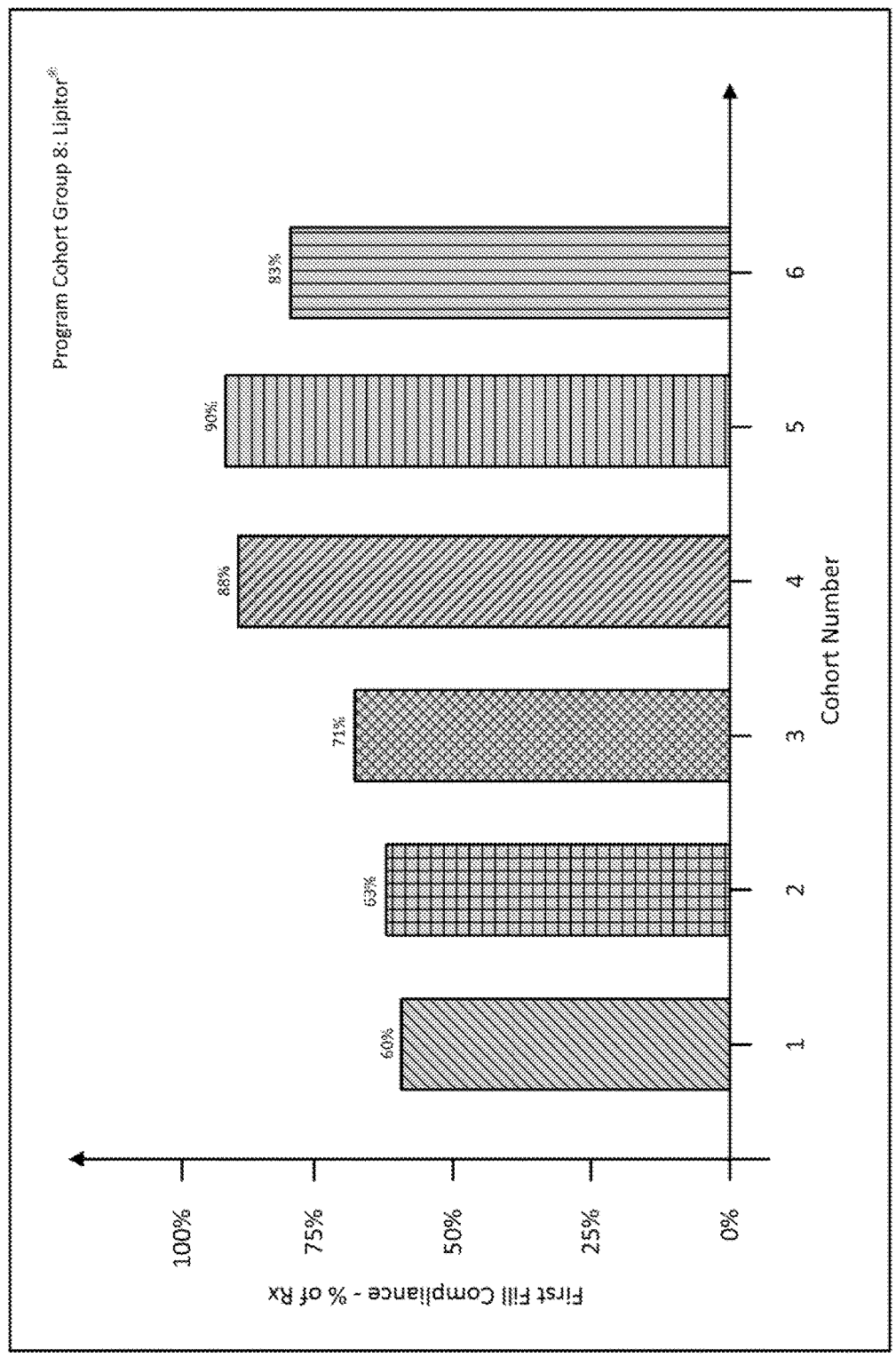
FIG. 38a is a graphical representation of the effectiveness of different permutations of supplemental programs on patient's first fill compliance according to one embodiment of the present invention.

Referring to FIG. 38*a*, a graphical representation of the effectiveness of different permutations of supplemental programs on patient's first fill compliance according to one embodiment of the present invention is illustrated. For example, in one embodiment of the present invention, the SP module determines the effectiveness of the permutations of supplemental programs by comparing the first fill compliance data of the prescriptions of a cohort to the other cohorts of the program cohort group. It should be noted that first fill compliance (FFC) data indicates whether the patient filled the medication promptly after receiving the prescription. Further, in embodiments where one of the cohorts out of the plurality of cohorts is a control cohort, the SP module will compare the FFC data of the prescriptions of each cohort with the control cohort in order to determine the effectiveness of the supplemental programs of each cohort. The permutation of supplemental programs of the cohort whose prescriptions have the highest FFC data will be considered the most effective on patient adherence. This is because the patients receiving that permutation of supplemental programs of that cohort were more likely to comply with the first fill of the prescription, and this increase in adherence is determined to be due from the supplemental programs those patients received.

Figure 38B:
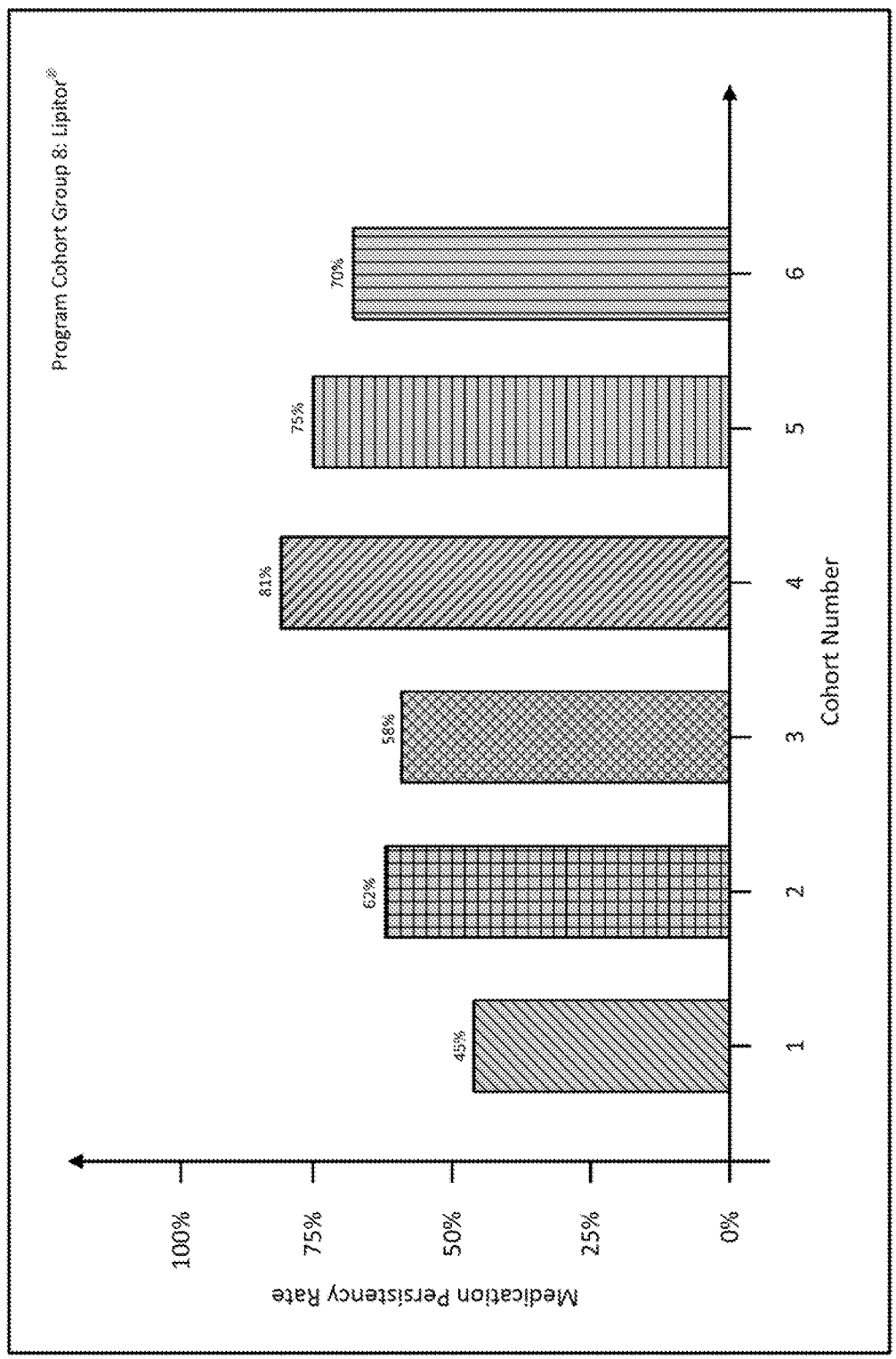
FIG. 38b is a graphical representation of the effectiveness of different permutations of supplemental programs on patient's medication persistency rate according to one embodiment of the present invention.

Referring to FIG. 38b, a graphical representation of the effectiveness of different permutations of supplemental programs on patient's medication persistency rate displayed on a display device according to one embodiment of the present invention is illustrated. For further example, in one embodiment of the present invention, the SP module determines the effectiveness of the permutations of supplemental programs by comparing the patient Medication Persistency Rate (MPR) data of the prescriptions of a cohort to the other cohorts of the program cohort group. It should be noted that MPR data is a percentile (from 0-100%) that indicates how often a patient filled a medication compared with how often s/he could have done so. Specifically, in embodiments where one of the cohorts out of the plurality of cohorts is a control cohort, the SP module will compare the MPR data of the prescriptions of each cohort with the control cohort in order to determine the effectiveness of the supplemental programs of each cohort. The permutation of supplemental programs of the cohort whose prescriptions have the highest MPR data will be considered the most effective on patient adherence. This is because the patients receiving, that permutation of supplemental programs of that cohort were more likely to fill their prescription when having the opportunity.

Specifically, referring to FIGS. 38a and 38b concurrently, cohort number 1 is the control cohort, while cohort numbers 2-6 are other cohorts of the program cohort group that were each assigned a different permutation of supplemental programs to measure the effectiveness of those programs on patient adherence. It should be noted that cohort number 1 was not assigned any supplemental programs (i.e., its permutation of supplemental programs is empty). Further, the program control group is program control group 8, and the target drug is Lipitor®. As illustrated in FIG. 38a, cohort number 1, which was the control group, has a FFC of 60%. This means that 60% of the prescriptions that were written by the health care providers 101 of cohort 1 for the target drug were filled within the first fill interval of the prescription. Further, as illustrated in FIG. 38b, cohort number 1, which was the control group, has a MPR of 45%. This means that, on average, the patients who were prescribed the target drug by the health care providers 101 of cohort 1 had an MPR of 45%. Cohort number 1's FFC of 60% and MPR of 45% may be used as a baseline to determine the effectiveness of the other permutations of supplemental programs were assigned to the other cohorts.

As noted above, FIGS. 38a and 38b are two examples of graphical representations of the effectiveness of different permutations of supplemental programs on patient adherence. As exemplified in FIG. 38a, cohort number 5 has the highest FFC rate of 90%, and therefore, the permutation of supplemental programs assigned to cohort number 5 is the most effective at increasing patient's first fill compliance to the target drug. By contrast, cohort number 2 has the lowest FFC rate of the non-control cohorts of 63%, and therefore, the permutation so supplemental programs assigned to cohort number 2 is the least effective in increasing patient's first fill compliance to the target drug. Moreover, as exemplified in FIG. 38b, cohort number 4 exemplifies the highest MPR of 81%, and therefore, the permutation of supplemental programs assigned to cohort number 4 is the most effective at increasing a patient's persistence to the target drug regimen. By contrast, cohort number 3 exemplifies the lowest MPR rate of the non-control cohorts of 58%, and therefore, the permutation of supplemental programs assigned to cohort number 3 is the least effective at increasing a patient's persistence to the target drug regimen. Thus, as illustrated, depending on the means of measurement of patient adherence (FFC, MPR, etc.), different permutations of supplemental programs may be most effective. As a result, by using cohorts to test the effectiveness of supplemental programs on a variety of different measurements of patient adherence, the SP module may be used to determine the most effective combination of supplemental programs to increase patient adherence in the most desired manner.

However, it should be noted that the invention is not so limited, and in other embodiments of the present invention, the SP module determines the effectiveness of the permutations of supplemental programs by comparing one or more forms of patient adherence data of the prescriptions of the plurality of cohorts of the program cohort group. Stated another way, the invention is not limited to comparing FFC data and MPR data when determining the effectiveness of the plurality of cohorts of a program cohort group. Any patient adherence data may be used by the SP module. Finally, it should be noted that the graphic representation exemplified in FIGS. 38a and 38b may be displayed on a display device of the administrator of the SP system 300, to a pharmaceutical company, or to any other person or system of the system 1000.

For even further example, in another embodiment of the present invention, every cohort of a program cohort group, including a control cohort comprises a supplemental program that distributes a coupon for the target drug to the patient upon activation. In such instances, the non-control cohorts of the program cohort group all comprise different supplemental programs in addition to the supplemental program that distributes a coupon. As a result, the SP module measures the effectiveness of each permutation of supplemental programs by comparing the rates of coupon redemption of the prescriptions of each cohort of the program cohort group. Therefore, the patients who are receiving the permutation of supplemental programs of the cohort with the highest effectiveness on patient adherence will have redeemed their coupon more often that the patients receiving the permutations of supplemental programs of the other cohorts.

According to one embodiment of the present invention, after determining the effectiveness of the supplemental programs on patient adherence, the SP module generates patient adherence reports based on the determined effectiveness. After generation of the reports, the SP module mail deliver the reports to any one of the administrators of the SP system 300, any other system or module of the system 1000, or a particular pharmaceutical company. Examples of graphical reports are exemplified in FIGS. 38a and 38b. Nonetheless, it should be noted that the invention is not limited to any specific type or format or graphical report. Further, in alternate embodiments of the present invention, the patient adherence data of each cohort may be displayed purely as numerical value, as numerical values and graphical representations, or just graphical representations.

After the graphical report is generated by the SP module, the graphical report is saved to the cohort database 305 of the SP system 300. Further, according to one embodiment of the present invention, the cohort relation table is updated with the graphical report stored in association with the associated health care provider 101 and cohort of the graphical report.

While the embodiment of the present invention has been described with reference to the accompanying drawings, it can be understood by those skilled in the art that the present invention can be embodied in other specific forms without departing from its spirit or essential characteristics. Therefore, the foregoing embodiments and advantages are merely exemplary and are not to be construed as limiting the present invention. The present teaching can be readily applied to other types of apparatuses. The description of the foregoing embodiments is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

We claim:

1. A method implemented on a computing device having at least one processor, storage, and a communication platform connected to a network, the method comprising:
   receiving, at the computing device, electronic prescription data for a prescribed substance for a patient;
   determining that the electronic prescription data matches a prescribed substance code or diagnostic code for a cohort in a program cohort group, the program cohort group including a plurality of cohorts, each cohort including a maximum prescription counter, a current prescription counter, and a supplemental program permutation;
   responsive to determining that the electronic prescription data qualifies for the cohort and that the current prescription counter for the cohort is less than the maximum prescription counter for the cohort:
      incrementing the current prescription counter for the cohort, and
      tagging the electronic prescription data as activated in connection with the cohort;
   receiving, responsive to tagging the electronic prescription data as activated in connection with the cohort, medical history data for the patient and for the prescribed sub stance;
   determining, responsive to determining the current prescription counter for each cohort in the program cohort group is at least the maximum prescription counter for the cohort, the medical history data for tagged prescriptions in each cohort in the program cohort group to determine a chosen cohort of the plurality of cohorts for the program cohort group, the chosen cohort having highest patient adherence based on the medical history data; and
   generating, responsive to receiving a new electronic prescription for the prescribed substance for another patient, a notification to the other patient including the supplemental programs associated with the chosen cohort.

2. The method of claim 1, further comprising:
   determining a decile level for each of a plurality of providers, the decile level being an indicator of a frequency with which the provider prescribes the prescribed substance; and
   assigning the plurality of providers to cohorts so that cohorts have a similar average decile level.

3. The method of claim 1, wherein said electronic prescription data qualifies for a cohort responsive to further receiving a selection of the supplemental programs for the cohort from a health care provider identified in the electronic prescription data.

4. The method of claim 1, wherein each cohort further includes a cohort rule and the electronic prescription data qualifies for a cohort responsive to further determining that the cohort rule is satisfied.

5. The method of claim 4, wherein the cohort rule specifies a range for a percentage that represents how often a patient filled a prescription compared to how often the prescription could optimally have been filled.

6. A method implemented on at least one computing device each of which has at least one processor, storage, and a communication platform connected to a network, the method comprising:
   receiving, at a computing device, a plurality of electronic prescriptions generated by a plurality of health care providers for a prescribed substance;
   determining, for each electronic prescription, whether the electronic prescription qualifies for one cohort of a plurality of cohorts, each cohort in the plurality of cohorts identifying a different permutation of supplemental programs that were previously selected by the plurality of health care providers for the prescribed substance;
   for each electronic prescription that qualifies for a cohort:
      retrieving a permutation of supplemental programs identified by the cohort,
      providing the supplemental programs in the permutation to a recipient of the electronic prescription,
      tagging the electronic prescription as activated in connection with the cohort, and
      receiving, responsive to tagging the electronic prescription as activated, medical history data for a patient associated with the electronic prescription and the prescribed substance, the medical history data including patient adherence data;
   determining effectiveness of each of the permutations in the plurality of cohorts based on the patient adherence data; and
   providing supplemental programs from a most effective permutation in response to receipt of a new electronic prescription of the prescribed substance.

7. The method of claim 6, further comprising:
   incrementing, for each electronic prescription that qualifies for a cohort, a current prescription counter for the cohort,
   wherein determining the effectiveness of each of the permutations occurs subsequent to the current prescription counter meeting a minimum threshold.

8. The method of claim 6, wherein each of the plurality of cohorts comprises a decile level for the prescribed substance or medical specialties of the plurality of health care providers.

9. The method of claim 6, further comprising, for each electronic prescription that qualifies for a cohort:
   presenting to a health care provider associated with the electronic prescription, on the computing device, the permutation of supplemental programs associated with the cohort for selection and activation; and
   receiving a selection from the health care provider that activates the permutation of supplemental programs associated with the cohort,
   wherein the tagging occurs responsive to receiving the selection.

10. The method of claim 6, wherein the patient adherence data is collected from a payor and/or a pharmacy system.

11. The method of claim 6, wherein at least one permutation of the supplemental programs comprises a coupon for the prescribed substance, and the patient adherence data is based at least in part on rates of coupon redemption.

12. The method of claim 6, wherein providing the supplemental programs includes:
   retrieving, from one or more databases, a first set of delivery modes that are available for the patient associated with the electronic prescription;

retrieving, from the one or more databases, a second set of delivery modes that are associated with each supplemental program;

comparing, at the computing device, the first set of delivery modes and the second set of delivery modes to identify a list of common delivery modes that are available for the patient and associated with one or more supplemental programs; and presenting the one or more supplemental programs with the list of common delivery modes for selection and acceptance.

13. The method of claim 6, wherein the permutation of supplemental programs comprises a prescription reminder service, and the method further comprises:

transmitting data related to an electronic prescription and a patient associated with the permutation to the prescription reminder service.

14. The method of claim 6, wherein the permutation of supplemental programs comprises a prescribed substance education service, and the method further comprises:

retrieving educational content related to a prescribed substance from one or more databases; and transmitting the educational content to a patient associated with the permutation.

15. The method of claim 6, wherein the permutation of supplemental programs comprises a coupon service, and the method further comprises:

retrieving coupon data related to a prescribed substance from one or more databases; and integrating the coupon data into an electronic prescription generated for the prescribed sub stance.

16. The method of claim 6, wherein the permutation of supplemental programs comprises an appointment reminder service, and the method further comprises:

transmitting data related to a patient associated with the permutation and an appointment schedule to the appointment reminder service.

17. The method of claim 6, wherein determining that the electronic prescription qualifies for one of the cohorts includes:

determining that a health care provider associated with the electronic prescription exists in health care provider identifiers for the cohort;

determining that the prescribed substance for the electronic prescription matches the prescribed substance for the cohort or that a diagnostic code for the electronic prescription matches a diagnostic code for the cohort; and determining that a current prescription counter for the cohort is less than a maximum prescription counter for the cohort.

18. The method of claim 6, wherein the medical history data includes data from which to determine: number of refills, prescription start date, prescription stop date, information relating to whether the patient picked up the prescription, number of refills of the prescription that the patient filled, and a time frame between refills in comparison to a duration of each prescription.

19. A computer system for determining effectiveness of supplemental programs with respect to patient adherence, the computer system comprising:

a processor;

a memory;

a network interface; and instructions residing on the memory, which when executed by the processor, cause the processor to perform operations including:

generating a first user interface for receiving an electronic prescription for a patient from a health care provider;

receiving, via the first user interface, the electronic prescription for a prescribed substance; and responsive to receiving the electronic prescription:

identifying, from a database of supplemental programs, a permutation of supplemental programs from a cohort of a program cohort group, the program cohort group being for the prescribed substance and the cohort being a cohort in the program cohort group that has a highest adherence score of cohorts in the program cohort group, generating a second user interface that presents the permutation of supplemental programs for selection by the health care provider, and responsive to receiving selection of at least some of the supplemental programs in the permutation of supplemental programs, providing the supplemental programs to the patient.

* * * * *

UNITED STATES PATENT AND TRADEMARK OFFICE
CERTIFICATE OF CORRECTION

PATENT NO. : 10,832,364 B2
APPLICATION NO. : 16/430217
DATED : November 10, 2020
INVENTOR(S) : Tayal et al.

It is certified that error appears in the above-identified patent and that said Letters Patent is hereby corrected as shown below:

In the Claims

In Column 73, Line 35, Claim 1, delete "sub stance;" and insert -- substance; --, therefor.

In Column 75, Line 31, Claim 15, delete "sub stance." and insert -- substance. --, therefor.

Signed and Sealed this
Eleventh Day of June, 2024

Katherine Kelly Vidal
*Director of the United States Patent and Trademark Office*